(12) United States Patent
Clayton et al.

(10) Patent No.: US 8,577,617 B2
(45) Date of Patent: Nov. 5, 2013

(54) METABOLIC PHENOTYPING

(76) Inventors: Thomas Andrew Clayton, Sandwich (GB); Jeremy Ramsey Everett, Sandwich (GB); John Christopher Lindon, Sandwich (GB); Jeremy Kirk Nicholson, Sandwich (GB)

( * ) Notice: Subject to any disclaimer, the term of this patent is extended or adjusted under 35 U.S.C. 154(b) by 175 days.

(21) Appl. No.: 12/233,996

(22) Filed: Sep. 19, 2008

(65) Prior Publication Data
US 2009/0192721 A1    Jul. 30, 2009

Related U.S. Application Data

(63) Continuation of application No. 10/755,061, filed on Jan. 8, 2004, now abandoned, which is a continuation of application No. PCT/IB03/02309, filed on Jun. 16, 2003.

(30) Foreign Application Priority Data

Jun. 14, 2002 (GB) .................................... 0213786.7
Jun. 17, 2002 (GB) .................................... 0213895.6

(51) Int. Cl.
*G06F 19/00* (2011.01)
*G06F 17/10* (2006.01)

(52) U.S. Cl.
USPC ............................................. 702/19; 703/11

(58) Field of Classification Search
None
See application file for complete search history.

(56) References Cited

U.S. PATENT DOCUMENTS 6,658,396 B1    12/2003    Tang et al. ....................... 706/17

FOREIGN PATENT DOCUMENTS

WO    WO 02/10746 A2    2/2002
WO    WO 03/107270 A2    12/2003

OTHER PUBLICATIONS

Holmes et al. (NMR in Biomedicine (1998) vol. 11, pp. 235-244).*
Anthony et al. (Journal of Pharmaceutical and Biomedical Analysis (1995) vol. 13, pp. 205-211).*
Nicholson et al. (Nature Reviews (2002) vol. 1, pp. 153-161).*
Holmes et al. (Chem. Res. Toxicol. (2001) vol. 14, pp. 182-191).*
Toxicology Letters (2001) vol. 120 in articles entitled "Genetic variability in susceptibility and response to toxicants" by Ingelman-Sundberg (pp. 259-268) and by Miller et al (pp. 269-280).
Nicholson and Wilson (1989), High resolution proton magnetic resonance spectroscopy of biological fluids, Progress in NMR Spectroscopy, 21, 449-501.
Lindon et al. (1999), NMR spectroscopy of biofluids, Annual reports on Nmr spectroscopy, 38.

Moka et al. (1997), Magic angle spinning proton nuclear magnetic resonance spectroscopic analysis of intact kidney tissue samples, Analytical Communications, 34 107-109).
Holmes et al. (1992) NMR spectroscopy and pattern recognition analysis of the biochemical processes associated with the progression and recovery from nephrotoxic lesions in the rat induced by mercury (II) chloride and 2-bromoethanamine, Mol. Pharmacol., 42, 922-930.
Moolenaar et al. (2003) Proton nuclear magnetic resonance spectroscopy of body fluids in the field of inborn errors of metabolism, Ann. Clin. Biochem., 40, 1, 16-24.
Nicholson et al. (1999), 'Metabonomics': understanding the metabolic responses of living systems to pathophysiological stimuli via multivariate statistical analysis of biological NMR spectroscopic data, Xenobiotica, 29, 1181-1189.
Frank et al. (1984) Prediction of product quality from spectral data using the partial least squares method, J. Chem. Info. Comp., 24, 20.
Anker and Jurs (1992) Prediction of C-13 nuclear magnetic resonance chemical shifts by artificial neural networks, Anal. Chem., 64, 1157.
Specht (1990) Probabilistic neural networks, Neur. Networks, 3, 109.
Quinlan (1986) Induction of decision trees, Machine Learning, 1, 81.
Anthony et al. (1994) Pattern recognition classification of the site of nephrotoxicity based on metabolic data derived from proton nuclear magnetic resonance spectra of urine, Mol. Pharmacol., 46, 199-211.
Beckwith-Hall et al. (1998) Nuclear magnetic resonance spectroscopic and principal components analysis investigations into biochemical effects of three model hepatotoxins, Chem. Res. Tox., 11, 260-272.
Gartland et al. (1990) Pattern recognition analysis of high resolution $^1$H NMR spectra of urine. A non-linear mapping approach to the classification of toxicological data, NMR in Biomedicine, 3, 166-172.

(Continued)

*Primary Examiner* — Lori A Clow
(74) *Attorney, Agent, or Firm* — Hamilton, Brook, Smith & Reynolds, P.C.

(57) ABSTRACT

A method of generating models with which to characterize selected aspects of the metabolic phenotype of subjects without dosing a test substance to those subjects or with which to predict, without dosing, the post-dose responses of subjects where those responses are dependent on metabolic phenotype, the method comprising: obtaining pre-dose data relating to a plurality of subjects before dosing with a dosing substance; obtaining post-dose data relating to the plurality of subjects after dosing with the dosing substance; and correlating inter-subject variation in the pre-dose data with inter-subject variation in the post-dose data, and generating a pre-to-post-dose predictive model on the basis of the observed correlation. The models may be used to determine selected aspects of the metabolic phenotype of a subject or to predict, without dosing, the post-dose responses of subjects. This is achieved by analysing data relating to the un-dosed subject in relation to a model describing the correlation of pre-dose and post-dose data relating to a plurality of subjects when dosed with a particular substance which challenges the biochemical transformation or pathway of interest; and generating, according to the predetermined criteria of the model, a numerical measure or classification describing the metabolic phenotype of the un-dosed subject.

10 Claims, 36 Drawing Sheets

(56) References Cited

OTHER PUBLICATIONS

Holmes et al. (1994) Automatic data reduction and pattern recognition methods for analysis of $^1$H NMR spectra of human urine from normal and pathological states, Anal. Biochem., 220, 284-296.

Wold et al. (1998) Orthogonal Signal Correction of Near Infrared Spectra, Chemometrics and Intelligent Laboratory Systems, 44, 175-185.

Bollard et al. (2001) Investigations into biochemical changes due to diurnal variation and estrus cycle in female rats using high resolution (1)HNMR spectroscopy of urine and pattern recognition, Anal Biochem., 295, 2, 194-202.

Baud-Camus et al. (2001) Determination of N-acetylation phenotype using caffeine as a metabolic probe and high-performance liquidchromatography with either ultraviolet detection or electrospray massspectrometry, Chromatogr. B. Biomed. Sci. Appl., 760, 1, 55-63.

Lindon et al. (Concepts in Magnetic Resonance (2000) vol. 12 (5) pp. 289-320).

Bertilsson, L., and Kalow, W., "Chapter 2: Interethnic differences in drug disposition and effects." In *Interindividual Variability in Human Drug Metabolism*, Pacifici, G. M., and Pelkonen, O., eds. (London: Taylor & Francis), pp. 15-74 (2001).

Dumas, M.-E., et al., "Metabonomic Assessment of Physiological Disruptions Using $^1$H-$^{13}$C HMBC-NMR Spectroscopy Combined with Pattern Recognition Procedures Performed on Filtered.Variables," *Anal. Chem.*, 74: 2261-2273 (2002).

Hellmold, H., et al., "Identification of end points relevant to detection of potentially adverse drug reactions," *Toxicology Letters*, 127: 239-243 (2002).

Holmes, E., et al., "Chemometric Models for Toxicity Classification Based on NMR Spectra of Biofluids," *Chem. Res. Toxicol*, 13: 471-478 (2000).

Ingelman-Sundberg, M., "Genetic variability in susceptibility and response to toxicants," *Toxicology Letters*, 120: 259-268 (2001).

Kalow, W., "Chapter 1: Genetic factors that cause variability in human drug metabolism." In *Interindividual Variability in Human Drug Metabolism*, Pacifici, G. M., and Pelkonen, O., eds. (London: Taylor & Francis), pp. 1-14 (2001).

Miller, M. C., III, et al., "Genetic variability in susceptibility and response to toxicants," *Toxicology Letters*, 120: 269-280 (2001).

Nicholls, A. W., et al., "Metabonomic Investigations into Hydrazine Toxicity in the Rat," *Chem. Res. Toxicol.*, 14: 975-987 (2001).

Rane, A., "Chapter 3: Development and ageing as sources of variability in drug metabolism." In *Interindividual Variability in Human Drug Metabolism*, Pacifici, G. M., and Pelkonen, O., eds. (London: Taylor & Francis), pp. 75-84 (2001).

International Search Report from International Application No. PCT/IB2003/002309, mailed Mar. 11, 2005.

International Preliminary Examination Report from International Application No. PCT/IB2003/002309, dated Jun. 10, 2005.

\* cited by examiner

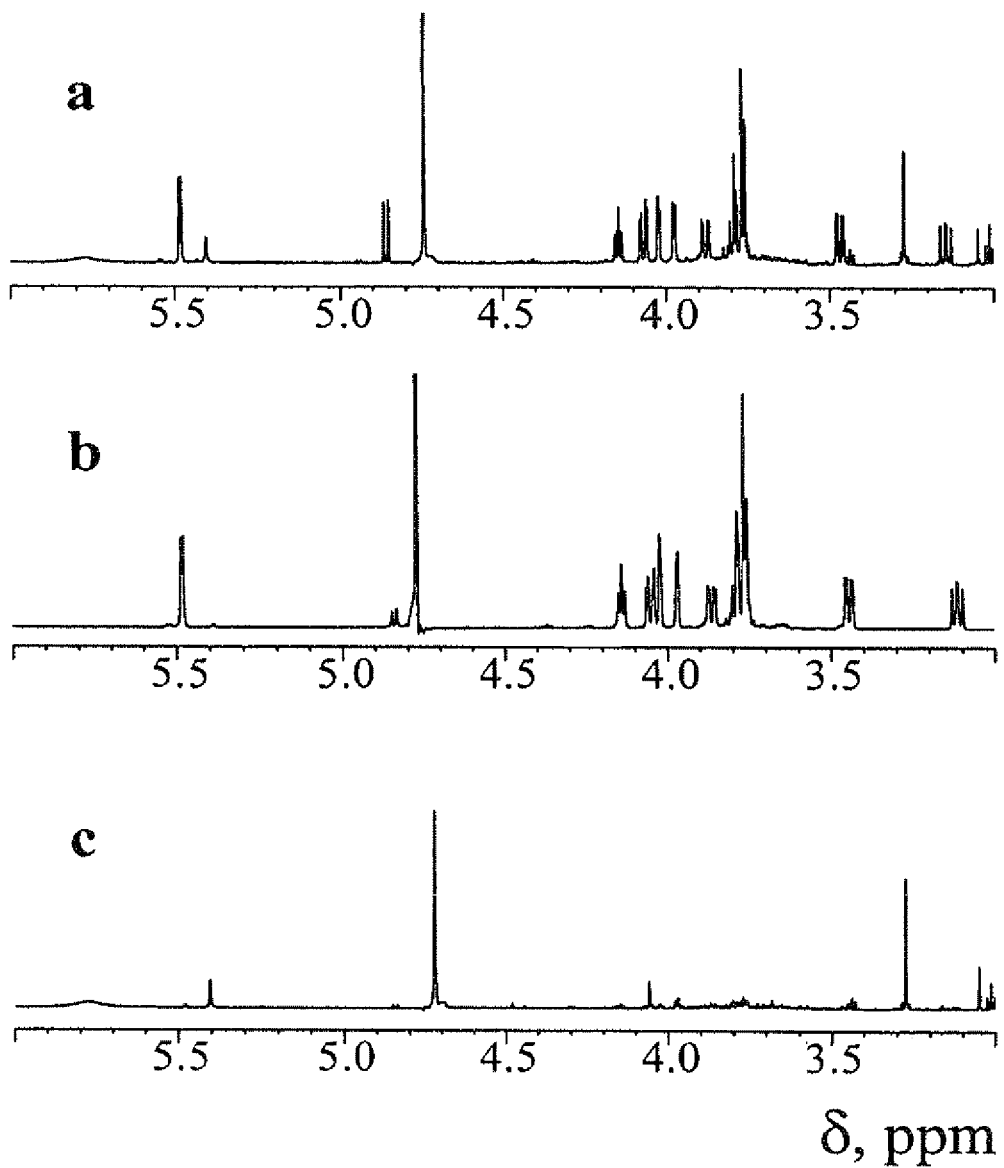
Figure 1.1

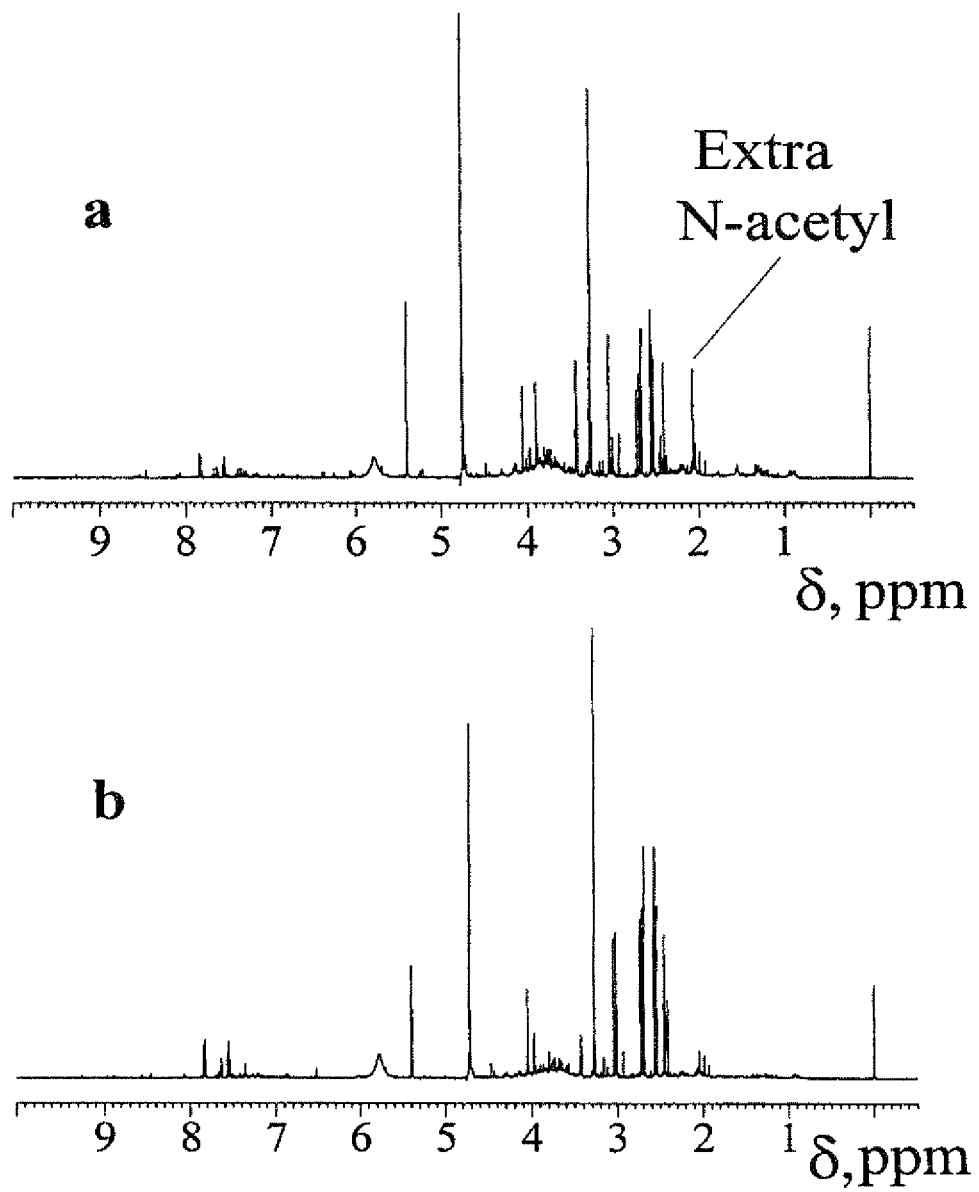
Figure 1.2

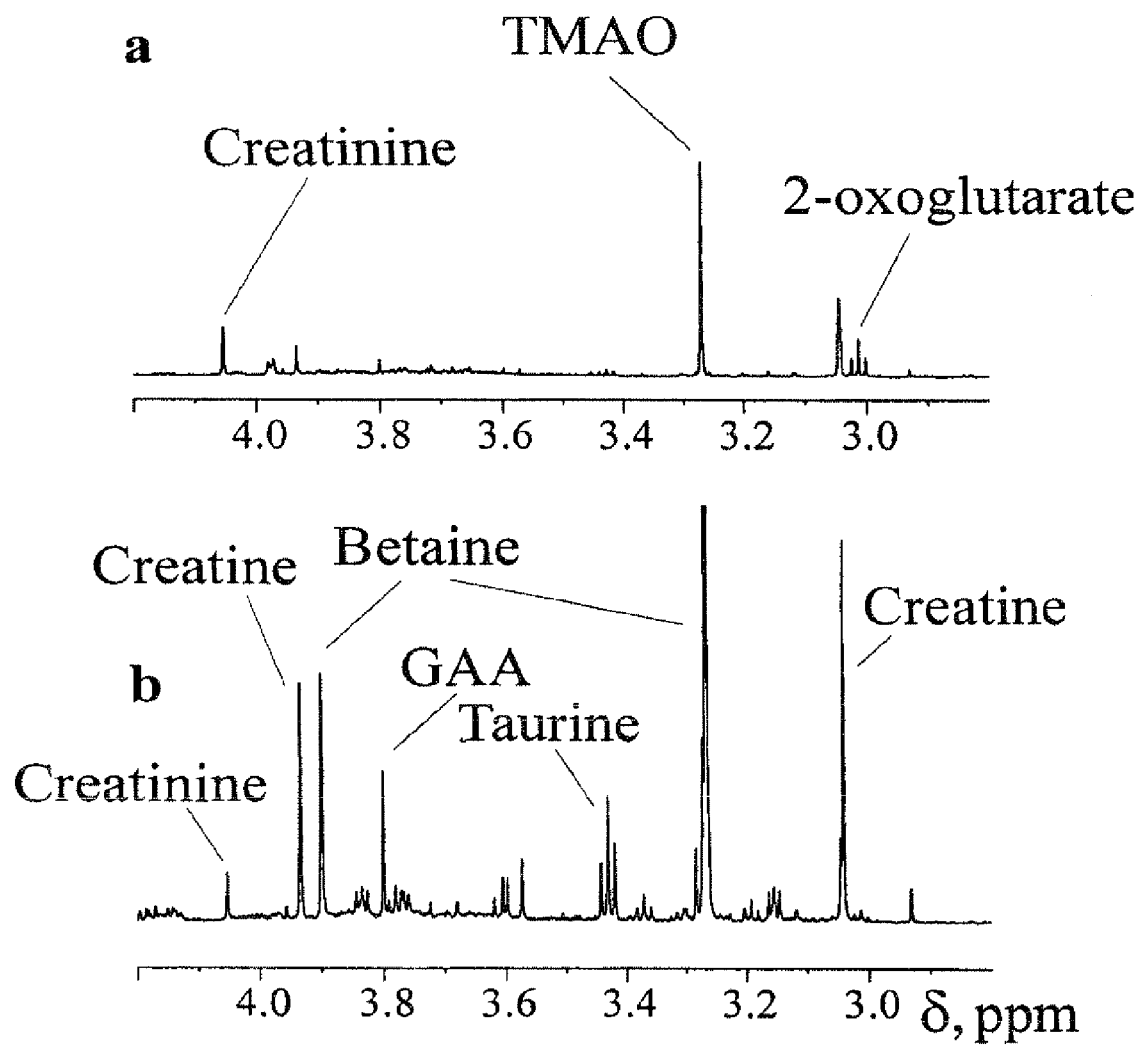
Figure 1.3

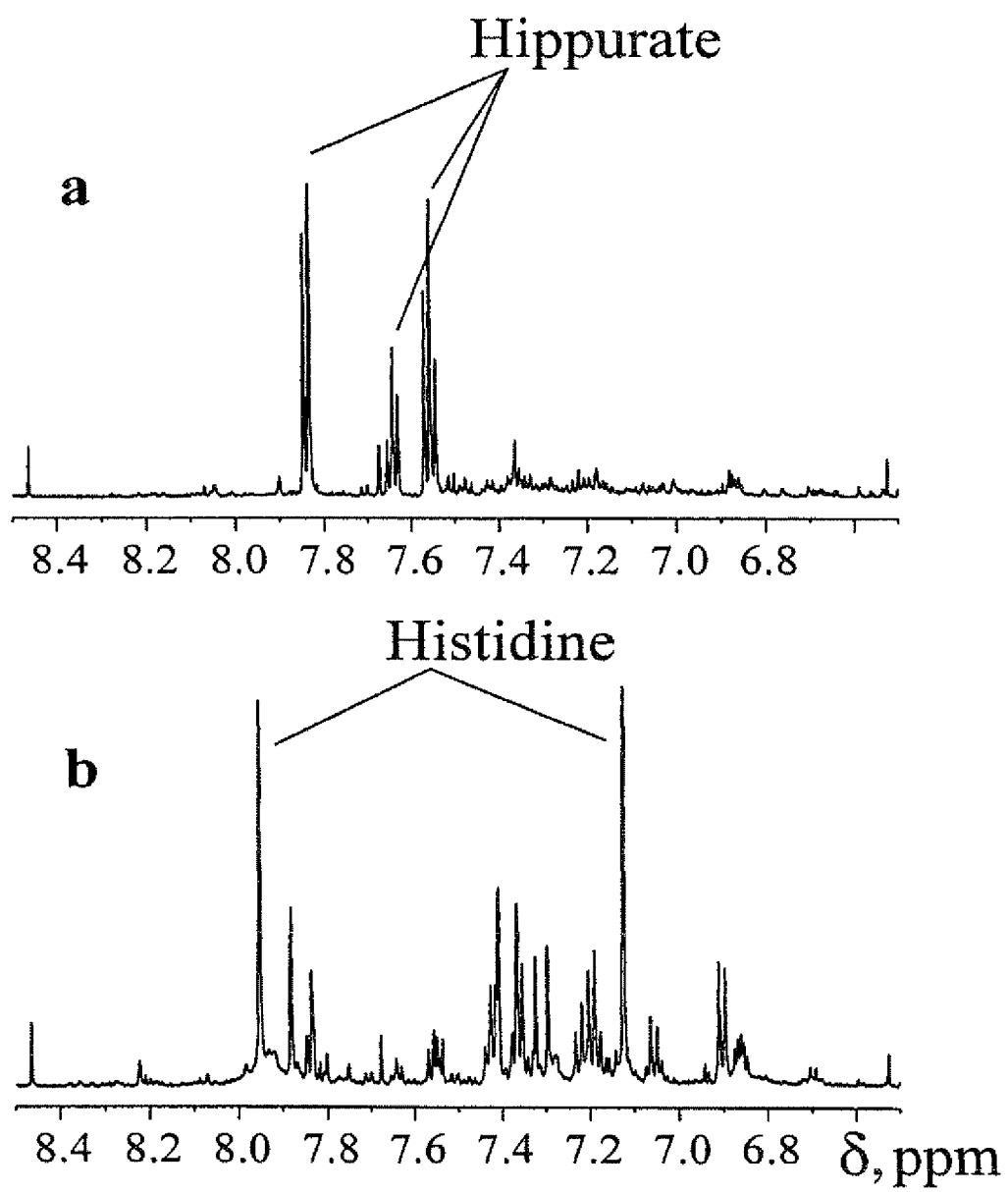
Figure 1.4

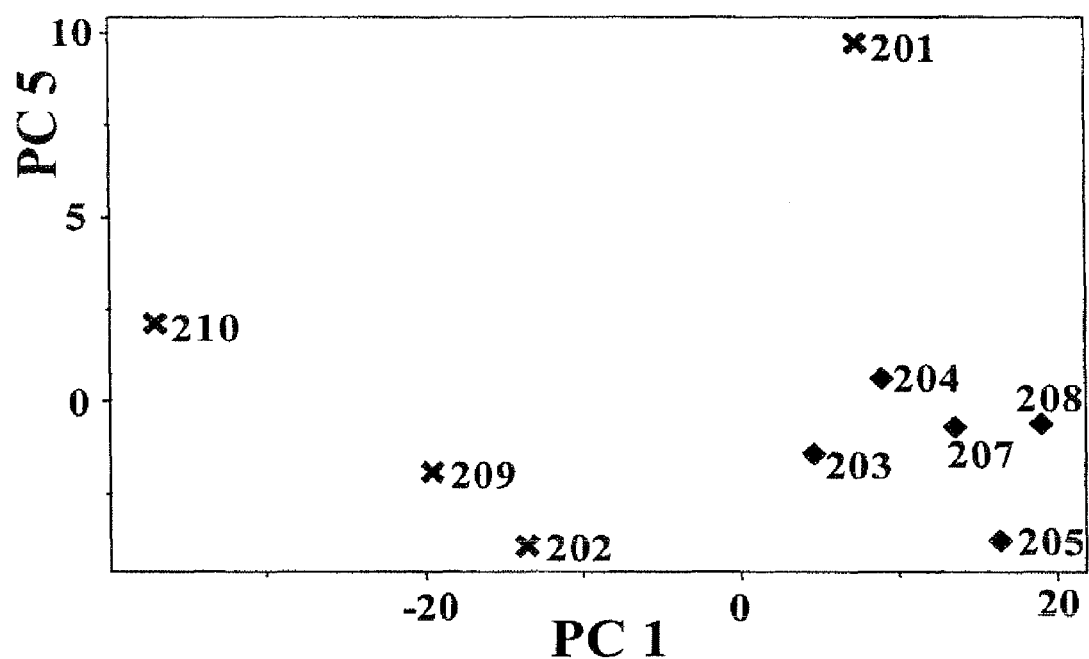
Figure 1.5

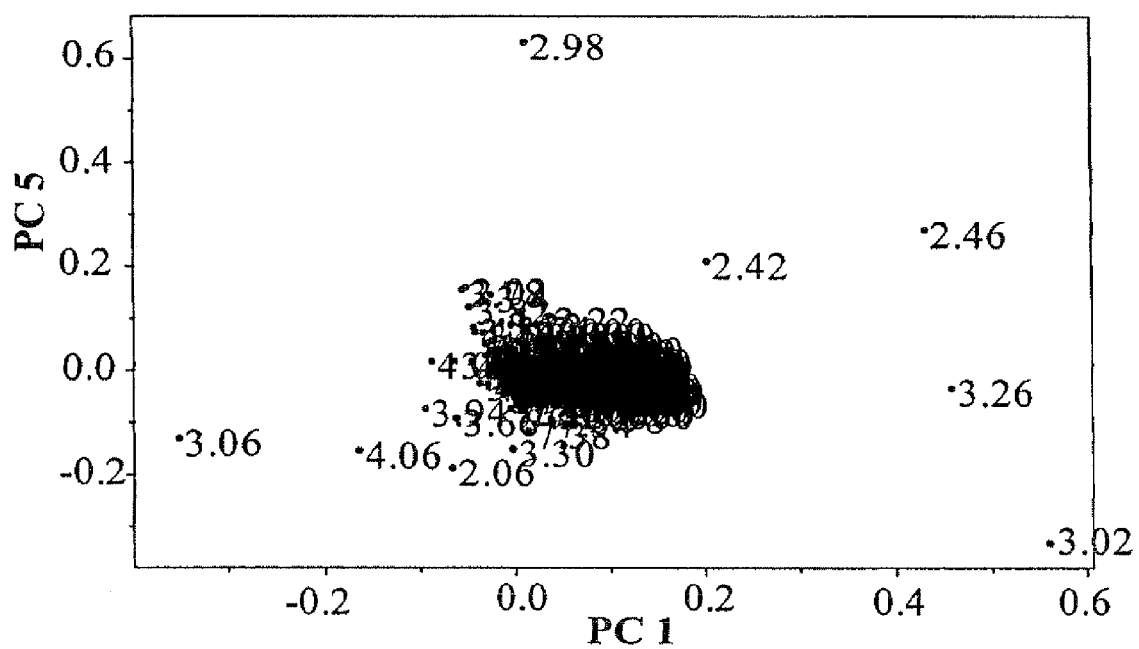
Figure 1.6

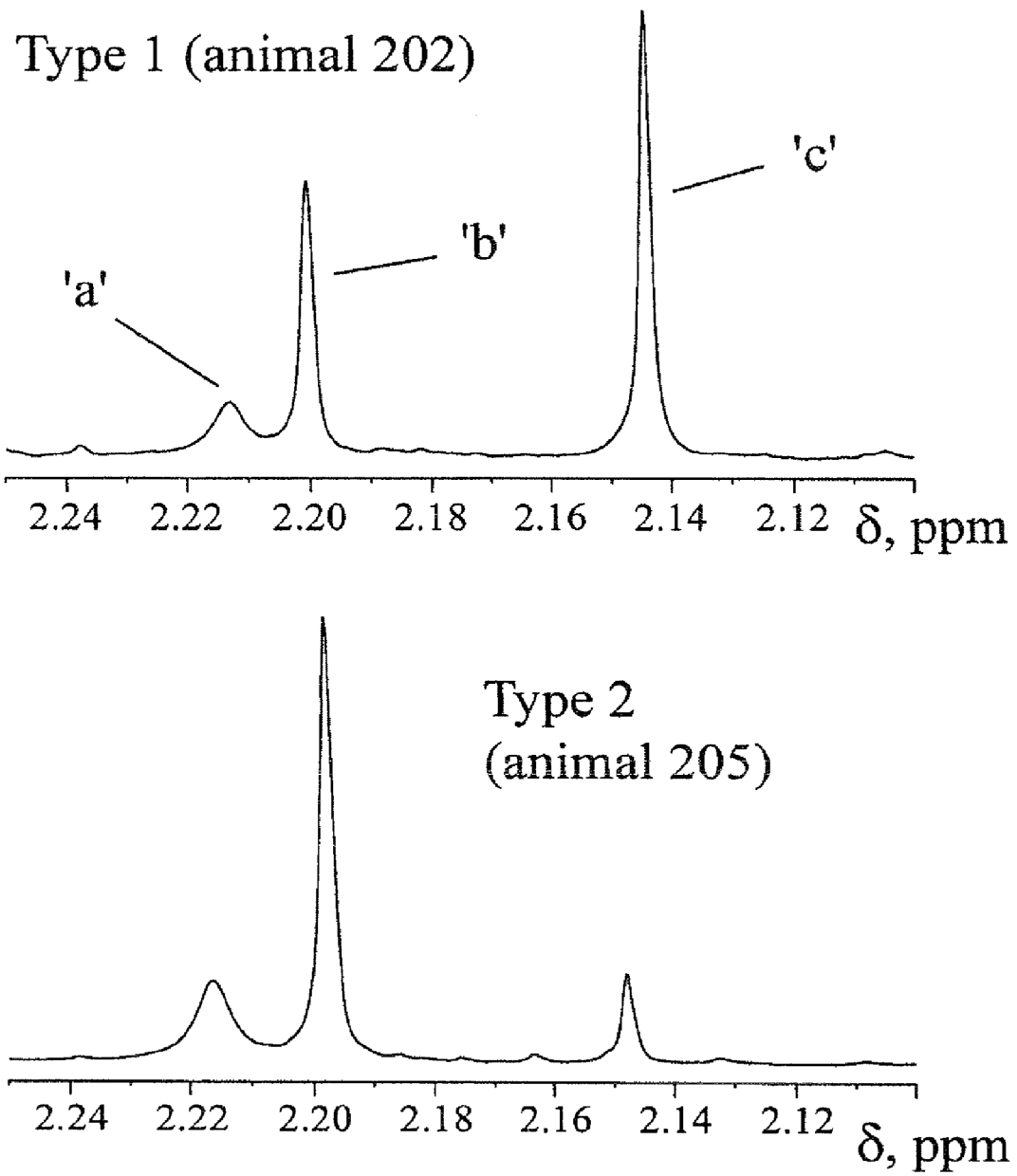
Figure 2.1

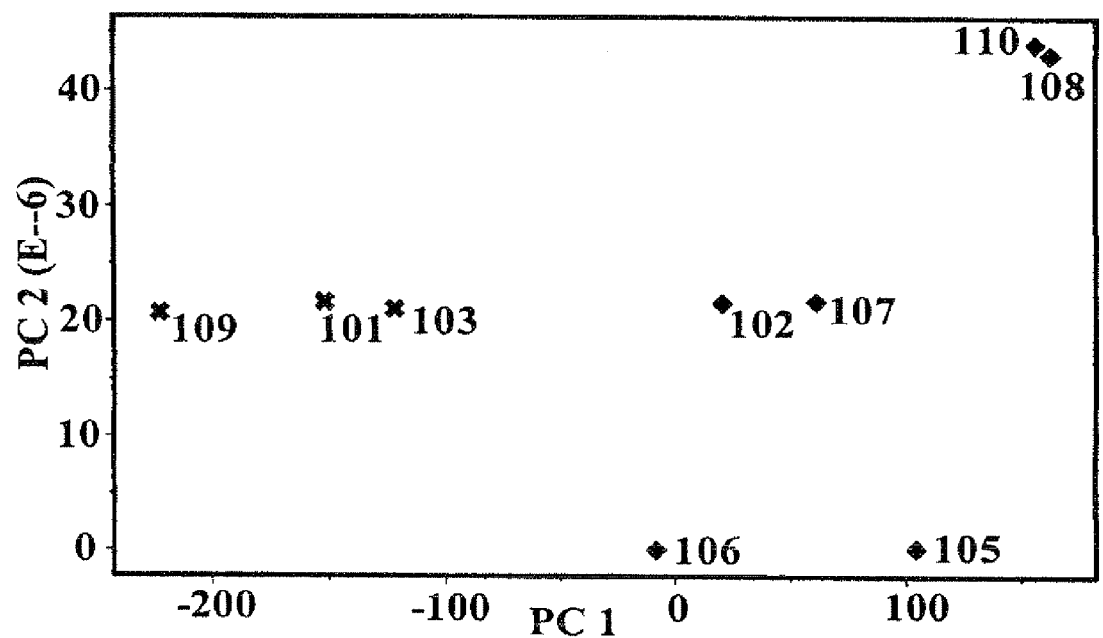
Figure 2.2

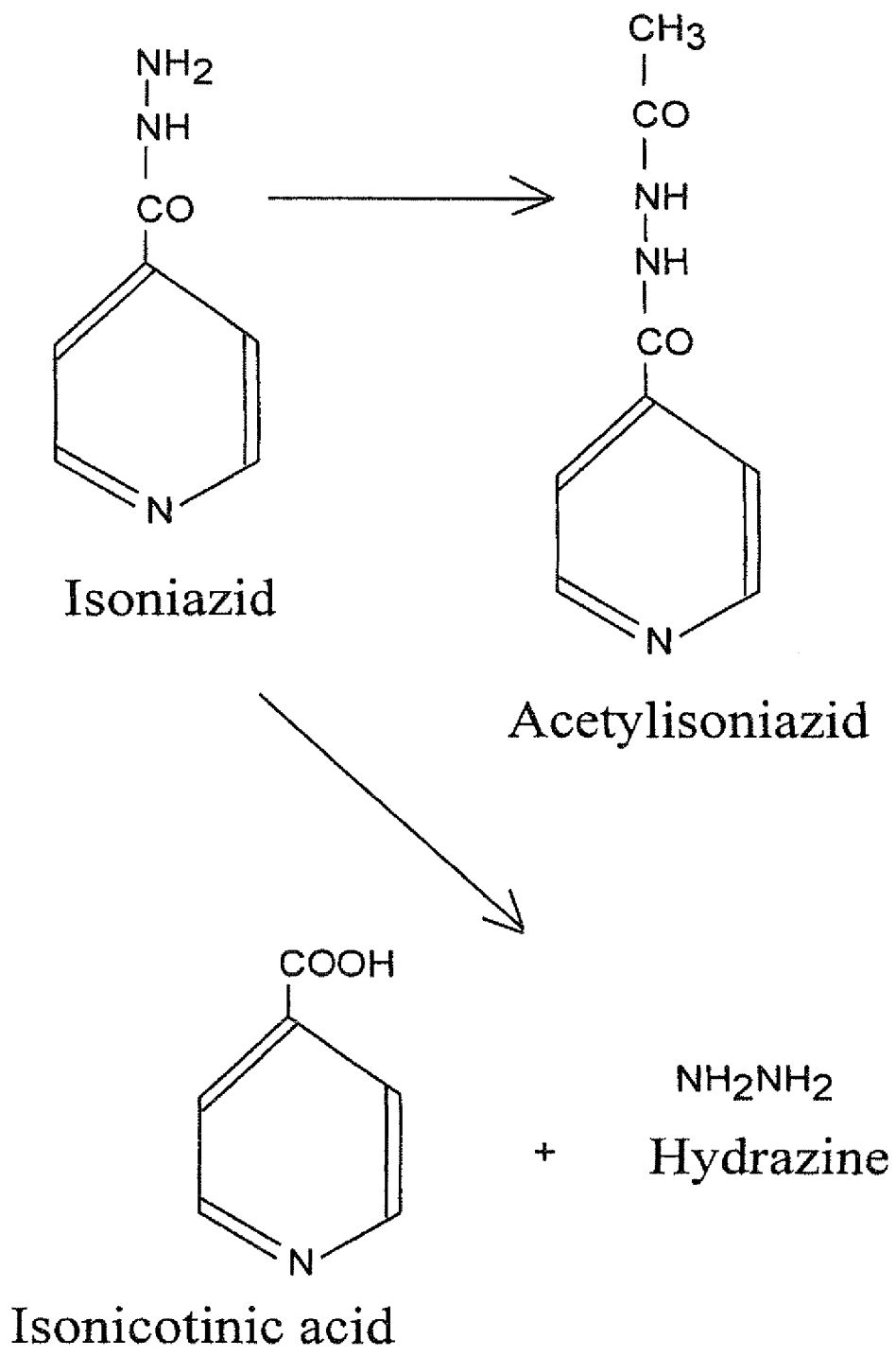
Figure 2.3

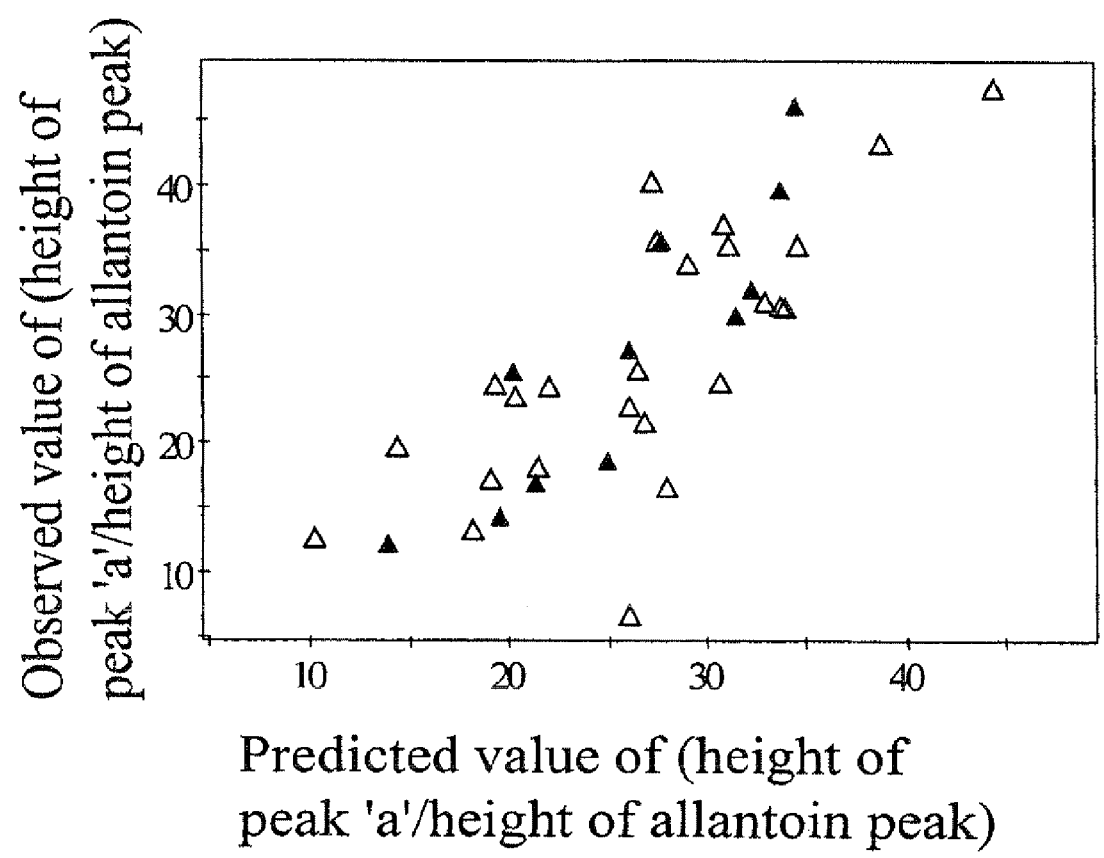
Figure 3.1

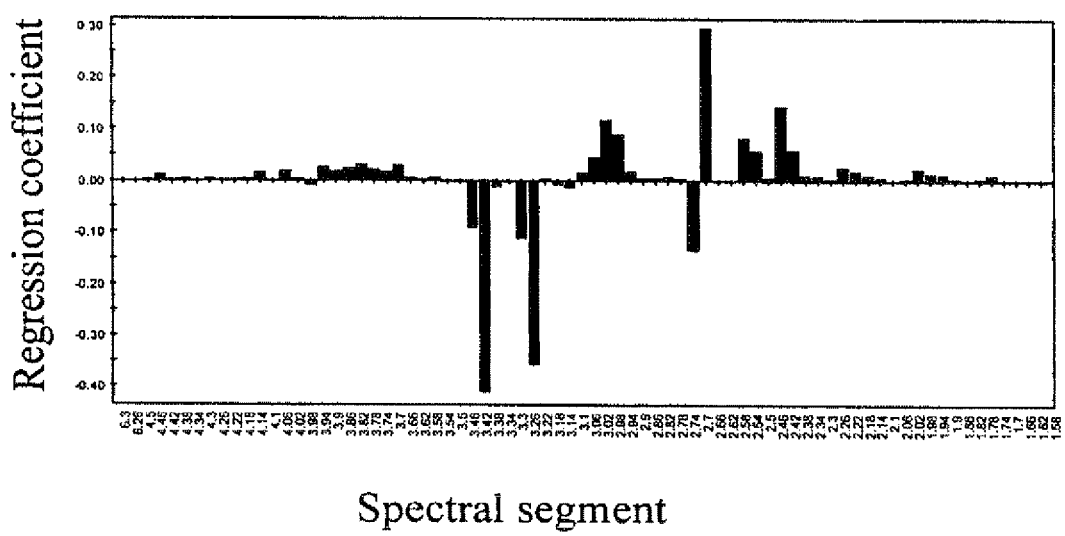
Figure 3.2

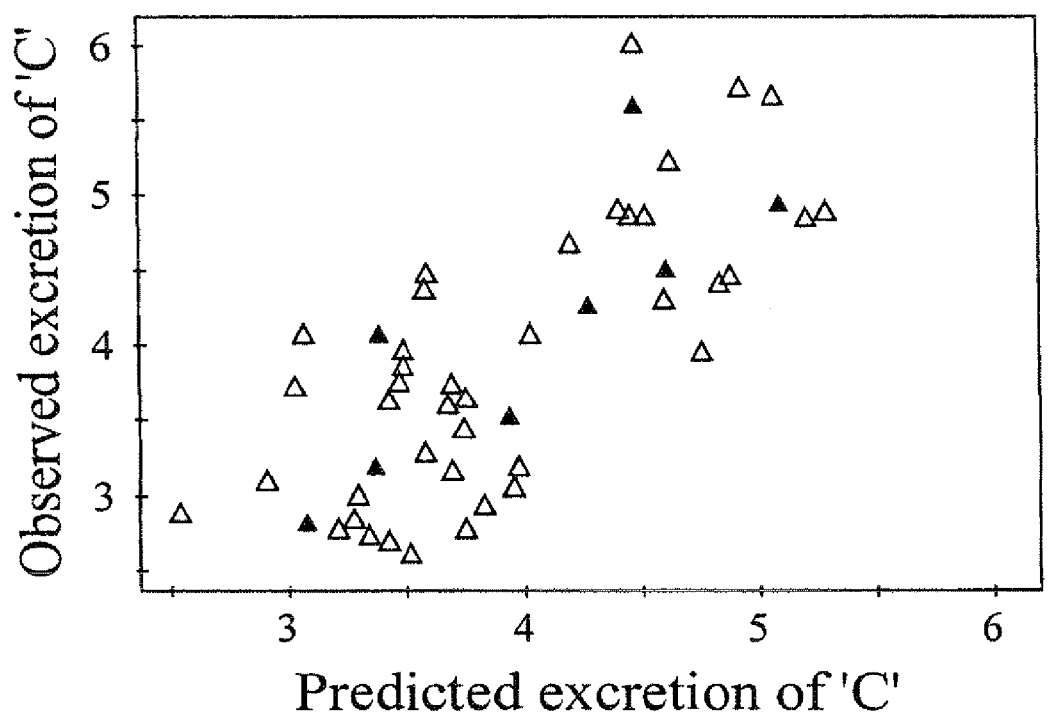
Figure 3.3

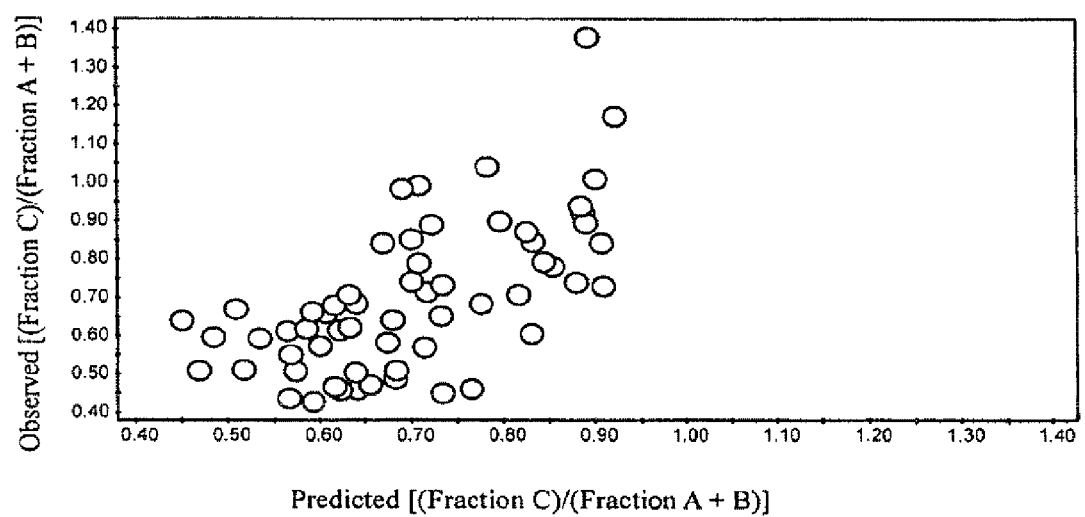
Figure 3.4

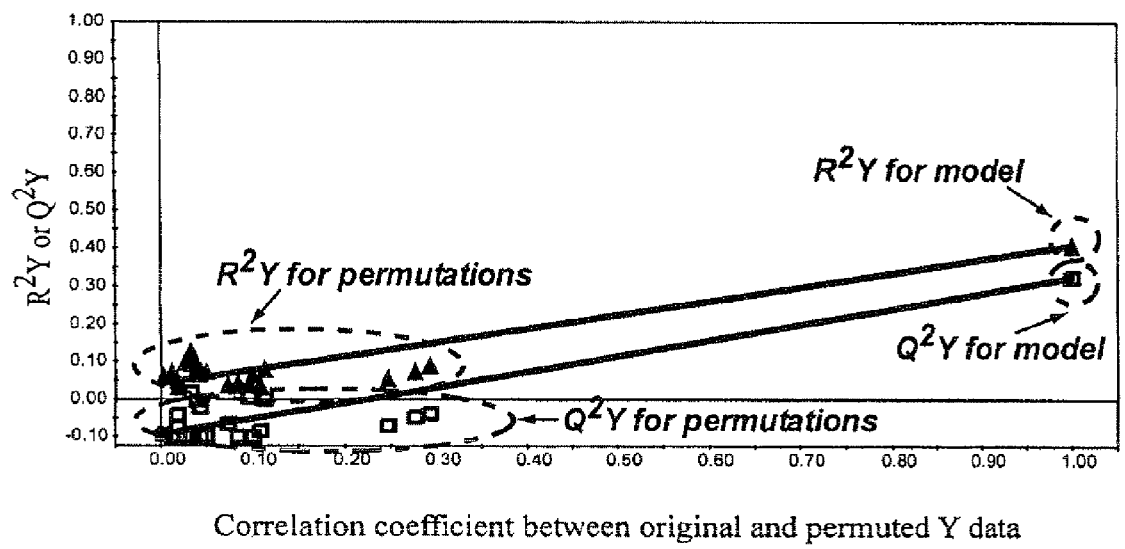
Figure 3.5

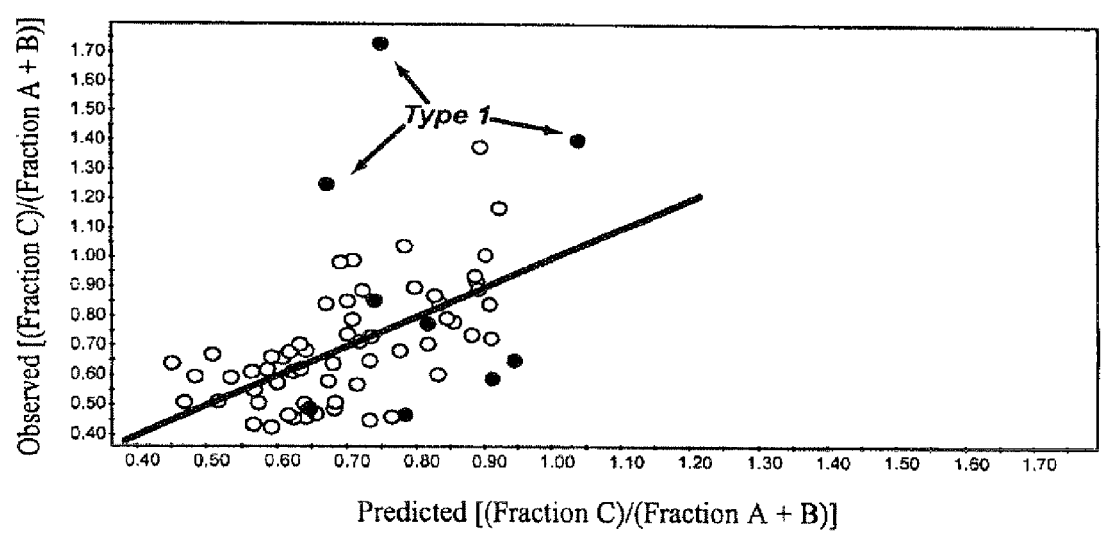
Figure 3.6

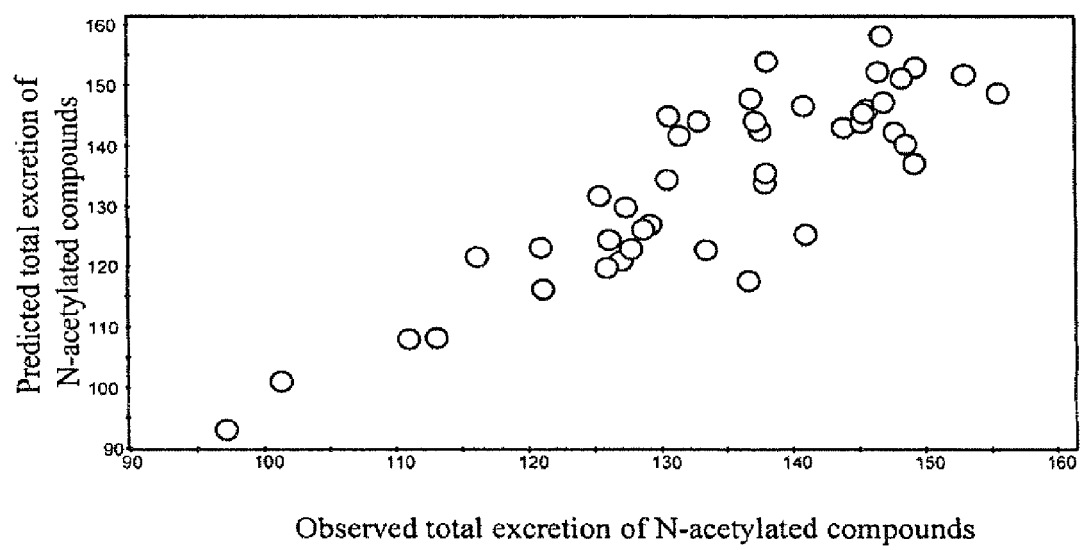
Figure 4.1

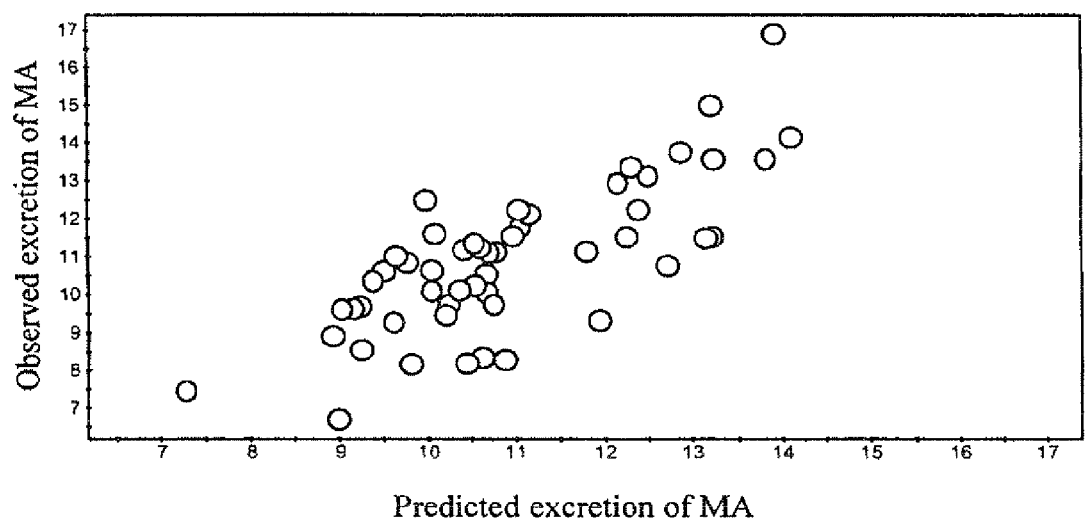
Figure 4.2

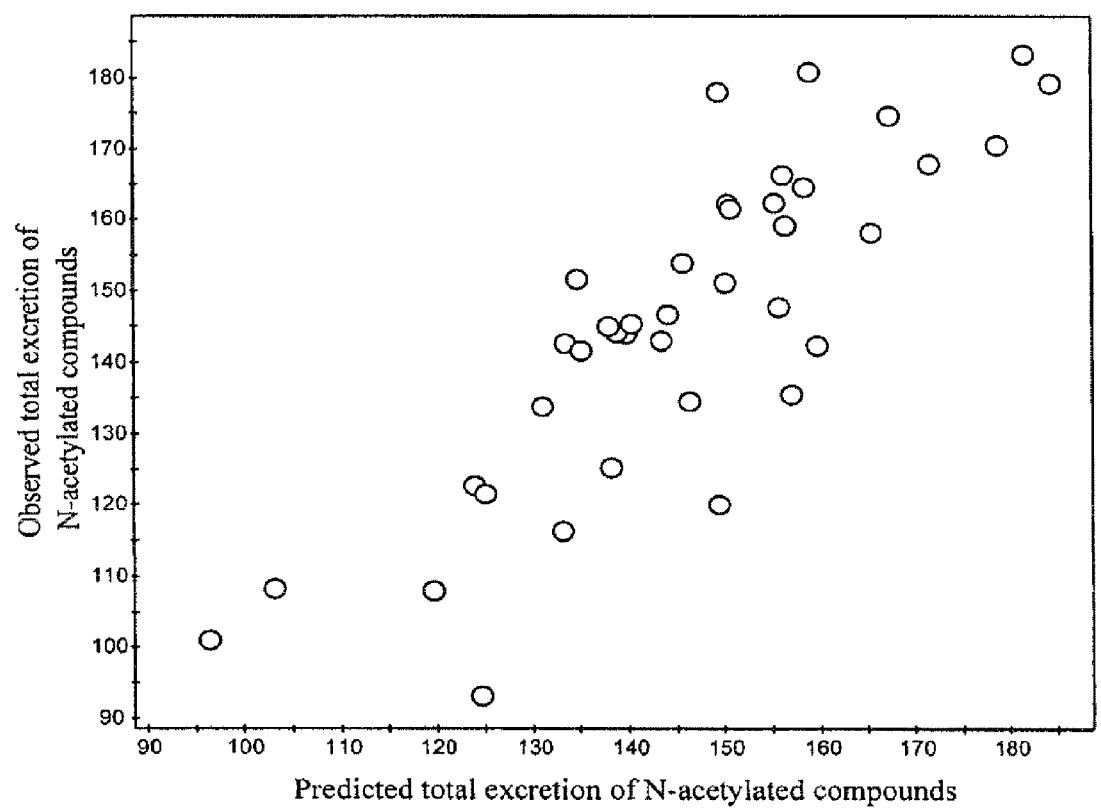
Figure 4.3

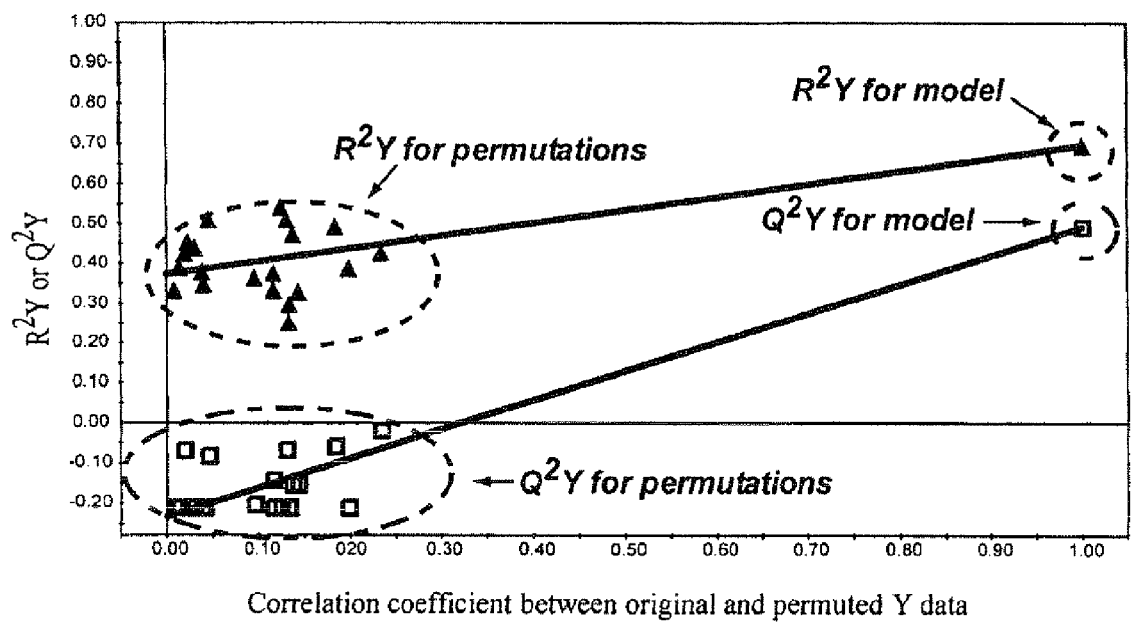
Figure 4.4

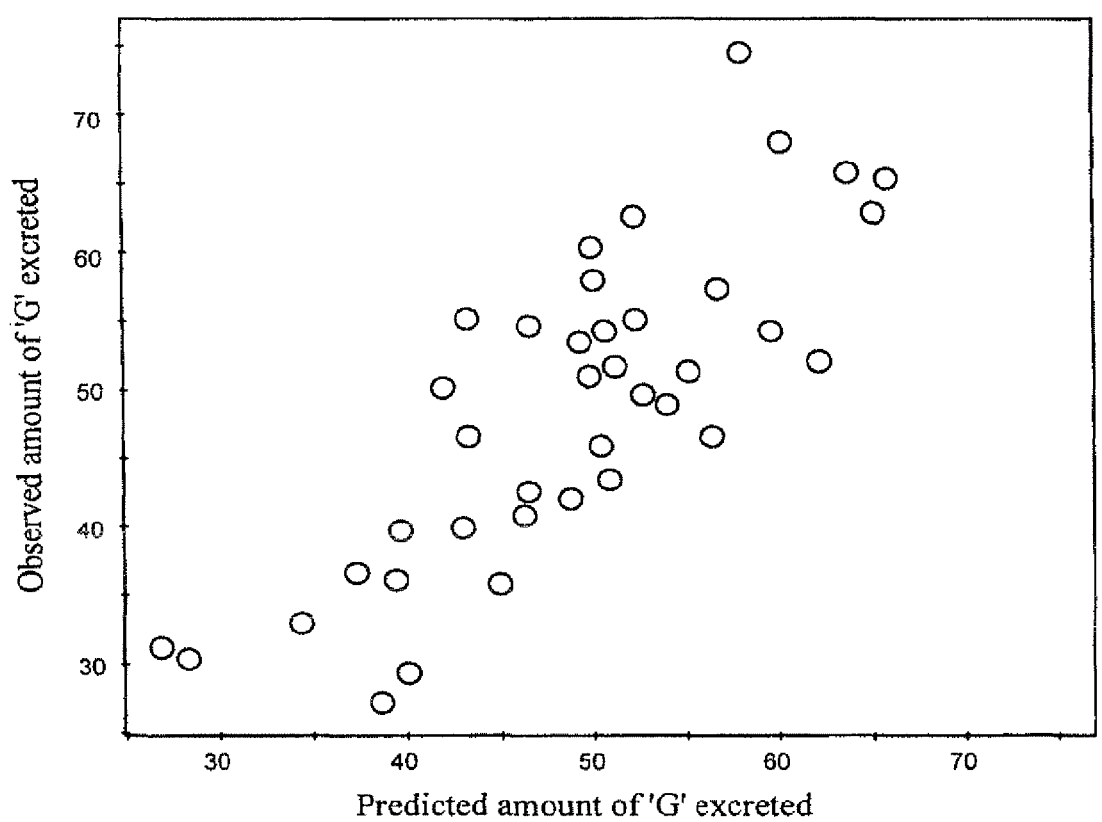
Figure 4.5

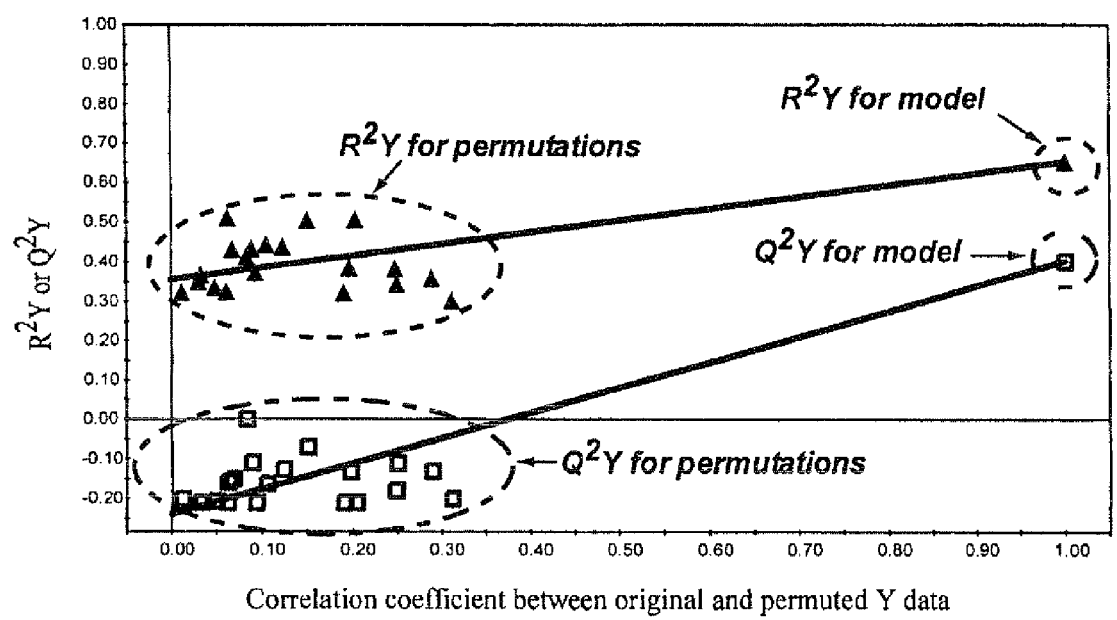
Figure 4.6

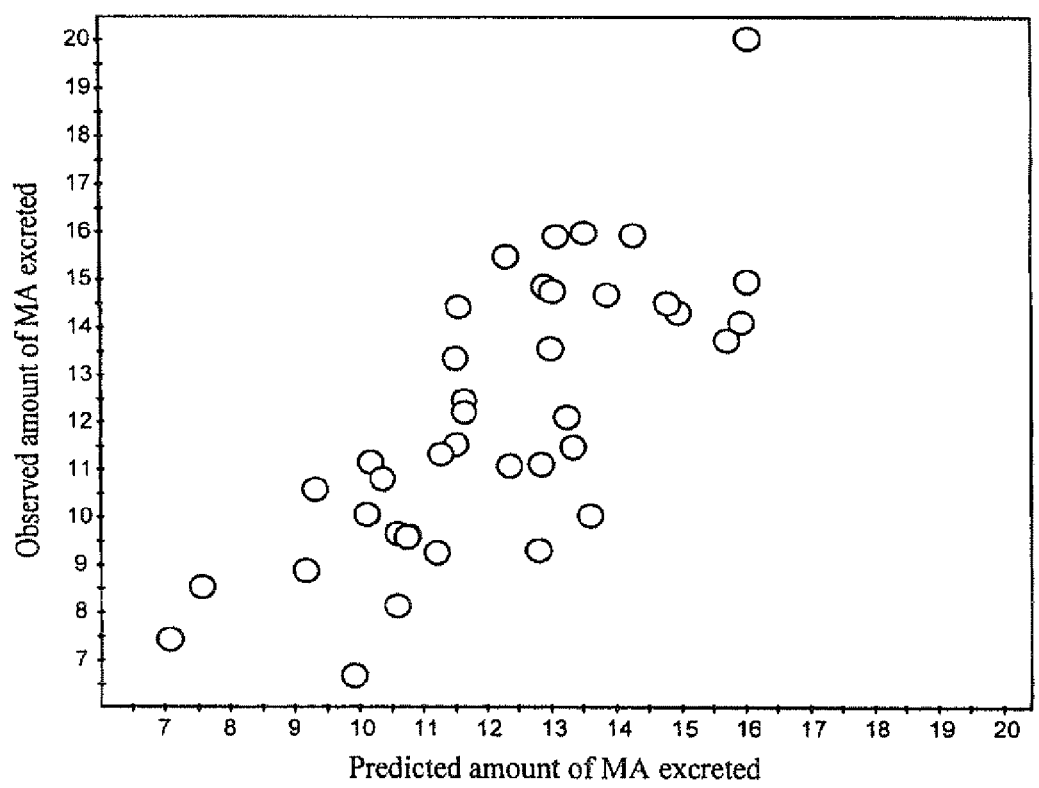
Figure 4.7

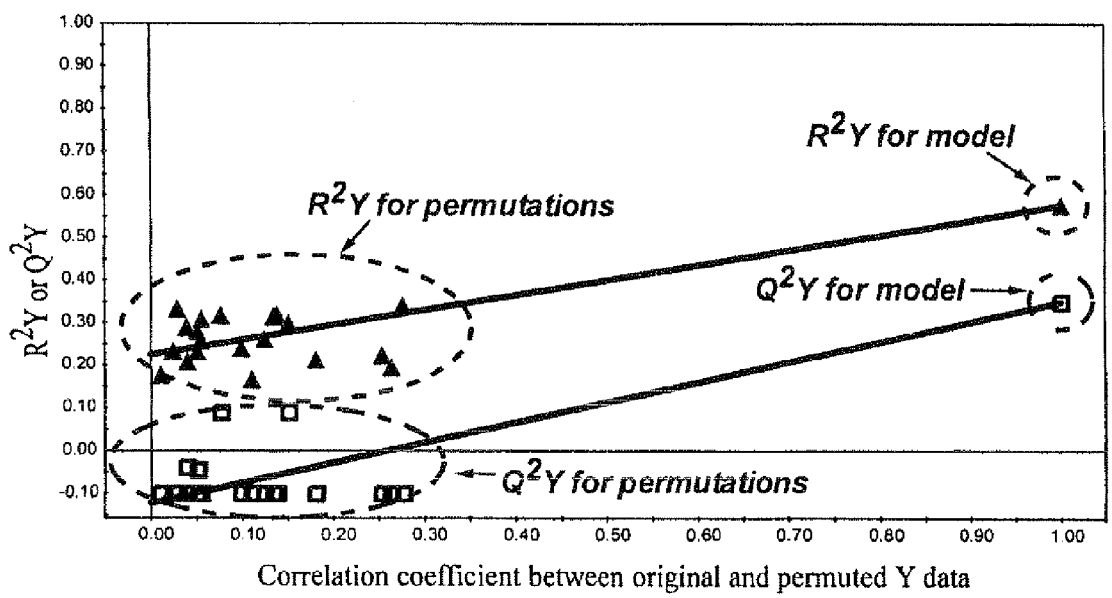
Figure 4.8

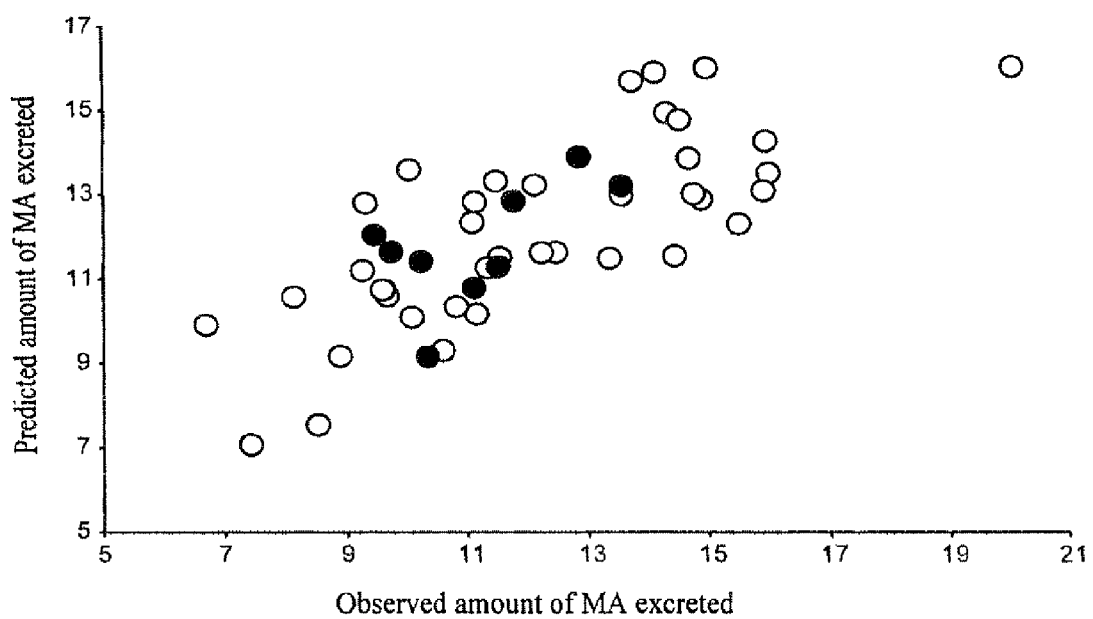
Figure 4.9

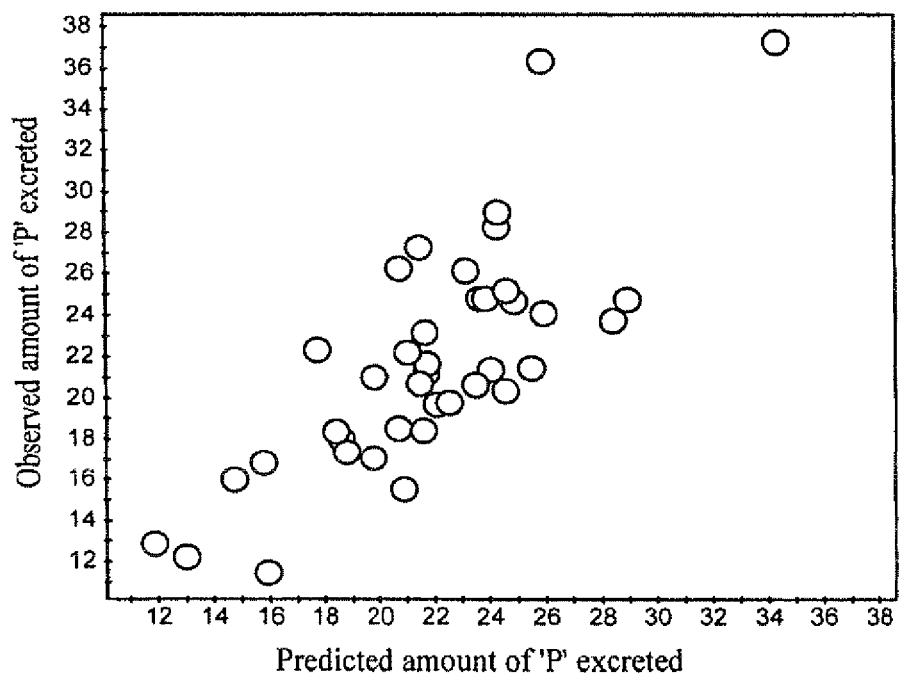
Figure 4.10

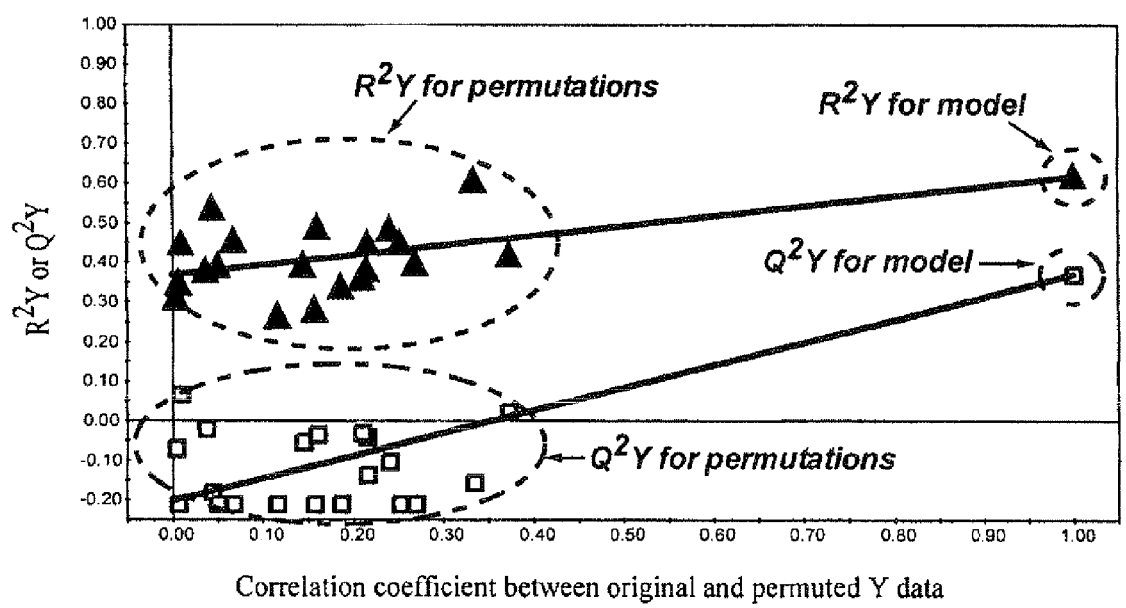
Figure 4.11

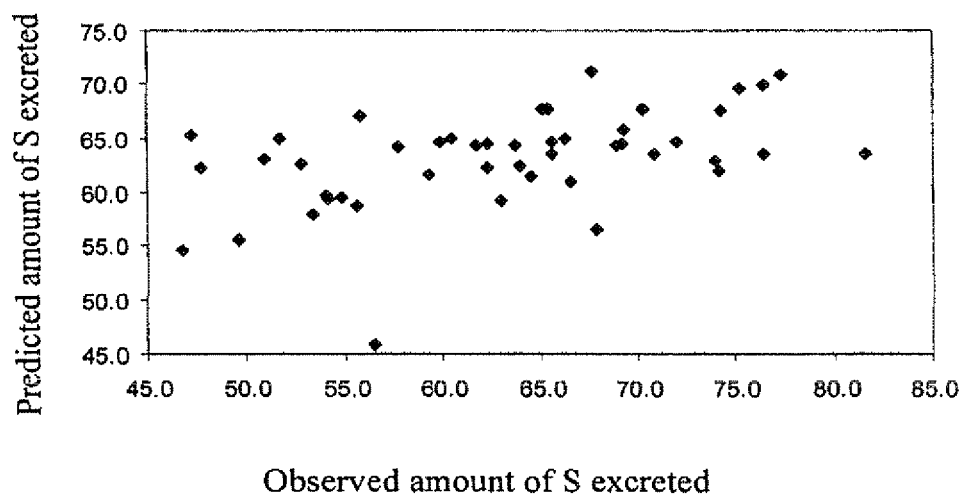
Figure 4.12

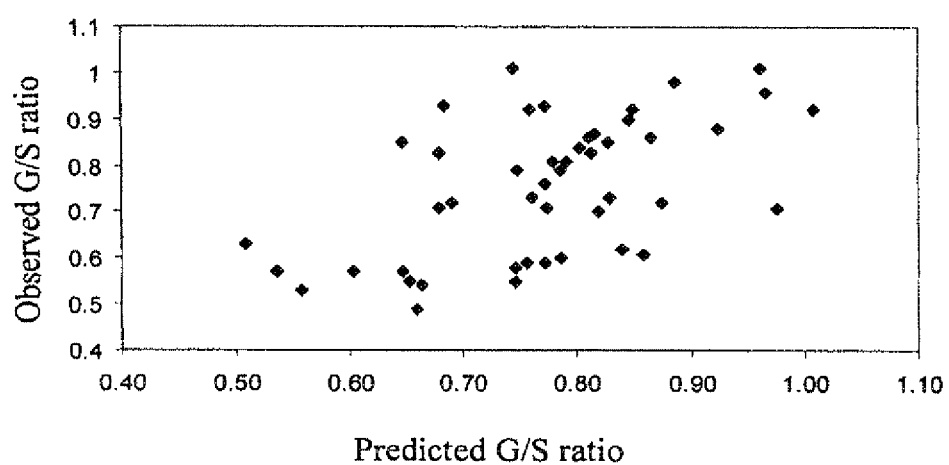
Figure 4.13

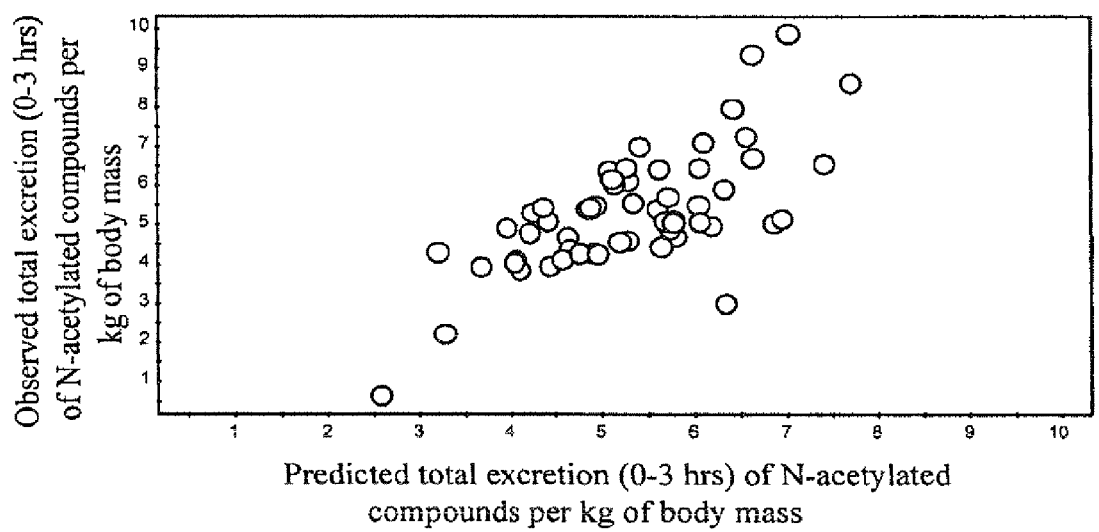
Figure 5.1

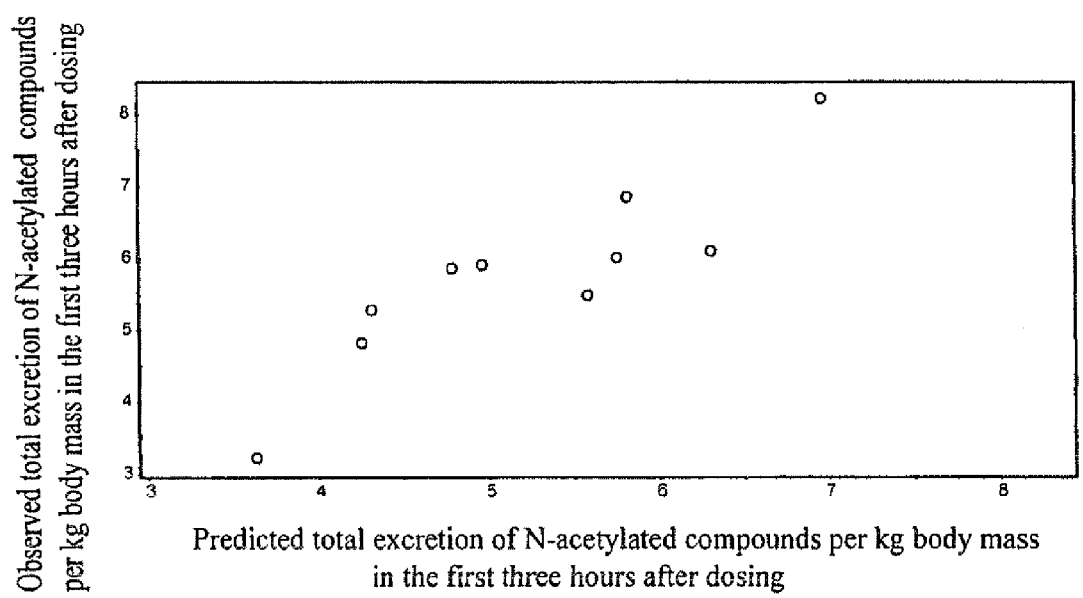
Figure 5.2

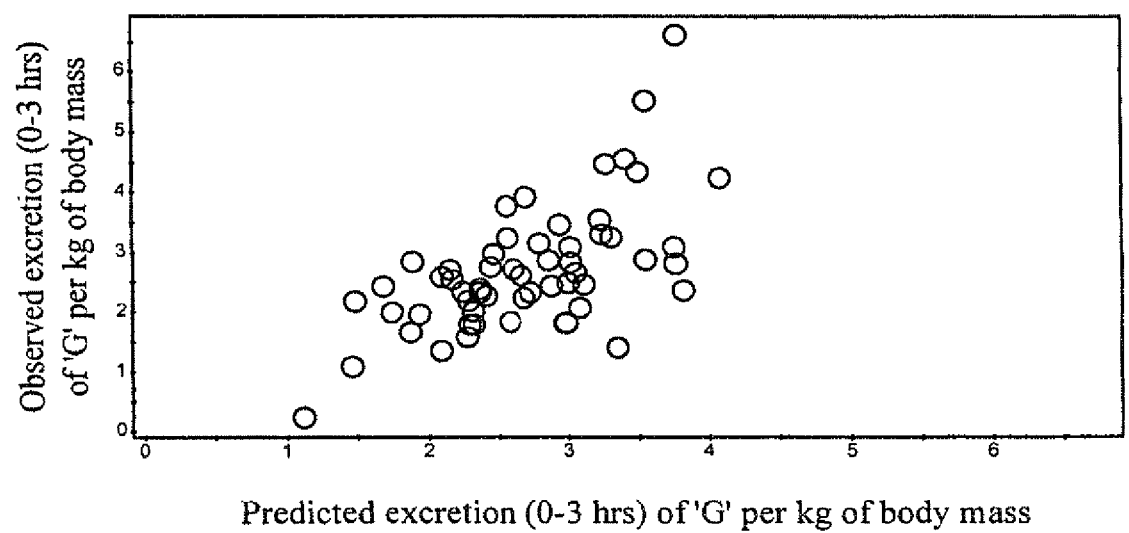
Figure 5.3

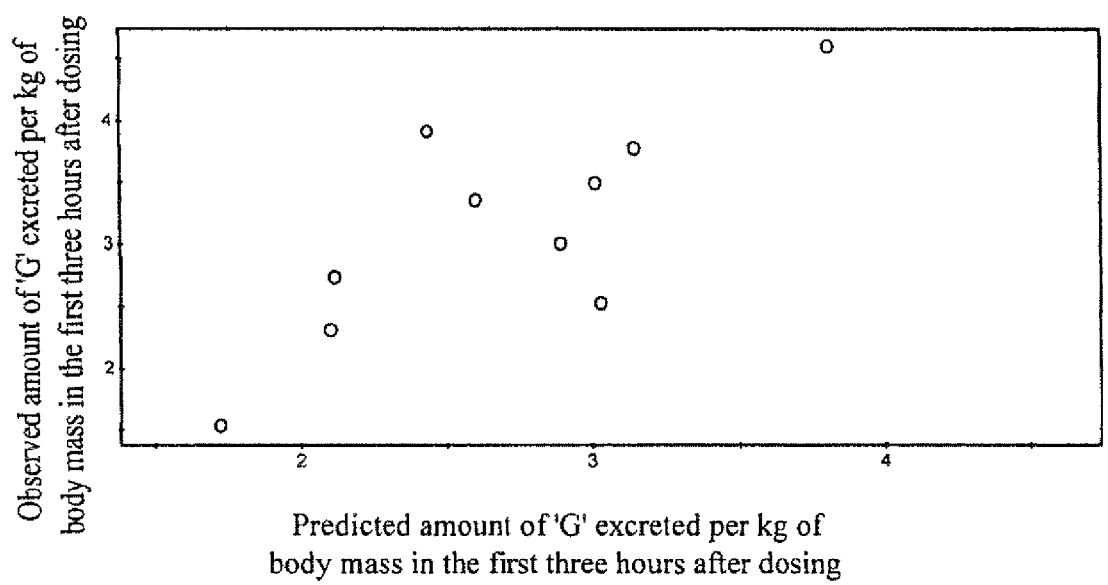
Figure 5.4

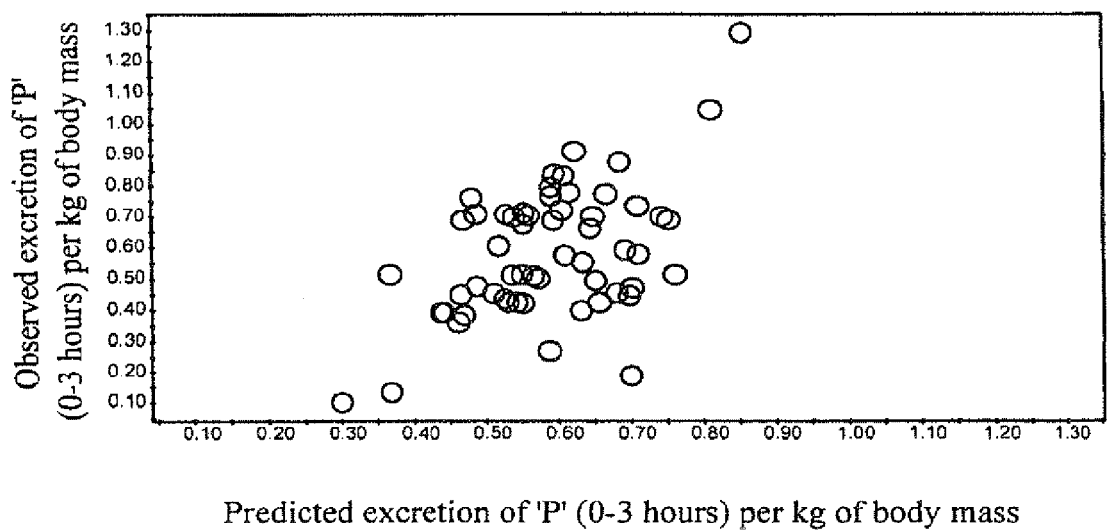
Predicted excretion of 'P' (0-3 hours) per kg of body mass
Figure 5.5

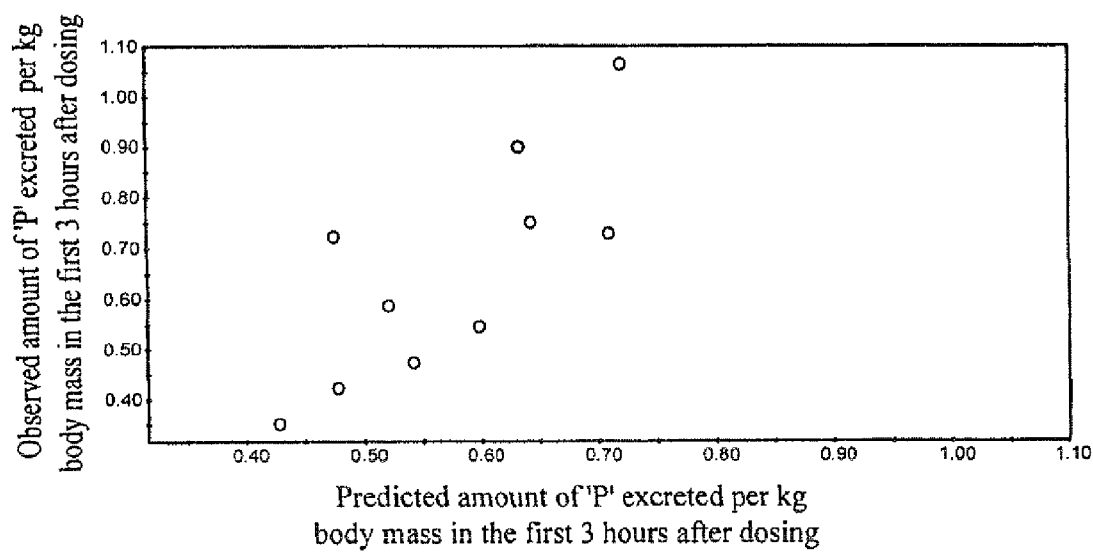
Figure 5.6

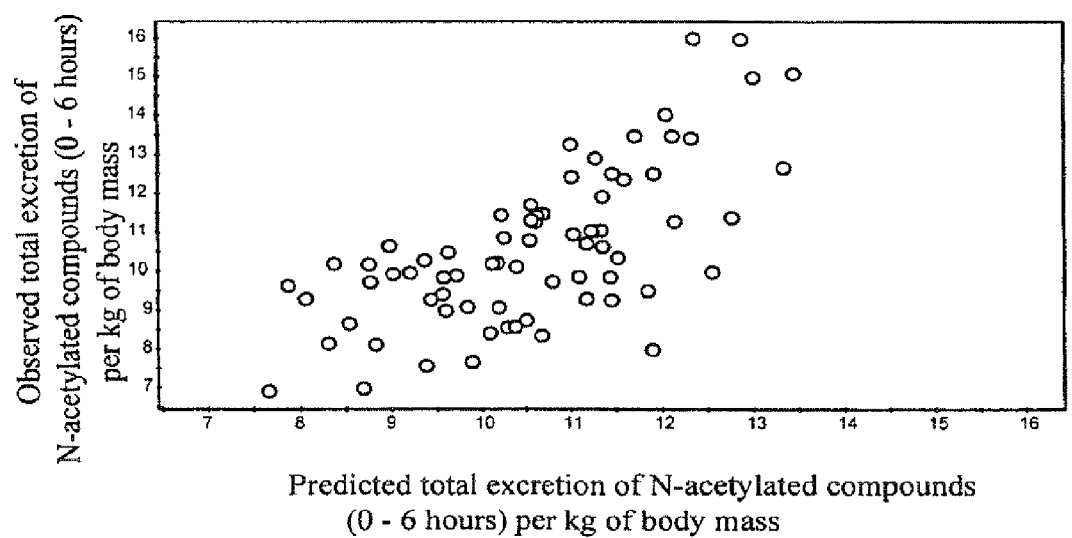
Figure 5.7

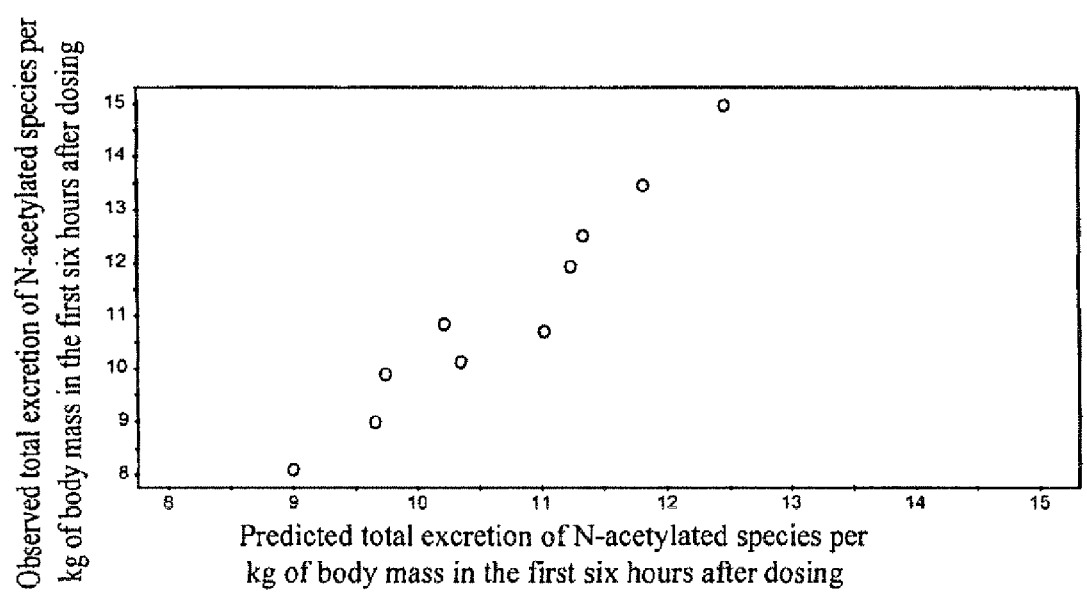
Figure 5.8

METABOLIC PHENOTYPING

CROSS REFERENCE TO RELATED APPLICATION

This patent application is a continuation application under 35 USC §120 of U.S. application Ser. No. 10/755,061, filed on Jan. 8, 2004 now abandoned, which is a continuation application under 35 USC §120 of PCT patent application serial number PCT/IB03/02309, filed Jun. 16, 2003, designating the United States, which claims priority to United Kingdom serial number 0213786.7, filed Jun. 14, 2002, and United Kingdom serial number 0213895.6 filed Jun. 17, 2002.

BACKGROUND

Biochemical Reactions

An organism's overall 'metabolic phenotype' is the sum total of its metabolic attributes and is determined by the interaction of its genetic composition and the 'environment', where the environment is considered in the widest possible sense. The term 'metabolic phenotype' may also be applied to individual aspects of an organism's metabolic characteristics.

A vast array of biochemical reactions (metabolic transformations) take place within living organisms and the overwhelming majority of these reactions are catalysed by enzymes.

Enzymes are specialised proteins that function as biochemical catalysts to accelerate biochemical reactions. Without enzymes many of the reactions required for normal cell activity would not proceed fast enough at normal bodily pH and temperature. As a catalyst, an enzyme increases the rate of a reaction but is recovered unchanged at the end of the reaction.

A molecule acted on by an enzyme is termed a 'substrate' and enzymes exhibit much specificity for particular substrates e.g. glucose oxidase will oxidise glucose but not galactose. This specificity is determined by the substrate-binding site on the enzyme surface. This site is a particular arrangement of amino acids that confers preferred binding ability for one or more substrates. Some enzymes have broad substrate specificity whereas others are specific to individual substances. Thus, for example, glucose, mannose and fructose are all phosphorylated by hexokinase whereas glucokinase is specific for glucose.

The International Union of Biochemistry and Molecular Biology (IUBMB) has established an enzyme classification system which has six major enzyme classes:

1. Oxidoreductases
2. Transferases
3. Hydrolases
4. Lyases
5. Isomerases
6. Ligases.

Each of these individual classes is further divided into sub-classes to which the individual enzymes belong. Full details are currently available on the world-wide web (www.chem.qmw.ac.uk/iubmb/enzyme).

As an example, guanidinoacetate N-methyl transferase (EC 2.1.1.2) catalyses the conversion of S-adenosyl-L-methionine and guanidinoacetate to S-adenosyl-L-homocysteine and creatine. This is an example of a methyl transferase.

Factors which may affect the rate of enzyme-catalysed reactions include the amount of substrate present, the amount of product present, the amount of the enzyme present and the activity of each enzyme molecule. The activity of an enzyme molecule can be affected by a variety of factors including its inherent activity, the presence of cofactors and prosthetic groups and by binding at an allosteric site. Both the amount of the enzyme and the activity per enzyme molecule may be affected by genetic variation between subjects. The amount of an enzyme and the activity per molecule combine to give the overall enzyme activity and this may vary considerably between different subjects. Such variation may independently affect a whole range of different enzymes and metabolic transformations and this variation will contribute to the generation of a different overall metabolic phenotype for each subject. Variation in the levels of any other substances that are required for biochemical transformations to take place will also contribute to the metabolic phenotype. For example, variation in the ability of subjects to effect drug glucuronidation may be caused by inter-subject variation in the level of UDP-glucuronic acid (UDPGA).

Whilst metabolic phenotype would typically be considered in terms of enzyme-catalysed reactions, metabolic phenotype in its broadest sense would also include measures relating to each of the non-enzymic reactions that might occur within a certain type of subject. Additionally, a subject's overall metabolic phenotype would be influenced by the nature and quantity of the other organisms, such as the gut bacteria, that are living within or on that subject. Importantly, whilst a subject's genotype would be constant throughout the life of that subject, a subject's overall metabolic phenotype could change significantly with age and with other 'environmental' influences such as disease, infection and nutritional status.

Variation in metabolic phenotype causes inter-subject differences in the metabolism of xenobiotics such as drugs. Such differences in metabolism are a major factor contributing to differential responses (e.g. degree of efficacy, degree of toxicity etc.) to dosed substances because they may result in different degrees of exposure to the active substance(s). Thus, for instance, fast metabolism of a toxic substance to non-toxic metabolites would result in rapid detoxification whilst slow metabolisers of the toxin would be more likely to show toxic effects. Conversely, fast metabolism of the efficacious component or derivative of a drug could lead to reduced efficacy of the treatment. Other factors contributing to differential responses to dosed substances include inter-subject differences in absorption from the gut and differential sensitivity of receptors. Genetic variability in susceptibility and response to toxicants was reviewed in Toxicology Letters (2001) Vol 120 in articles entitled "Genetic variability in susceptibility and response to toxicants" by Ingelman-Sundberg (pages 259-268) and by Miller et al (pages 269-280). Inter-individual variability in human drug metabolism is the subject of a book "Interindividual Variability in Human Drug Metabolism" edited by Pacifici and Pelkonen and published by Taylor & Francis (2001).

Body Fluids and the Effects of Variation in Metabolic Phenotype

Aspects of the biochemical composition of intracellular fluids are reflected in the extracellular tissue fluid and consequently in the circulating blood which contacts that tissue. Thus, alterations in the biochemical composition of cell fluids are liable to affect the biochemical composition of the extracellular tissue fluid and the biochemical composition of the blood. Alterations in blood composition may, in turn, be reflected in altered urinary composition. Thus, abnormal cellular metabolic processes are likely to be reflected in altered compositions of biofluids such as blood and urine and, consequently, these fluids provide diagnostic windows onto the state of the body. Major alterations in such fluids are frequently caused when toxins, such as liver or kidney toxins, are administered and inherent factors such as major enzyme deficiencies can also be identified from those fluids. Thus, for example, in classical phenylketonuria, a deficiency in phenylalanine hydroxylase causes a failure to convert phenylalanine to tyrosine and produces an altered urinary composition with increased levels of phenylpyruvic acid, phenyllactic acid and phenylacetic acid (see Textbook of Biochemistry With Clinical Correlations, 4th Edition, 1997, edited by T. M. Devlin, published by Wiley-Liss). This is an example of a genetically determined error of metabolism and such diseases are known as 'inborn errors of metabolism' (see, for example, Newsholme and Leech, 1983, Biochemistry for the Medical Sciences, published by John Wiley and Sons) Identification of the described urinary changes serves to identify the enzymic deficiency.

As well as the serious metabolic deficiencies, other lesser inter-individual differences in metabolic phenotype exist that are not sufficient to cause disruption of normal metabolic processes and consequent disease. However, such differences may be revealed when the organism is subjected to an unusual challenge such as a large dose of a particular chemical compound e.g. a drug substance. Additionally, such differences may cause altered risk factors for diseases such as cancer which are associated with long term exposure to harmful substances such as environmental pollutants and tobacco smoke.

NMR Spectroscopic Analysis of Biological Samples

The use of Nuclear Magnetic Resonance (NMR) spectroscopy to study the low molecular weight composition of biological fluids is now well established (e.g. Nicholson and Wilson (1989), High resolution proton magnetic resonance spectroscopy of biological fluids, Progress in NMR Spectroscopy, 21, 449-501; Lindon et al. (1999), NMR spectroscopy of biofluids, Annual reports on NMR spectroscopy, 38). The advent of high field magnets for NMR has been one factor in this development. Such magnets have greatly improved the sensitivity of the technique and the use of cryoprobes brings further improvement. An additional benefit, for the examination of complex mixtures, is that increased magnetic field strength leads to improved dispersion of the NMR signals i.e. the signals are more spread out and less prone to overlap one another. Other factors which have greatly improved the capabilities of modern NMR spectroscopy include improvements in probe design leading to much higher sensitivity, the ready availability of computing power and the development of improved pulse sequences e.g. for the selective suppression of the water signal in an aqueous sample. The advent of flow probes has enabled greatly increased sample throughput in comparison to the conventional use of high precision, fragile glass sample tubes.

In addition to its usefulness for biofluids, NMR spectroscopy can be successfully used for the examination of small (ca. 10-20 mg) samples of solid tissue (e.g. Moka et al. (1997), Magic angle spinning proton nuclear magnetic resonance spectroscopic analysis of intact kidney tissue samples, Analytical Communications, 34, 107-109). However, this requires a special technique known as Magic Angle Spinning (MAS) and, in comparison to solution state NMR spectroscopy, MAS-NMR spectroscopy is a time-consuming procedure. With automated solution state NMR spectroscopy it is possible to examine more than 150 samples per day whilst 10 samples per day is typical for MAS-NMR spectroscopy where the samples are manually changed by an operator.

The vast majority of organic compounds contain protons that would be detectable by $^1$H NMR spectroscopy so long as enough of the compound is present in the sample being analysed. This means that, in principle, $^1$H NMR spectroscopy is an almost universal detector for organic compounds. The detectability of $^1$H NMR spectroscopic signals from a particular sample component depends on the amount of the component present, on the type and molecular environment of the proton(s) and on the nature of the NMR experiment. The main limitation is that exchangeable protons, such as those in hydroxyl groups, may not be observed. Essentially, the $^1$H NMR spectrum of any particular organic compound is unique to that compound. Additionally, NMR spectra are readily interpretable and predictable so that structural features and often the complete structure of a compound may be deduced from its $^1$H NMR spectrum.

In the conventional one-dimensional (1D) $^1$H NMR spectrum of a biofluid the individual spectra of all the detectable components are superimposed according to their relative concentrations and this facilitates quantitation. In practice, the high field $^1$H NMR spectra of biofluids such as urine and plasma are extraordinarily rich in information, with a very large number of low-to-medium molecular weight components being detectable in a single experiment. Lipoproteins and high molecular weight components such as proteins are also present in plasma but their $^1$H NMR spectra are subject to signal broadening influences arising from restricted mobility of the resonating nuclei. Such broadening reduces the amount of information derivable from and about such components.

Applications of Biofluid NMR Spectroscopy

In comparison to NMR spectroscopy, traditional clinical chemistry assays generally provide more exact quantitation and may also provide better detection limits. On the other hand, $^1$H NMR spectroscopy has a major advantage over traditional clinical chemistry in that, by the former, the levels of all the detectable components are measured in a single experiment without the need to specify which components require analysis. Thus, by $^1$H NMR spectroscopy, unexpected changes may be observed and previously unrecognised substances may be identified. Thus, $^1$H NMR spectroscopy has great strength as a simultaneous multi-analyte detector for non-routine investigations and is ideally suited to the detection of new biomarkers.

The analysis of post-dose body fluids using NMR spectroscopy to identify and track responses to toxins is known (e.g. Holmes et al. (1992) NMR spectroscopy and pattern recognition analysis of the biochemical processes associated with the progression and recovery from nephrotoxic lesions in the rat induced by mercury (II) chloride and 2-bromoethanamine, Mol. Pharmacol., 42, 922-930). In the context of toxicology studies, biofluid NMR spectroscopy may detect metabolites of dosed substances and/or changes in endogenous biofluid components that are induced by dosed substances and may be used to assess toxic effects and to identify relevant defensive processes, such as glucuronidation and mercapturic acid formation. Biofluid NMR spectroscopy also has significant potential to elucidate mechanisms of toxicity.

It is known that, using NMR spectroscopy, certain inborn errors of metabolism can be readily identified from biofluid samples (e.g. Moolenaar et al. (2003) Proton nuclear magnetic resonance spectroscopy of body fluids in the field of inborn errors of metabolism, Ann. Clin. Biochem., 40, 1, 16-24). It is also known that NMR spectroscopy of biofluids can be used to diagnose other disease conditions and to track responses to therapy.

Following the success of the NMR-based approach to monitoring the metabolic state of living systems the term 'metabonomics' has been coined (Nicholson et al. (1999), 'Metabonomics': understanding the metabolic responses of living systems to pathophysiological stimuli via multivariate statistical analysis of biological NMR spectroscopic data, Xenobiotica, 29, 1181-1189). Metabonomics is defined as 'the quantitative measurement of the multiparametric metabolic response of living systems to pathophysiological stimuli or genetic modification'. Metabonomics is complementary to the genomics and proteomics technologies which are based on detecting changes in gene expression and protein levels respectively. An advantage of metabonomics in relation to the other technologies is that metabonomics looks at the overall metabolic result rather than at underlying influences which may or may not be metabolically significant.

Pattern Recognition

A complicating factor in extracting useful biochemical information from sets of biological (biofluid or tissue-derived) NMR spectra is their great complexity. An efficient way to investigate these complex multiparametric data sets is to employ computer-based pattern recognition methods.

Pattern recognition (PR) is a general term for methods of multivariate data analysis which may be used to look for patterns in data sets, a priori, or to look for elements of data sets which correlate with other known factors (see, for example, Beebe et al., 1998, Chemometrics, A Practical Guide, John Wiley and Sons, New York etc.). Inherent in this is the assumption that the data set consists of a number of different objects for which a variety of parameters (or 'variables') have been measured. Whatever those parameters may be, the same parameters have generally been measured on all the objects in the data set although occasional missing values may be acceptable. In the context of a set of NMR spectra, the different objects would be the different spectra whilst the various parameters would generally be the integrations for different spectral windows within the overall spectrum. PR methods may be conveniently classified as 'supervised' or 'unsupervised' and some of these multivariate statistical analysis methods are described in the following sections.

Unsupervised PR Methods

Unsupervised PR methods are used to determine inherent clustering patterns in multivariate data sets without reference to any other independent knowledge. Examples of unsupervised pattern recognition methods include principal component analysis (PCA), hierarchical cluster analysis (HCA), and non-linear mapping (NLM).

Principal Components Analysis (PCA)

Principal components analysis (PCA) (e.g. Sharaf et al., 1986, Chemometrics, J. Wiley and Sons, New York) is one of the most useful and easily applied unsupervised PR techniques. Principal components (PCs) are latent variables created from linear combinations of the starting variables with appropriate weighting coefficients. The properties of these PCs are such that: (i) each PC is orthogonal to (i.e. uncorrelated with) all other PCs, and (ii) the first PC contains the largest part of the variation of the data set (information content) with subsequent PCs containing correspondingly smaller amounts of variation.

In mathematical terms, a data matrix, X, can be regarded as being composed of a 'scores' matrix, T, and a 'loadings matrix', P, such that $X=TP^t$, where the superscript 't' denotes the transpose. The covariance matrix, C, is calculated from the data matrix, X. The eigenvalues and eigenvectors of the covariance matrix are then determined by diagonalisation. The coordinates of the different objects in eigenvector plots (the principal components or PCs) are denoted 'scores' and comprise the scores matrix T. The eigenvector coefficients are denoted 'loadings' and comprise the loadings matrix P, and give the contributions of the descriptors to the PCs.

A plot of the any two principal component scores is often called a 'scores plot'. The scores plot for PC1 vs. PC2 provides the maximum information content of the data in two dimensions although lower order PC plots may well be useful. Such scores plots can be used to visualise inherent clustering in data sets.

Supervised Methods

Where appropriate, supervised pattern recognition methods may also be used to analyse multivariate data. In such analyses the data set (X) is related, where possible, to one or more known factors (Y) such as class membership or the value of one or more parameters outside the X data set. In such methods a 'training set' of X and Y data is used to construct a statistical 'model' that estimates the required Y factor(s) from the X data. This model is then tested with independent data (referred to as a validation data set) to determine its robustness and predictive ability. Once validated the model may legitimately be used to predict the relevant Y factors for samples where only the X data is available.

Examples of supervised pattern recognition methods include the following: soft independent modelling of class analysis (SIMCA); partial least squares analysis (PLS); linear descriminant analysis (LDA); K-nearest neighbour analysis (KNN); artificial neural networks (ANN); probabilistic neural networks (PNNs); rule induction (RI); and Bayesian methods. See, for example: (re. SIMCA) Wold (1976) Pattern recognition by means of disjoint principal components models, Pattern Recog., 8, 127; (re. PLS) Frank et al. (1984) Prediction of product quality from spectral data using the partial least squares method, J. Chem. Info. Comp., 24, 20; (re. LDA) Nillson, 1965, Learning Machines, McGraw-Hill, New York); (re. KNN) Beebe et al., 1998, Chemometrics, A Practical Guide, John Wiley and Sons, New York etc; (re. ANN) Anker and Jurs (1992) Prediction of C-13 nuclear magnetic resonance chemical shifts by artificial neural networks, Anal. Chem., 64, 1157; (re. PNN) Speckt (1990) Probabilistic neural networks, Neur. Networks, 3, 109; (re. RI) Quinlan (1986) Induction of decision trees, Machine Learning, 1, 81; (re. Bayesian Methods) Bretthorst, 1990, An introduction to parameter estimation using Bayesian probability theory, In: Maximum Entropy and Bayesian Methods, Ed. Fougere, Kluwer Academic Publishers, The Netherlands, 53-79.

Partial Least Squares (PLS)

PLS is the regression extension of the PCA method described earlier. In PLS the variation between the objects in a data matrix X is described by the X-scores, T, and the variation in the Y-block regressed against is described in the Y-scores, U. Essentially, what PLS does is to maximize the covariance between T and U. For the PLS model a set of PLS weights, W, are calculated, containing the influence of each X-variable on the explanation of the variation in Y. The corresponding set of weights for the Y-block is designated C. A matrix of X-loadings, P, is also calculated. These loadings are used both for interpretation and to perform the proper decomposition of X.

The PLS decomposition of X and Y can hence be described as follows:

$$X = TP^t + E$$

$$Y = TC^t + F$$

where E and F are the X and Y residuals respectively and the superscript 't' denotes the transpose of the relevant matrix.

The PLS regression coefficients, B, are then given by:

$$B = W(P^tW)^{-1}C^t$$

The estimate of Y, $Y_{est}$, can then be calculated according to the following formula:

$$Y_{est} = XW(P^tW)^{-1}C^t = XB$$

Partial Least Squares Descriminant Analysis (PLS-DA)

PLS-DA is a supervised multivariate method yielding 'latent' variables in a data matrix (X) that describe the maximum separation between known classes of objects (Y). PLS-DA is based on PLS which is the regression extension of the PCA method described earlier. Whereas PCA simply works to find the maximum variation existing within the variables describing the studied objects, PLS-DA works to find the maximum separation between known classes of objects. This is done by a PLS regression against a 'dummy' vector or matrix (Y) carrying the class information. The calculated PLS components are thereby focussed on describing the variation in X that separates the classes (Y), if this information is present in the data. The class membership has to be known prior to the actual modelling. Once a model is calculated and validated it can legitimately be used for prediction of class membership for objects of unknown class.

Neural Networks vs. PLS and PLS-DA

Methods such as PLS and PLS-DA rely on the extraction of linear associations between the input variables and this can significantly limit the power of the analysis. Neural network-based pattern recognition techniques can provide improved predictive ability, particularly where the factor being predicted is influenced by a number of unrelated causes. Nevertheless, methods such as PLS and PLS-DA are often sufficiently powerful and provide a significant benefit over relatively 'black box' neural network methods in that they readily allow some information to be gained as to what aspects of the input dataset were particularly important in the model building i.e. in comparison to neural network models, PLS and PLS-DA models are more transparent with respect to interpretation.

The Application of PR Methods to Metabonomic Data

Pattern recognition methods have been applied to the analysis of metabonomic data, including, for example, complex NMR spectroscopic data, with some success. See for example: Anthony et al. (1994) Pattern recognition classification of the site of nephrotoxicity based on metabolic data derived from proton nuclear magnetic resonance spectra of urine, Mol. Pharmacol., 46, 199-211; Beckwith-Hall et al. (1998) Nuclear magnetic resonance spectroscopic and principal components analysis investigations into biochemical effects of three model hepatotoxins, Chem. Res. Tox., 11, 260-272; Gartland et al. (1990) Pattern recognition analysis of high resolution $^1$H NMR spectra of urine. A non-linear mapping approach to the classification of toxicological data, NMR in Biomedicine, 3, 166-172; Holmes et al. (1992) NMR spectroscopy and pattern recognition analysis of the biochemical processes associated with the progression and recovery from nephrotoxic lesions in the rat induced by mercury (II) chloride and 2-bromoethanamine, Mol. Pharmacol., 42, 922-930; Holmes et al. (1994) Automatic data reduction and pattern recognition methods for analysis of $^1$H NMR spectra of human urine from normal and pathological states, Anal. Biochem., 220, 284-296.

Data Filtering

Although pattern recognition methods may be applied to 'unfiltered' data, it is often preferable to filter data to removed irrelevant variation. Such filtering requires some degree of supervision to distinguish between relevant and irrelevant variation.

One method of data filtering simply involves deleting selected spectral regions and then working with the remainder. Thus, for example in the $^1$H NMR spectra of aqueous samples acquired with water suppression, the magnitude of the residual water signals will vary according to the effectiveness of the water suppression and these irrelevant signals may be deleted.

Alternatively, variation in the data which is not correlated to (i.e. is orthogonal to) the variation of interest may be removed by 'orthogonal filtering'. One preferred orthogonal filtering method is conventionally referred to as Orthogonal Signal Correction (OSC), wherein latent variables orthogonal to the variation of interest are removed (Wold et al. (1998) Orthogonal Signal Correction of Near Infrared Spectra, Chemometrics and Intelligent Laboratory Systems, 44, 175-185).

Orthogonal Signal Correction

The OSC method locates the longest vector describing the X variation between the objects that is not correlated with the Y-vector, and removes it from the data matrix. The resultant data set has thus been filtered to allow pattern recognition focused on the variation within the object population that is correlated to features of interest, rather than non-correlated, orthogonal variation. This process may be repeated as often as necessary with the proviso that 'over-fitting' should be avoided.

In PLS, the weights, W, are calculated to maximise the covariance between X and Y. In OSC, in contrast, the weights, W, are calculated to minimize the covariance between X and Y, which is the same as calculating components as close to orthogonal to Y as possible. Such components, orthogonal to Y and therefore containing unwanted variation, may then be subtracted from the spectral data, X, to produce a filtered predictor matrix which is focussed on the variation of interest.

If PCA suggests separation of different classes, orthogonal signal correction (OSC) can be used to optimise the separation, thus improving the performance of subsequent multivariate pattern recognition analysis and enhancing the predictive power of the model.

Modelling and Prediction

Inherent in the PLS, PLS-DA and neural networks analyses is the idea of building a predictive mathematical 'model' using 'model-building' or 'modelling' data from samples of known behaviour or type.

Once a model has been calculated, it may be validated using data for samples of known behaviour or type which were not used to calculate the model. In this way, the predictive ability of the model may be tested. Once validated, such models can legitimately be used to predict the behaviour or type of samples of unknown behaviour or type (the test data). Before analysis, the test data must be processed in the same manner as the modelling data, including the application of any filtering.

Any particular model is only as good as the data used to formulate it. Therefore, it is preferable that all modelling and test data are obtained from comparable individuals, under the same (or similar) conditions and using the same (or similar) experimental parameters.

Prior Art for Phenotyping

The variation within sets of biofluid NMR spectra from metabolically unchallenged subjects (i.e. not dosed) may be examined by unsupervised PR methods such as PCA and different groupings may sometimes be observed under constant experimental conditions (e.g. Bollard et al. (2001) Investigations into biochemical changes due to diurnal variation and estrus cycle in female rats using high resolution (1)HNMR spectroscopy of urine and pattern recognition, Anal. Biochem., 295, 2, 194-202). However, this method does not necessarily provide clear information about the significance of the different groupings in relation to metabolic transformations (e.g. Baud-Camus et al. (2001) Determination of N-acetylation phenotype using caffeine as a metabolic probe and high-performance liquid chromatography with either ultraviolet detection or electrospray masspectrometry, Chromatogr. B. Biomed. Sci. Appl., 760, 1, 55-63). By examination of the spectral features that provide discrimination between different groups it may be possible to make an interpretation of the significance of the separation. However, this is an unreliable and untargeted approach that does not provide proof of significance and it is a very inefficient way of examining the potentially subtle and complex variation associated with different metabolic phenotypes.

Conversely, in a targeted approach, it is known to use patterns of components detected in biofluids using NMR spectroscopy, or other techniques, after dosing with test substances (such as caffeine in the case of acetylator phenotype) to establish the ability of a subject to effect particular metabolic transformations. In other words, NMR spectroscopy and other techniques can be used to determine the metabolic phenotype of a subject using post-dose biofluids. In these analyses, the components of interest would normally be the unchanged dosed substance and/or its metabolites. For simplicity the term 'metabolites of the dosed compound' will henceforth be considered to include the dosed compound itself. Often a ratio of such components would be determined as a measure of the relevant metabolic ability. From such analyses it would be possible to determine the ability of a subject with respect to a whole variety of metabolic transformations depending on the availability of suitable test substances. However, in general, the ability of a subject to effect one type of transformation would be expected to be independent of its abilities with respect to all other transformations. Thus, one would expect multiple test substances to be required when investigating a subject's ability with respect to a variety of biochemical transformations. Although such analyses are occasionally carried out, unnecessary dosing of any substance to human or animal subjects is undesirable on safety and ethical grounds and widespread use of such methods is unlikely. A further complication is that dosing a test substance might cause enzyme induction, resulting, for some time afterwards, in an altered metabolic state. Thus, for instance, such phenotyping could be problematic in relation to toxicity studies.

The term biomarker as used herein is normally taken to mean a chemical or biochemical entity in a subject or subject sample or statistically associated combinations of entities, or a physiological response in a subject which has a significance associated with its presence, absence or level, that is indicative of a particular physiological state, disease or toxic process or of a predisposition towards a particular type of metabolic or disease process and may also be associated with a clinical outcome.

Examples of such biomarkers include chemical and biological molecules, for example metabolic substrates, intermediates or products, structural proteins, nuclei acids, transport and receptor proteins, immunological proteins, proteins associated with metabolic or genetic control, catalytic proteins, enzymes and their associated cofactors. Further examples of biomarkers also include levels of activity of biological processes for example gene and protein expression and levels of activity of cellular signalling pathways.

It is appreciated that the term biomarker also refers to any measurable signal associated with or characteristic of the presence, absence or level of the aforementioned molecules or processes; for example signals or patterns of signals resulting from the output of measurements taken by techniques such as nuclear magnetic resonance (NMR) spectroscopy and/or any other chemical analysis techniques such as mass spectroscopy (MS), infrared (IR) spectroscopy, gas chromatography (GC) and high performance liquid chromatography (HPLC) or by using any integrated combination of such techniques e.g. GC-MS.

The term chemical composition as used herein in reference to samples includes the combination of chemical and/or biochemical species which comprise the sample.

The term physical parameters as used herein in reference to samples includes characteristic physical measurements obtained by methods such as chromatography, derivitisation, fractionation and separation, crystallisation, sedimentation, spectral analysis, molecular weight analysis, diffraction, analysis of solubility, analysis of turbidity, refractive index or resistivity, melting point or boiling point.

The Present Invention

The present invention relates to methods for identifying the metabolic phenotype of a subject and to methods for predicting responses and determining risk factors which are influenced by metabolic phenotype. In particular, the present invention includes methods for identifying the metabolic phenotype of a subject and for predicting a subject's responses to one or more treatments by analysing a biofluid of that subject.

As stated above, the recognised approach to metabolic phenotyping relies upon dosing a subject and then analysing a post-dose biofluid. In a radical departure from this, the present invention is based on the unexpected finding that variation in the levels of the metabolites of a dosed substance in a biofluid correlates with variation in the metabolite profile of a biofluid before the substance is administered. Thus, the present invention makes it possible to predict the response of a subject to a substance prior to dosing that substance. Furthermore, the present invention makes it possible to determine a subject's metabolic phenotype without the need to dose that subject with a test substance. Clearly, where a substance has the potential to cause an adverse reaction, it is highly useful to be able to predict a subject's reaction e.g. in pharmaceutical treatments. Additionally, for the reasons described above (safety, ethics and enzyme induction), it is highly advantageous to be able to determine the metabolic phenotype of a subject without the need for any dosing. This new and radically different methodology provides a highly targeted approach to finding pre-dose correlates for post-dose behaviour.

Thus, in one aspect, the present invention provides a generic method for building a model with which to predict a subject's response(s) to a substance potentially to be administered to that individual. In this method, the substance to be dosed would be administered to a representative population of subjects, henceforth referred to as the model building population. The response(s) of interest would be measured in all members of the model building population, by whatever means were appropriate. Biofluid or other samples collected from the model building population before dosing would be examined by $^1$H NMR spectroscopy or by another suitable technique (e.g. near infrared spectroscopy, high performance liquid chromatography, mass spectroscopy or gas chromatography) or by a combination of such techniques. Together, the pre-dose and post-dose response data would constitute the model building data. A chemometric pattern recognition (PR) technique such as PLS or PLS-DA would be applied to the model building data to correlate the variation in the post-dose response(s) with variation in the pre-dose data. Sometimes a data filtering method such as OSC would be used prior to PR to remove uncorrelated variation in the pre-dose data. Once built and validated, the model would be useable in conjunction with appropriate pre-dose data from one or more test subjects, of similar type to the model building population, where it was desired to predict the response to the same substance. Normally, a new model would be required for each substance of interest although a model derived for one substance might be useable in conjunction with a closely related substance.

In another aspect, the present invention provides a generic method for building a model with which to characterise one or more elements of a subject's metabolic phenotype. In this method, the substance to be dosed, and the amount of that substance, would be carefully chosen to challenge the particular metabolic transformation(s) of interest. The chosen substance would be administered to a representative population of subjects, henceforth referred to as the model-building population. The metabolites of interest would be measured, in a post-dose biofluid or other sample, by $^1$H NMR spectroscopy or by other suitable means, as convenient. From this analysis, a measure of the ability of each subject with respect to the relevant metabolic transformation(s) would be determined. Biofluid or other samples collected from the model building population before dosing would be examined by $^1$H NMR spectroscopy or by another suitable technique (e.g. near infrared spectroscopy, high performance liquid chromatography, mass spectroscopy or gas chromatography) or by a combination of such techniques. Together, the pre-dose data and the post-dose 'metabolic ability' measurements would constitute the model building data. A chemometric pattern recognition (PR) technique such as PLS or PLS-DA would be applied to the model building data to correlate the variation in the post-dose ability measurements with variation in the pre-dose data. Sometimes a data filtering method such as OSC would be used prior to PR to remove uncorrelated variation in the pre-dose data. Once built and validated, the model would be useable in conjunction with appropriate pre-dose data from one or more test subjects, of similar type to the model-building population, where it was desired to determine the relevant metabolic ability or abilities.

In a first aspect of the invention there is provided a method of generating models with which to characterise selected aspects of the metabolic phenotype of subjects without dosing a test substance to those subjects or with which to predict, without dosing, the post-dose responses of subjects where those responses are dependent on metabolic phenotype, the method comprising:

obtaining pre-dose data relating to a plurality of subjects before dosing with a dosing substance;

obtaining post-dose data relating to the plurality of subjects after dosing with the dosing substance;

correlating inter-subject variation in the pre-dose data with inter-subject variation in the post-dose data, and generating a pre-to-post-dose predictive model on the basis of the observed correlation.

The pre- and/or post-dose data may be obtained from samples which are biofluids such as urine, blood, blood plasma, blood serum, saliva, sweat, tears, breath or breath condensate or from samples which are plant tissues, plant fluids or homogenates, plant extracts or plant exudates, including, for example, essential oils or from samples which are human or animal tissues, fish tissues or oils, tissue extracts, tissue culture extracts, cell culture supernatants or extracts or of microbial origin. The pre- and/or post-dose data may comprise data relating to chemical composition and/or physical parameters.

The pre- and/or post-dose samples or subjects may be treated prior to analysis (e.g. treated with one or more chemical reagents so as to produce derivative(s) of one or more existing substances), for instance to enhance data recovery or to improve sample stability.

The pre- and/or post-dose data may be derived from or are compositional data acquired using nuclear magnetic resonance (NMR) spectroscopy and/or any other chemical analysis techniques such as mass spectroscopy (MS), infrared (IR) spectroscopy, gas chromatography (GC) and high performance liquid chromatography (HPLC) or by using any integrated combination of such techniques e.g. GC-MS.

The pre- and/or post-dose data may be physical data or data derived therefrom.

Preferably a phenotyping model is generated for each of a plurality of biochemical transformations, by dosing appropriate substances. Similarly, by dosing appropriate substances, a response prediction model may be built for each of a plurality of dosing substances.

The original pre-dose data set may extended, prior to pattern recognition, by taking ratios and/or other combinations of existing variables. This may be achieved for instance by forming further data comprising a ratio or ratios of the obtained data.

For a group of subjects dosed with any particular substance, a pattern recognition method may be used to identify patterns in the variable metabolism of, or the variable reactions to, the dosing substance. A supervised or unsupervised pattern recognition method may be used to identify variation in the pre-dose data that correlates with the variation of interest in the post-dose data.

A data filtering method such as Orthogonal Signal Correction (OSC) may be used to remove variation in the pre-dose data that is not correlated with the variation of interest in the post-dose data.

The method may be used to identify biomarkers or combinations of biomarkers which provide information on metabolic phenotype or which may be used to predict responses to dosing.

In a second aspect of the invention there is provided a method of determining selected aspects of the metabolic phenotype of a subject, the method comprising:

analysing data relating to the un-dosed subject in relation to a model describing the correlation of pre-dose and post-dose data relating to a plurality of subjects dosed with a particular substance which challenges the biochemical transformation or pathway of interest;

generating, according to the predetermined criteria of the model, a numerical measure or classification describing the metabolic phenotype of the un-dosed subject.

The pre-determined criteria of the model include one or more mathematical equations which define the relationship between the pre-dose data and the post-dose data and allow characterisation of subjects on the basis of pre-dose data and allow identification of test data which are outliers.

The data relating to the un-dosed subject may be obtained from a biofluid such as urine, blood, blood plasma, blood serum, saliva, sweat, tears, breath or breath condensate or from a plant tissue, plant fluid, plant homogenate, plant extract or plant exudate, including, for example, an essential oil, or from human or animal tissue, fish tissue or oil, or from a tissue extract, tissue culture extract, cell culture supernatant or cell culture extract or from a sample of microbial origin or from any one of the above sample types after treatment to enhance data recovery or sample stability.

Characteristic compositional and/or physical data relating to a subject may be generated using nuclear magnetic resonance (NMR) spectroscopy and/or any other techniques or by using any combination of techniques.

The phenotyping method may be used for the purpose of making a metabolic phenotype-influenced risk assessment and/or for the purpose of targeting the use of special health monitoring regimes and/or for the purpose of targeting the use of precautionary/preventative treatments and/or for the purpose of characterising risk for insurance purposes and/or for the purpose of selecting subjects for any other purpose e.g. for breeding.

In a further aspect of the invention there is provided a method of predicting the reaction of a subject to a dosing substance, the method comprising:

analysing data relating to an un-dosed subject in relation to a model characterising the correlation of pre-dose and post-dose data relating to a plurality of subjects dosed with the particular dosing substance; and generating, according to the predetermined criteria of the model, a numerical or class prediction for the expected response of the un-dosed subject if it were to be dosed with the dosing substance.

According to pre-determined criteria, the maximum or minimum dose of a substance that a subject should receive can be predicted as well as the amount of a dosing substance that a subject should receive. The frequency with which a subject should be dosed with a substance can also be predicted as well as the number of doses of a substance that a subject should receive. The appropriate controlled release formulation for a subject can be selected.

Characteristic compositional and/or physical data relating to a subject may be generated using nuclear magnetic resonance (NMR) spectroscopy and/or any other techniques or by using any combination of techniques.

The method of determining selected aspects of the metabolic phenotype of a subject or of predicting the reaction of a subject to a dosing substance, may further comprise analysing data relating to the un-dosed subject with respect to one or more biomarkers which have been previously identified. The biomarker(s) may react with one or more added reagents to produce a visible change such as a colour change. Preferably the biomarkers are selected by correlating pre-dose data relating to a plurality of subjects before dosing with a dosing substance and post-dose data relating to the plurality of subjects after dosing with the dosing substance.

The method may be used to select a group of phenotypically homogenous or similar subjects for a laboratory experiment or clinical trial or for any other purpose.

The method may be used for rationalising biological variation in experimental data based on pre-dose analysis of biofluids or tissues, where such variation is caused by phenotypic heterogeneity.

The data may be based on physical and/or chemical measurements taken from the subject as a whole. Examples of such measurements are blood pressure, heart rate, peak flow, height, weight etc.

The post-dose data may describe a change relative to the pre-dose state e.g. a decrease in blood pressure of a human subject treated with a drug that lowers blood pressure.

Preferably test data that does not conform to the limits of a particular model and/or method is identified.

The subject may be an animal, in particular a mammal such as a human, a mouse, a rat, a pig, a cow, a bull, a sheep, a horse, a dog or a rabbit or any farmed animal or any animal, such as a race horse, used for the purpose of sport or for breeding. Alternatively the subject may be a plant, a fish or any other aquatic organism or a biological tissue, a tissue culture, a cell culture or a microbial culture.

Data may be obtained from a sample which is representative, or is taken to be representative, of a group of subjects which are considered as a single subject. For instance, samples from a plurality of like subjects (e.g. a plant) may be ground together and the resulting material used to obtain data considered to relate to a single plant subject.

The dosed substance may be any substance or mixture or formulation of substances including especially pharmaceutical or medicinal substances or substances in research or development which might potentially become pharmaceutical or medicinal substances, but also including, for example, toxins, pesticides, herbicides, food or feed substances, food or feed additives and fluids of any sort including liquids, gases, vapours and smoke e.g. tobacco smoke.

The dosed substance may be actively or passively dosed in any matrix or medium, by any means or route, including for example, by injection, by eating, by drinking, by inhaling or by smoking, over any time period including a subject's lifetime or any specified part or fraction thereof, such dosing to include that resulting from environmental exposure or pollution or from medical, dental, veterinary or surgical procedures.

The method may be used for identifying the acetylator phenotype of a subject without dosing a test substance to that subject. Additionally or alternatively the method may be used for predicting the response of a subject to dosing with a substance where that response is dependent on acetylator phenotype.

The method may be used to predict the susceptibility of a subject to isoniazid-induced toxicity or galactosamine-induced toxicity.

The invention also relates to apparatus for generating models.

In a further aspect of the invention there is provided apparatus for response prediction and/or for metabolic phenotyping, the apparatus comprising:

one or more models, each model modelling the correlation of pre-dose and post-dose data relating to a plurality of subjects dosed with a particular dosing substance;

a processor for analysing data relating to an un-dosed subject in relation to at least one of the models and thereby determining one or more aspects of the metabolic phenotype of the un-dosed subject or predicting its responses to dosing according to the model(s) employed.

Additionally or alternatively the apparatus is further arranged to generate one or more models with which to characterise selected aspects of the metabolic phenotype of subjects without dosing a test substance to those subjects or with which to predict, without dosing, the post-dose responses of subjects where those responses are dependent on metabolic phenotype, the apparatus being arranged to:

obtain pre-dose data relating to a plurality of subjects before dosing with a dosing substance;

obtain post-dose data relating to the plurality of subjects after dosing with the dosing substance; and correlate inter-subject variation in the pre-dose data with inter-subject variation in the post-dose data, and generating a pre-to-post-dose predictive model on the basis of the observed correlation.

Preferably the apparatus may further comprise one or more analytical instruments or devices to carry out physical and/or chemical analysis, such as NMR spectroscopy, mass spectroscopy, infrared spectroscopy or high performance liquid chromatography.

The apparatus may also be arranged to identify one or more biomarkers, in particular for response prediction or metabolic phenotyping based on the use of one or more biomarkers which have been previously identified as described.

In a further aspect of the invention there is provided apparatus for metabolic phenotyping or for predicting a subject's response(s) to dosing, the apparatus comprising:

a test area to receive a sample from the subject under test, said test area incorporating one or more reagents which may react chemically with one or more biomarkers in the sample to produce a change in the visual appearance of the test area, the biomarkers having been previously identified as described, and the resulting visual appearance of the test area being characteristic of metabolic phenotype or predictive of response(s) to dosing.

Preferably the apparatus identifies an appropriate dosing regime for a subject.

The apparatus may be based on the use of antibodies raised against specific biomarkers. Selected biomarkers may be detected and/or quantified by means of enzyme-catalysed reactions using, for instance, enzymes immobilised on a solid support.

The invention also relates to apparatus comprising one or more models generated by a method according to the invention.

The apparatus may be further arranged to identify test data that does not conform to the limits of a particular model.

The invention has many applications:

(1) 'Well' Subjects not Requiring Corrective Treatment

Metabolic characterisation (phenotyping) of subject enabling:

risk assessment e.g. bladder cancer particularly associated with certain phenotype.

targeted adoption of special health monitoring regimes where appropriate i.e. in high risk subjects.

targeted use of precautionary/preventative treatments where appropriate i.e. in high risk subjects.

identification, for insurance purposes, of the degree of risk associated with a subject.

selection of subjects with desirable characteristics e.g. in breeding farm animals.

selection of phenotypically homogenous subsets of subjects for laboratory or clinical experiments.

(2) Subjects Requiring Pharmaceutical, Medical, Dental, Veterinary or Other Treatments Metabolic characterisation (phenotyping) of the subject and/or prediction of the subject's responses to dosing or treatment, enabling:

avoidance of adverse drug reactions (e.g. coma, fatality) either by not administering the drug to vulnerable subjects or by reducing the drug dose and/or the frequency and/or duration of such dosing.

prediction of occurrence and degree of severity of minor side effects of drug treatments (e.g. nausea, drowsiness).

selection of optimal pharmaceutical treatment (compound, dose, dose-frequency and duration of course of treatment) based on maintaining an appropriate level of the active drug substance in the body whilst minimising side-effects.

avoidance of adverse reactions to medical, dental, veterinary procedures and substances e.g. anaesthetics such as halothane.

selection of appropriate medical, dental or veterinary procedures or treatments.

(3) Drug Development and Licensing

Drugs having different effects (e.g. efficacy, toxicity) in different subjects could be licensed under the proviso that pre-dose metabolic phenotyping would be carried out and treatments tailored accordingly. This would enable:

a reduction in 'attrition' (abandonment of compounds during the drug development process) because of variable responses either in efficacy or in toxicity.

recovery/relicensing of certain non-approved drugs where the problems in effectiveness or toxicity were limited to certain subsets of subjects rather than the population as a whole.

In relation to drug development studies (e.g. for toxicity or efficacy) pre-dose metabolic phenotyping would enable:

interpretation of variable results where that variation resulted from phenotypic differences between different subjects or between different subsets of subjects.

selection of desired test groups having certain required metabolic characteristics.

(4) Biomarker Identification

Instead of being used directly for analysis of test data, appropriate models could be used to identify biomarkers or combinations of biomarkers with which to determine metabolic phenotype or with which to predict responses determined by metabolic phenotype. Having established the relevant biomarker(s), simplified methods of analysis, e.g. urine dipsticks or HPLC methods, could then be developed based on those biomarkers. This would reduce reliance on sophisticated technologies such as NMR spectroscopy and would enable more remote testing e.g. in local laboratories, pharmacies, hospitals or doctors' surgeries.

The invention will now be described further, by way of example only, with reference to the accompanying drawings, in which:

FIG. 1.1 shows the variable urinary excretion of galactosamine after dosing with Galactosamine HCl (abbreviated GalN HCl) (800 mg/kg);

FIG. 1.2 shows the variable urinary excretion of an N-acetylated species after dosing with GalN HCl (800 mg/kg);

FIG. 1.3 shows some urinary changes induced by GalN HCl (800 mg/kg) in a responder;

FIG. 1.4 shows the altered urinary excretion of hippurate and histidine after dosing with galactosamine HCl (800 mg/kg);

FIG. 1.5 shows the scores plot on PC 1 vs. PC 5 from a PCA of the day −1 (pre-dose) urine NMR spectra from the galactosamine study;

FIG. 1.6 shows the loadings plot on PC 1 vs. PC 5 from the PCA of the day −1 (pre-dose) urine NMR spectra from the galactosamine study;

FIG. 2.1 shows examples of the different patterns of N-acetylated metabolites seen in the NMR spectra of urine samples collected from 0-7 hours after dosing isoniazid (400 mg/kg) to male Sprague-Dawley rats;

FIG. 2.2 shows the scores plot on PC 1 vs. PC 2 from a PCA of the N-acetyls region ($\delta$ 2.23 to $\delta$ 2.13) of the NMR spectra of the day 1 (0-7 hours from dosing) urine samples from the animals dosed with isoniazid (200 mg/kg);

FIG. 2.3 shows two optional initial pathways for isoniazid metabolism;

FIG. 3.1 shows pre-dose prediction of the ratio (peak height 'a'/peak height allantoin) in the NMR spectra of urine samples collected from 0-7 hours after dosing isoniazid (200 mg/kg);

FIG. 3.2 shows the regression coefficients pertaining to the PLS analysis which gave rise to the results described in FIG. 3.1;

FIG. 3.3 shows pre-dose prediction of the amount of metabolite C excreted in the urine collected from 0-7 hours after dosing rats with isoniazid (200 mg/kg).

FIG. 3.4 shows pre-dose prediction of the ratio [(Fraction C)/(Fraction A+B)] in the urine collected from 0-7 hours after dosing rats with isoniazid (200 mg/kg).

FIG. 3.5 shows the internal validation of the model relating to FIG. 3.4.

FIG. 3.6 shows pre-dose predictions of [(Fraction C)/(Fraction A+B)] for an external test set.

FIG. 4.1 shows pre-dose prediction of the total urinary excretion of N-acetylated compounds ($\delta$ ca. 2.22-ca. 2.11) in the 24-hour period after dosing rats with paracetamol. (1.sup.st model for this parameter).

FIG. 4.2 shows pre-dose prediction of the amount of 'MA' excreted in the 24-hour period after dosing rats with paracetamol. ($1^{st}$ model for this parameter).

FIG. 4.3 shows pre-dose prediction of the total urinary excretion of N-acetylated compounds ($\delta$ ca. 2.22-ca. 2.11) in the 24-hour period after dosing rats with paracetamol. ($2^{nd}$ model for this parameter).

FIG. 4.4 shows the internal validation of the model relating to FIG. 4.3.

FIG. 4.5 shows pre-dose prediction of the urinary excretion of paracetamol glucuronide ('G') in the 24-hour period after dosing rats with paracetamol.

FIG. 4.6 shows the internal validation of the model relating to FIG. 4.5

FIG. 4.7 shows pre-dose prediction of the urinary excretion of 'MA' in the 24-hour period after dosing rats with paracetamol. ($2^{nd}$ model for this parameter).

FIG. 4.8 shows the internal validation of the model relating to FIG. 4.7

FIG. 4.9 shows the external validation of the model relating to FIG. 4.7

FIG. 4.10 shows pre-dose prediction of the urinary excretion of 'P' in the 24-hour period after dosing rats with paracetamol.

FIG. 4.11 shows the internal validation of the model relating to FIG. 4.10

FIG. 4.12 shows the observed versus pre-dose predicted values for the amount of 'S' excreted in the 24-hour period after dosing rats with paracetamol.

FIG. 4.13 shows the observed versus pre-dose predicted values for the GIS ratio in the 24-hour urine samples obtained after dosing rats with paracetamol.

FIG. 5.1 shows pre-dose prediction of the total urinary excretion of N-acetylated compounds ($\delta$ 2.210-2.135) per kg of body mass in the first three hours after dosing human males with paracetamol.

FIG. 5.2 shows the external validation of the model relating to FIG. 5.1.

FIG. 5.3 shows pre-dose prediction of the amount of paracetamol glucuronide ('G') excreted in the urine per kg of body mass in the first three hours after dosing human males with paracetamol.

FIG. 5.4 shows the external validation of the model relating to FIG. 5.3.

FIG. 5.5 shows pre-dose prediction of the amount of 'P' excreted in the urine per kg of body mass in the first three hours after dosing human males with paracetamol.

FIG. 5.6 shows the external validation of the model relating to FIG. 5.5.

FIG. 5.7 shows pre-dose prediction of the total urinary excretion of N-acetylated compounds ($\delta$ 2.210-2.135) per kg of body mass in the first six hours after dosing human males with paracetamol.

FIG. 5.8 shows the external validation of the model relating to FIG. 5.7.

A. PREFERRED FEATURES OF THE MODEL BUILDING PROCEDURE

1. The Model Building Population.

The subjects who form the model-building population should, as far as possible, be representative of the subjects who will form the test population. Diet can affect biofluid composition and inter-subject dietary variation could therefore be important in relation to biofluid-derived models. Ideally, the methods would be sufficiently robust so as to be unaffected by dietary variation but this would require testing for each model. As a precaution against the possible effect of a variable diet, it would be advisable for all the model building, validation and test data relating to a particular model to be acquired from subjects receiving the same diet. This is easier to achieve for laboratory animals than it is for humans. In fact, it could be advantageous if standard animal diets and a standard human diet were to specified for all relevant exercises as this would enable rapid checking of a test subject's urine sample against a range of different models. In general, the larger the size of the model-building population, the more robust will be the model created. Once a model has been built it would need to be validated using a group of subjects who were not members of the model-building population.

2. Dosing

The substance dosed, the dose level, the frequency of dosing and the means of dosing will depend on the application. Where the aim is to produce a method for metabolic phenotyping, the dosed substance would need to provide one or more metabolites with which to characterise the extent of the transformation(s) of interest. Ideally, the selected metabolites would only be affected by the transformation(s) of interest and would not be subject to other complications. It is, therefore, likely that the dosed compounds would be small uncomplicated chemical compounds with perhaps mono- or bi-chemical functionality. For building such phenotyping models it is likely that a single dose of the selected substance would be sufficient but this dose would need to be large enough to provide discrimination between metabolically-different individuals. Where the aim is to build a model for response prediction, the dosing regime should be identical to that for which the response is to be predicted in the test subjects.

3. Samples a. Pre-Dose Samples

The pre-dose sample(s) will need to be selected so as to contain relevant metabolic information. If necessary, samples of more than one type could be taken and their information content combined. Preferably the sample(s) would be easy to obtain and the sampling procedure(s) would cause minimal pain and inconvenience. To minimise the potential for changes in metabolic phenotype to occur between time of pre-dose sampling and the time of dosing, the pre-dose samples should be obtained as near as possible to the time of dosing.

Urine is an ideal pre-dose sample because it contains a wealth of metabolic information and can be sampled with little or no inconvenience especially to human subjects. Additionally, with humans, urine can be sampled essentially on demand. Urine collection from animals such as rats is slightly more difficult; it cannot be obtained on demand and smaller animals such as rats would generally have to be housed within individual cages for several hours with special arrangements for urine collection.

Blood also contains metabolic information and, in small quantities, is relatively easy to sample from larger animals or humans by a 'pin-prick' method. However, special arrangements have to be made to inhibit clotting e.g. the use of blood serum or of vials containing lithium heparin. Larger quantities of blood are more difficult to obtain especially from smaller animals and specialised techniques and phlebotomists may be required. Anaesthesia and/or sedation may be required depending on the site of blood sampling and the ease of immobilising the subject. Blood plasma or blood serum are the two blood-derived fluids that would normally be analysed.

Saliva, sweat, exhaled breath or exhaled breath condensate, tears and maternal milk are other body fluids which would be easy to obtain and might contain relevant metabolic information depending on the nature of the investigation.

b. Post-Dose Samples

The post-dose sample type will depend on the application. The post-dose sample could be the whole subject e.g. a human or a rat, or a sample derived from that organism, as in section a. above. Where necessary, samples of more than one type could be taken.

c. Sample Stability

Special arrangements need to be taken to ensure the stability of biological samples which would otherwise be subject to degradation by bacteria or other means. As stated above, special arrangements need to be made to prevent the clotting of blood or blood plasma. Urine samples, especially those which might have been subjected to faecal or other contamination, are best collected into vials containing an anti-bacterial agent such as sodium azide. Sodium azide has the benefit of being invisible to $^1$H NMR spectroscopy. Where the urine sample is collected over a significant period of time, i.e. for hours rather than minutes, it is best if the collection vessel or bag is cooled by ice or other means. Once collected and stabilised, all biological fluids should either be analysed immediately or stored deep-frozen (−20 C or below) pending analysis. Preferably, any 'solid' tissue samples would be 'snap' frozen in liquid nitrogen immediately after collection and subsequently stored at −80 C pending analysis. Collection and storage vessels should be selected which will not contaminate the samples by leakage of plasticisers or other plastic components.

4. Sample Preparation

Some sample preparation or treatment may be required prior to analysis. Samples for $^1$H NMR spectroscopic analysis are typically prepared as follows although there may be much variation in the exact procedure used by different workers:

a. Urine Samples

Urine samples are typically prepared for NMR analysis by mixing 400 μl of urine with 200 μl of phosphate buffer (an 81:19 (v/v) mixture of 0.2 M $Na_2HPO_4$ and 0.2 M $NaH_2PO_4$; pH 7.4); if insufficient urine is available the shortfall is made up with purified water with a minimum of 200 μl of urine being used. The urine-buffer mixture is left to stand for 10 minutes at room temperature to enable buffering to take place and then centrifuged at 13,000 rpm for a further 10 minutes to remove suspended particulates. 500 μl of 'clear' buffered urine is transferred to an NMR tube and 50 μl of a $TSP/D_2O$ solution added. TSP (sodium 3-trimethylsilyl-[2,2,3,3-$^2H_4$]-1-propionate) is a chemical shift reference compound ($\delta$ 0) used in the NMR experiment and the $D_2O$ provides a field/frequency lock for the NMR spectrometer. The concentration of the $TSP/D_2O$ solution is such as to give a final TSP concentration of 0.1 mM in the NMR tube.

b. Plasma Samples

Plasma samples are typically prepared for $^1$H NMR analysis by mixing 150 μL of plasma with 350 μL of saline (0.9% (w/v) NaCl in a mixture of 10% (v/v) $D_2O$ and 90% (v/v) $H_2O$). Chemical shift reference compounds such as TSP are not added because of the likelihood of binding to protein in the sample.

Depending on the analytical technique to be employed, chemical derivatisation of the sample could be used to enhance data recovery. Thus, for example suitable chromophores could be attached to compounds which would otherwise be undetectable to spectrophotometric detectors monitoring the absorption of ultraviolet or visible light. Another option would be to attach fluorescent markers to enhance the detectability of compounds by fluorimetric analysis. By such chemical derivatisation, previously undetectable compounds could be made detectable and detection limits could be improved for others. Chemical derivatisation could also be employed to facilitate the chromatographic separation of different sample components. Physical and/or chemical treatments could also be employed to remove undesirable sample components such as plasma proteins which might otherwise cause problems during the analysis.

5. Physical-Chemical Analytical Techniques a. Analysis of Post-Dose Samples

The analytical technique(s) need to be chosen with regard to the parameter(s) being measured and the number and nature of the samples e.g. whole organism or biofluid type. The huge range of parameters that might be of interest in different models means that a wide range of analytical instrumentation and methods could be required.

If the application is to measure specific response(s), e.g. the change in blood pressure, after dosing with a particular substance then the most appropriate technique(s) should be chosen, e.g. sphygmomanometer. If the toxicity of a substance is the focus of interest then it may be best to measure a range of blood plasma parameters, such as enzyme activities, using, for instance, an automated clinical analyser equipped with appropriate kits. Alternatively, histopathological findings could be classified according to type of effect or could be numerically scored according to degree of severity. Where the aim is to build a phenotyping model the post-dose analytical technique would normally need to provide quantitation, or at least relative quantitation, of one or more metabolites of the dosed substance.

b. Analysis of Pre-Dose Samples

As with the post-dose samples, the choice of analytical technique for the pre-dose samples will be influenced by the nature of the samples but, additionally, the chosen pre-dose analytical technique would need to be able to reveal metabolic information. Preferably, analysis of a body fluid or body tissue would be by means of NMR spectroscopy or by another technique which is capable of undirected metabolite detection and quantitation i.e. the chosen technique would ideally detect and quantify individual metabolites without the need to specify analysis of those particular metabolites. This allows for the use, within the model, of the most useful metabolites even if they are not presently known. It also allows for the identification of new metabolite markers where that is of interest. For model-building, it is not necessary that each observed metabolite is identified but, rather, the analytical technique should provide a reliable quantitative fingerprint of each sample. Ideally, the chosen technique would be readily accessible but this might not always be possible because of the expense and the level of sophistication required. One possible technique, that is standard analytical equipment in most analytical chemistry laboratories, is High Performance Liquid Chromatography (HPLC) with, for instance, UV-Visible spectrophotometric detection. Although it can be rather time-consuming, the HPLC technique would be capable of providing the type of data that is required from a pre-dose sample. The choice of the detector for HPLC would be a critical factor and data recovery could be facilitated by chemical derivatisation of the sample prior to analysis. The use of NMR spectroscopy would not be limited to any particular type of NMR experiment.

c. Variable Performance of Different Analytical Instruments

Different analytical instruments may perform differently and the performance of a single piece of equipment may vary over time. Such instrumental variation could be particularly important where subtle pre-dose variation between samples needs to be characterised to build a successful model although data filtering such as OSC could help to minimise its effects in 'supervised' PR analyses. Therefore, in building a particular model, all measurements of a particular type would, ideally, be taken on a single occasion using one specific instrument. If it were not possible to carry out all the analyses on one occasion it would be necessary to ensure that instrument performance had not varied significantly between the different periods of use. Where multiple pieces or types of equipment were used in taking measurements from the model-building population, it would be necessary to carry out cross-checks to ensure similar performance from each instrument. Deselection or recalibration of instruments would need to be carried out where there was a significant difference in performance between different instruments.

6. Data Manipulation Prior to Multivariate PR Analysis

It may be helpful or necessary to carry out some data manipulation prior to PR analysis.

Ideally, all the available physical and/or chemical data would be used in creating the input data for the chemometric analysis. However, depending on the type of data acquired, some data reduction may be required prior to multivariate analysis. With $^1H$ NMR spectroscopic data of biofluids such as urine this has been used, despite buffering, to cope with small pH-induced shifts in the position of peaks on the chemical shift scale. Thus, after deleting certain regions such as the residual water signals, the remainder of each 1D $^1H$ NMR spectrum is divided along its abscissa into sequential segments (typically of 0.04 ppm width for a 600 MHz spectrometer) and an integral obtained for each segment. Where such data reduction is required it would be advisable to try a different data reduction method, e.g. to use different spectral segment widths, if the previous attempt had not yielded an adequate model. The use of a data filtering technique such as OSC could facilitate data reduction by assisting with variable selection.

With biofluid NMR data it is common practice to 'normalise' each data-reduced spectrum and there are a number of ways of doing that. Frequently, each NMR spectrum is normalised, or scaled, to give the same total integration as every other NMR spectrum in the data set. Additionally, other data manipulations may prove to be helpful e.g. scaling the $^1H$ NMR data from urine samples to a constant integration for the allantoin peak at $\delta$ 5.4, if present, or to a constant integration for a creatinine peak. In man, urinary creatinine excretion is related to muscle mass which in turn is loosely related to body mass. Scaling urine data to constant creatinine should therefore help to eliminate differences in excretion that are related to body mass. Additionally, by determining a measure of metabolite concentrations in urine and by taking account of the amount of urine excreted by each subject it should be possible to obtain a data set which truly represents metabolite excretion by each subject. Where metabolite excretion has been determined, and body mass is also known but variable, it may be useful to normalise urine data to excretion per unit body mass. It may also be useful to 'block' the data so that variables with values falling within a particular range are treated as a discrete group.

A particular limitation of analyses such as PCA, PLS or PLS-DA is that they rely on finding useful linear combinations of existing variables despite the fact that a non-linear combination of variables might be more instructive. Thus, before carrying out such analyses it would be sensible to extend the X data matrix by adding non-linear combinations of the existing variables. In particular, the ratio of two variables is often more significant than the absolute value of either and taking ratios could be especially helpful in relation to metabolic phenotyping where the relative amounts of different metabolites are often important. Thus, the extended X matrix should include the original X variables together with the one-to-one ratios of all those original variables except for the ratio of one variable to itself. This approach is shown in the following simple example:

Original X matrix:

| Sample or object | Variable X1 | Variable X2 |
|---|---|---|
| A | 25 | 25 |
| B | 16 | 8 |
| C | 8 | 2 |

Extended X matrix:

| Sample or object | Variable X1 | Variable X2 | Variable X1/X2 |
|---|---|---|---|
| A | 25 | 25 | 1 |
| B | 16 | 8 | 2 |
| C | 8 | 2 | 4 |

In a slightly more complicated example three original X variables are extended to produce a new six variable matrix:
Original 3 variable matrix:

| Sample or Object | Variable X1 | Variable X2 | Variable X3 |
|---|---|---|---|
| A | 25 | 25 | 50 |
| B | 16 | 8 | 32 |
| C | 8 | 2 | 4 |

Extended matrix:

| Sample or object | Variable X1 | Variable X2 | Variable X3 | Variable X1/X2 | Variable X1/X3 | Variable X2/X3 |
|---|---|---|---|---|---|---|
| A | 25 | 25 | 50 | 1 | 0.5 | 0.5 |
| B | 16 | 8 | 32 | 2 | 0.5 | 0.25 |
| C | 8 | 2 | 4 | 4 | 2 | 0.5 |

The potential benefit of this approach is demonstrated in the following simple PLS-type example where one wishes to predict a single Y variable from two X variables:
Original data matrix:

| Sample or object | Variable X1 | Variable X2 | Variable Y1 |
|---|---|---|---|
| A | 25 | 25 | 2 |
| B | 16 | 8 | 4 |
| C | 8 | 2 | 8 |

Extended matrix:

| Sample or object | Variable X1 | Variable X2 | Variable X1/X2 | Variable Y1 |
|---|---|---|---|---|
| A | 25 | 25 | 1 | 2 |
| B | 16 | 8 | 2 | 4 |
| C | 8 | 2 | 4 | 8 |

In the original matrix there was no constant linear combination of X1 and X2 that would produce Y1. However, by extending the X matrix as described a very simple linear relationship becomes apparent i.e. Y1=2(X1/X2).

For each variable in the data set some form of scaling will normally be required prior to performing a chemometric analysis. Typical scaling approaches include mean-centering, unit variance scaling and pareto scaling.

7. Chemometrics Methodology

It is important to realise that the scope of this invention is not limited to the use of particular specified chemometrics methodologies. Any such methodologies which could identify and establish pre-to-post-dose data correlations could be employed.

Supervised pattern recognition (PR) methods such as PLS or PLS-DA would normally be employed to achieve targeted model building i.e. pre-to-post dose data correlations. It is possible that these supervised methods would be preceded by the use of unsupervised PR methods such as PCA e.g. to examine the variation in the responses to a dosed compound or to examine the variation in the metabolism of a dosed compound. Such unsupervised analysis could be helpful in identifying outliers and in deciding whether to build a classification method or whether to build a numerical result model (see below).

Occasionally, in a less sophisticated approach to achieving a model for pre-dose discrimination of some aspect of metabolic phenotype or response prediction, it might be adequate to apply an unsupervised method such as PCA to the pre-dose data. This approach has a simplicity advantage although it would be much less able to determine subtle discriminators than the supervised methods. Such a method would rely on being able to code (e.g. colour code) the individual model building pre-dose data points according to post-dose behaviour. The success or otherwise of this approach would depend on the ease with which the coded populations could be distinguished pre-dose. In general, this unsupervised approach would only be suitable where there were relatively obvious pre-dose discriminators for the different response groups. It would not be suitable where the discriminators were complex and 'hidden' and, importantly, data filtering methods such as OSC could not be employed with this 'unsupervised' approach.

The chemometrics method(s) to be employed in the model building will depend on the final application that is envisaged or required. Thus, a classification method such as PLS-DA would be appropriate when the objective was to achieve a method for classification of some aspect of metabolic phenotype (e.g. 'fast' or 'slow' acetylation) or for prediction of the type of response to a dosed substance (e.g. 'adverse drug reaction' or 'no adverse drug reaction'). Alternatively, where the objective was to achieve a quantitative measure of some aspect of metabolic ability or to predict a numerical measure of some response to a dosed substance, methods such as PLS would be appropriate. Neural networks analysis (NNA) can be useful, depending on the application, and NNA has been proven to be advantageous in a classification role where pre-dose discrimination may come from one of a number of independent sources e.g. if the X data is of type A or B or C then the response will be Y1, if the X data is not of those types then the response will be Y2. Importantly, neural networks methods do not readily enable identification of those pre-dose features which provide the discrimination of interest. Methods such as PCA, PLS and PLS-DA do readily enable the identification of discriminatory features and this would be an important advantage in understanding the scientific basis of any discrimination and where it was desired to derive other analytical methods to perform the same discrimination.

Data filtering methods such as OSC would sometimes be employed to remove variation in the pre-dose data that is not correlated to the variation of interest in the post-dose data. For instance, OSC can help to minimise the effects of any variation in the performance of the analytical instrument(s) used in the physical and/or chemical analysis.

Frequently, a relatively small number of outliers will need to be excluded from the model-building data because their data is in some way inconsistent or a hindrance to the model building, PCA scores plots and DmodX values may be used to identify outliers. In the case of PLS models, outliers could be legitimately excluded by any of the following means:
  a) An examination of the X scores (t1/t2)
  b) An examination of the X residuals (DmodX)
  c) An examination of the correlation between the scores in the X and Y spaces (e.g. t1/u1).
  d) An examination of the Y scores (e.g. u1/u2)
  e) An examination of the Y residuals (DmodY).

8. Response Prediction Applications

Substances dosed to living organisms will frequently be subject to a variety of different metabolic transformations. Each of the ensuing metabolites might then in turn undergo a variety of further transformations and so on and so forth. Thus, the complete metabolism of one original compound could involve an extremely complex morass of different pathways and many different enzymes. Consequently a multiplicity of different phenotypic influences could contribute to the nature of the response to a dosed substance and it could be very difficult to deconvolve all those different influences. Therefore, in regard to response prediction applications, it is preferred that the invention is used to directly predict the response without deconvolving the different influences. Thus, for instance, the vastly variable degree of liver damage (as shown by histopathology and clinical chemistry parameters) caused when male Sprague-Dawley rats are dosed galactosamine HCl (800 mg/kg) (see Example 1) might, in principle, be directly correlated with variation in pre-dose urine so as to provide a predictive model for susceptibility to galactosamine HCl, without needing to understand the metabolic factors that are determinants of the response.

B. PREFERRED FEATURES OF THE MODEL VALIDATION PROCEDURE

Verification of model validity is of great importance in all types of mathematical modelling. Validation of a model's robustness and predictive ability requires a validation data set that is independent of the data used for model building. The predictive ability of a model is assessed according to the magnitude of the errors associated with the model-based predictions for the validation data set. The robustness of a model can be judged by comparing the magnitude of the estimated error for the model with the magnitude of the error associated with the model-based predictions for the validation data set. For a model to be considered as reliable for future predictions of 'unknown' samples both requirements, predictability and robustness, should be fulfilled.

In the case of PLS models, both 'internal' and 'external' validation may be performed as follows:

'Internal' validation of PLS models may be effected firstly by determining the $R^2Y$ and $Q^2Y$ values and secondly by observing the effect, on those values, of randomising the positions of the Y data in relation to their corresponding rows in the X matrix (typically 20 separate row permutations would be performed). $R^2Y$ provides a measure of the ability of the PLS model to explain the Y data from the X data, with all the data included in the model. However, spuriously high $R^2Y$ values can be obtained by over-fitting and the real test of a PLS model is its predictive ability. $Q^2Y$ provides a measure of the predictive ability of a PLS model and is obtained by a cross-validation procedure wherein different portions of the XY data are sequentially held out for X to Y prediction using models derived from the remainder of the data. Both $R^2Y$ and $Q^2Y$ have a theoretical maximum value of 1, although $Q^2Y$ should normally be less than $R^2Y$. Subject to the actual values of $R^2Y$ and $Q^2Y$, a value of $Q^2Y$ close to $R^2Y$ implies good predictive ability. In the second stage of the internal validation of a PLS model, the positions of the Y data are randomised and both the $R^2Y$ and $Q^2Y$ values should decrease substantially if the original model was valid. Randomisation of the positions of the Y data relative to their corresponding rows in the X matrix should result in a large decrease in $Q^2Y$, ideally to zero. $R^2Y$ values should also decrease substantially on randomisation of the Y data but would not necessarily decrease to zero because the modelling procedure will always try to find something in the X data, even noise, that can predict the randomised Y data.

'External' validation of PLS models may be performed by taking a test set of animals that do not form part of the model-building population and whose Y values approximately span the range of the Y data in the model. For the model to be taken as valid the prediction errors for the test samples (In the SIMCA software from Umetrics this is designated RMSEP—root mean square error of prediction) must be in the same range as the estimation errors for the model samples (In the SIMCA software from Umetrics this is designated RMSEE—root mean square error of estimation).

C. PREFERRED FEATURES OF THE TESTING PROCEDURE

One very important feature of this invention concerns the identification of subjects with unusual or extreme metabolic phenotypes. Subjects such as these may be particularly prone to suffering adverse or idiosyncratic drug reactions. Given the practical limitations that apply to the numbers of subjects that can be included in any model building exercise, it is impossible to build a model based on the full range of metabolic phenotypes and rare phenotypes are unlikely to be included. Additionally ethnic differences are likely to be important sources of phenotypic variation. However, it is an important feature of the current invention that, at the testing stage, any phenotype that does not conform to the range of phenotypes in the model will be identifiable as an outlier. In the case of PCA and PLS models, for example, these outliers will be detected either in the direction of the model plane or hyperplane described by the PC- or PLS-scores or in the model residual direction, the distance to model (DModX, Y). Additionally, in the case of PLS modelling, outliers in the scores direction can be present in X-space (T), in Y-space (U) and in the inner relation between X and Y (T/U). With test subjects identified as outliers, their metabolic phenotype would not be identifiable, or their response to the dosing substance in question would not be predictable, with adequate confidence. Therefore, in response prediction applications, it would be sensible either not to dose the substance at all to such outliers or to proceed with great caution e.g. with an initial low dose. Thus, despite the practical limitations of the model building procedure, the model should be able to provide useful information with respect to all of the test subjects.

A single NMR spectrum of, say, a subject's urine could be compared against a variety of models to predict that subject's responses to a variety of treatments or to assess several aspects of the subject's metabolic phenotype. The NMR spectrum could be stored electronically for use as and when required. This type of approach would reduce the amount of physical and/or chemical testing required although testing at different stages of a subject's life could be required to allow for age-related alterations in metabolic phenotype.

Normally, a new model would be required for each substance of interest although a model derived for one substance might be useable in conjunction with a closely related substance.

Preferred features of each aspect of the invention are as for each of the other aspects mutatis mutandis. The prior art documents mentioned herein are incorporated to the fullest extent permitted by law.

EXAMPLES

Example 1

The Variable Response of Sprague-Dawley Rats to Dosing with Galactosamine Hydrochloride An example of a possible response prediction method based on the use of a simple response-coded PCA of the NMR spectra of pre-dose biofluid samples.

Thirty young adult age-matched male Sprague-Dawley rats were obtained from Charles River, France. After observation to ensure that they each appeared healthy they were placed in individual metabolism cages with free access to water and a standard commercial laboratory diet (diet AO4C from Usine d'Alimentation Rationnelle, Villemoisson-sur-Orge, France). The laboratory temperature was maintained at 20.+−−.2 degrees C. and the relative humidity at 60.±.20%. The laboratory air was filtered and changed 14 times per hour. A fixed '12 hours light-12 hours dark' cycle was imposed. The study commenced after a short period of cage 'acclimatisation'. The sampling regime is as shown in Table 1.1.

TABLE 1.1

The sampling regime for the Galactosamine HCl study. B, U and P denote sampling for blood, urine and pathology respectively. Dosing was carried out at the start of day 1.

| Group | Day | | | | | | | | | | | |
|---|---|---|---|---|---|---|---|---|---|---|---|---|
|  | −3 | −2 | −1 | 1 | 1 | 2 | 3 | 4 | 5 | 6 | 7 | 8 |
| Urine collection period/hrs | 0-7 | 0-7 | 0-7 | 0-7 | 7-24 | 0-7 | 0-7 | 0-7 | 0-7 | 0-7 | 0-7 | — |
| Late euthanased group | BU | U | U | U | U | U | U | U | U | U | U | BP |
| Early euthanased group | BU | U | U | U | U | BP | — | — | — | — | — | — |

At the time of dosing (at the start of day 1) the growing rats were each approximately 260 g in mass. Galactosamine (abbreviated GalN) HCl (from Sigma, France) was dissolved in physiological saline and dosed by intraperitoneal injection at either 200 mg/kg or at 800 mg/kg; ten animals (nos. 101-110) received the low dose and ten animals (nos. 201-210) received the high dose. Ten control animals (nos. 1-10) received an oral dose of corn oil.

Five of each group of ten rats were euthanased by means of $CO_2$ on day 2 with the remainder being euthanased by the same technique on day 8. The early-euthanased rats were numbers 6-10, 106-110 and 206-210. The late-euthanased rats were numbers 1-5, 101-105 and 201-205.

Pre- and post-dose urine samples were collected for 7 hours daily into ice-cooled vessels containing sodium azide (0.100 ml of a 10% (w/v) solution of sodium azide in water) as an antibacterial preservative. There was an additional overnight urine collection on the day of dosing (from 7-24 hours post-dose). The urine collection apparatus was cleaned prior to each collection to minimise bacterial, food and faecal contamination. The urine samples were deep-frozen pending NMR analysis.

Blood was sampled from the orbital sinus, under isoflurane anaesthesia. Blood was sampled from all animals on day −3 and just prior to euthanasia on either day 2 or day 8. Following euthanasia each rat was sampled for histopathological examination with the sampling including taking ten liver samples from each rat (two from each liver lobe). The blood samples were collected into vials containing lithium heparin as anticoagulant and immediately centrifuged at approx. minus four degrees C. to separate plasma. A portion of each plasma sample was analysed at thirty degrees C. on an AU600 multiparametric clinical analyser (Olympus) for a range of clinical chemistry parameters including alanine aminotransferase (ALT) and aspartate aminotransferase (AST) amongst many others.

Urine samples were prepared for NMR analysis by mixing 400 Eli of urine with 200 μl of phosphate buffer (an 81:19 (v/v) mixture of 0.2 M $Na_2HPO_4$ and 0.2 M $NaH_2PO_4$; pH 7.4); if insufficient urine was available the shortfall was made up with purified water with a minimum of 200 μl of urine being used. The urine-buffer mixture was left to stand for 10 minutes at room temperature to enable buffering to take place and then centrifuged at 13,000 rpm for a further 10 minutes to remove suspended particulates. 500 μl of 'clear' buffered urine was transferred to an NMR tube and 50 μl of a TSP/$D_2O$ solution added. TSP (sodium 3-trimethylsilyl-[2,2,3,3-$^2H_4$]-1-propionate) is a chemical shift reference compound (δ 0) used in the NMR experiment and the $D_2O$ provided a field/frequency lock for the NMR spectrometer. The concentration of the TSP/$D_2O$ solution was such as to give a final TSP concentration of 0.1 mM in the NMR tube. The NMR analyses were carried out at thirty degrees C. on a Bruker AMX 600 MHz NMR spectrometer with the NOESYPRESAT pulse sequence (Claridge, 1999) used to reduce the size of the water signal. The principal acquisition parameters were:

| | |
|---|---|
| Spectrometer Frequency: | 600 MHz |
| Spectral Width: | ca. 7200 Hz (12 ppm) |
| Bruker Pulse Program: | noesyprld |
| Number of Data Points in Time Domain: | 65536 |
| Number of Scans: | 64 |
| Number of Dummy Scans: | 4 |
| Acquisition Time: | ca. 4.55 seconds |
| Presaturation Time: | 3 seconds |
| Mixing Time: | 0.1 second. |

After acquisition, the NMR spectra were Fourier-transformed into 32768 data points following application of 0.3 Hz line-broadening by means of an exponential multiplication applied to the free induction decay signal. The spectra were phased to give an even baseline around the NMR signals and the chemical shift scale was set by assigning the value of δ 0 to the TSP peak. Prior to data-reduction, the baseline of each day −1 spectrum was moved to zero intensity using a straight-line baseline correction algorithm. All these spectral processing operations were carried out on a Silicon Graphics computer using the 'xwinnmr' software (Bruker GmBH).

Visual examination of the post-dose urine NMR spectra revealed great inter-animal variation in respect of the effects of galactosamine HCl (800 mg/kg) on endogenous metabolites (see Table 1.5 and FIGS. 1.3 and 1.4). On the basis of this visual examination, animals could be readily categorised as either (i) 'responders' or (ii) as 'weak or non-responders'. Additionally, the responders were found to excrete much greater amounts of galactosamine in their urine over the period from 0-24 hours post-dosing than did the weak/non-responders (see FIG. 1.1 and Table 1.6) and this indicates a connection between galactosamine metabolism and its toxicity.

FIG. 1.1 shows three NMR spectra. Spectrum 'a' is of the day 1 urine collected from animal 201 from 0-7 hours after dosing. Spectrum 'b' was obtained from authentic GaIN HCl. Spectrum 'c' is of the day 1 urine collected from animal 203 from 0-7 hours after dosing. Spectra 'a' and 'c' are scaled to constant allantoin (δ 5.4) peak height. GaIN is clearly present in the urine from animal 201 but not in the urine from animal 203.

Furthermore, in the NMR spectra of the urine samples collected from 24-31 hours post-dosing, the responders showed the presence of a certain N-acetyl peak that was, at least largely, absent from the spectra of the weak/non-responders (see FIG. 1.2). This peak was provisionally assigned to N-acetylgalactosamine. The great inter-animal variability in response to the 800 mg/kg dose was also reflected in the histopathology and clinical chemistry data (see Tables 1.2 to 1.4).

FIG. 1.2 shows NMR spectra of the day 2 urine samples collected from animals 202 (spectrum 'a') and 203 (spectrum 'b') from 24-31 hours after dosing. The spectra are sealed to constant creatinine. An N-acetylated species, believed to be N-acetylgalactosamine, is clearly present in spectrum 'a' but not in spectrum 'h'.

PCA was then carried out on the NMR spectra of the day −1 (pre-dose) urine samples for the animals that were subsequently dosed with galactosamine hydrochloride (800 mg/kg). This data set consisted of nine spectra because there was insufficient day −1 urine to obtain an NMR spectrum for animal 206. Prior to the PCA each day −1 spectrum was 'data-reduced' in a fixed manner using the 'AMIX' software (Bruker GmBH). Certain spectral regions were excluded with the retained regions being δ 9.0-δ 6.25 and δ 4.5-δ 2.76 and δ 2.48-δ 0.5. The retained regions were divided as far as possible into sequential 0.04 ppm-wide segments and an integral obtained for each segment of each spectrum. The data-reduced values were then normalised uniformly to give a total integration value of 1000 for each 'spectrum'. The resultant data set was loaded into a multivariate statistical analysis software package ('Pirouette' from Infometrix). The PCA was then carried out using mean-centred scaling for each variable. The resultant scores plots were colour-coded according to post-dose behaviour and, by inspection, it was found that the scores plot for PC1 versus PC5 gave separation of responders and non-responders. This plot and the corresponding loadings plot are presented as FIGS. 1.5 and 1.6 respectively. Examination of FIG. 1.5 suggests that an individual rat's response to dosing with galactosamine HCl (800 mg/kg) could be predicted from the appropriate pre-dose PCA scores plot depending on how it mapped in relation to known responders and non-responders. FIG. 1.6 demonstrates how such an analysis could reveal the pre-dose features that enable discrimination of responders and non-responders.

The various figures and tables that follow provide some details of the variable responses of the different rats to galactosamine HCl (800 mg/kg) and show how PCA can be used to distinguish responders and non-responders pre-dose. It is likely that a supervised PR method using PLS, PLS-DA or neural networks analysis would be able to achieve much better pre-dose discrimination of responders and non-responders than the unsupervised PR approach described here.

TABLE 1.2

Summary of histopathological changes in galactosamine HCl-dosed rats.

| | Dose of galactosamine hydrochloride | |
|---|---|---|
| Day | 200 mg/kg | 800 mg/kg |
| 2 | No differences from controls | Multifocal randomly scattered foci of hepatocellular necrosis were present in 4/5 animals. Severity of changes: 208 - none 207 - mild 206, 210 - marked 209 - severe Most necrotic hepatocytes were rounded with a deeply eosinophilic cytoplasm and pyknotic nucleus. Some degenerated hepatocytes showed fine cytoplasmic vacuolation. Necrotic foci and portal spaces were infiltrated by mixed inflammatory cells while foci of haemorrhage were occasionally seen. |
| 8 | No differences from controls | Minimal bile duct hyperplasia was found in 2/5 animals (201 and 202) this change being accompanied by slight hepatocellular anisocaryosis and a few scattered hemosiderin laden macrophages. |

TABLE 1.3

Clinical chemistry analysis of plasma sampled at 24 hours post-dosing.
See Table 1.4 for key to abbreviations and for units of measurement.

| STUDY | ANIMAL | 5'-NT | A/G | ALAT | ALB | AP | ASAT | TBA |
|---|---|---|---|---|---|---|---|---|
| 99023 | 6 | 23 | 1.4 | 51 | 34 | 635 | 82 | 69.0 |
| 99023 | 7 | 27 | 1.4 | 52 | 33 | 688 | 77 | 24.0 |
| 99023 | 8 | 21 | 1.3 | 62 | 33 | 732 | 103 | 29.0 |
| 99023 | 9 | 18 | 1.5 | 46 | 32 | 497 | 75 | 20.0 |
| 99023 | 10 | 26 | 1.5 | 50 | 34 | 492 | 86 | 16.0 |
| 99023 | 106 | 23 | 1.3 | 43 | 33 | 606 | 107 | 48.0 |
| 99023 | 107 | 21 | 1.4 | 46 | 33 | 495 | 84 | 22.0 |
| 99023 | 108 | 21 | 1.5 | 49 | 37 | 566 | 73 | 29.0 |
| 99023 | 109 | 19 | 1.4 | 38 | 34 | 697 | 67 | 23.0 |
| 99023 | 110 | 27 | 1.4 | 47 | 33 | 637 | 75 | 29.0 |
| 99023 | 206 | 156 | 1.7 | 2350 | 32 | 787 | 4320 | 493 |
| 99023 | 207 | 23 | 2.1 | 178 | 33 | 983 | 264 | 43.0 |
| 99023 | 208 | 17 | 1.5 | 45 | 34 | 666 | 79 | 20.0 |
| 99023 | 209 | 203 | 2.4 | 4300 | 33 | 999 | 10600 | 1300 |
| 99023 | 210 | 35 | 1.8 | 479 | 31 | 852 | 832 | 65.0 |

TABLE 1.3-continued

Clinical chemistry analysis of plasma sampled at 24 hours post-dosing.
See Table 1.4 for key to abbreviations and for units of measurement.

| STUDY | ANIMAL | BILI | CHOL | CREA | GGT | GLUC | PROT | TRIG | UREA |
|---|---|---|---|---|---|---|---|---|---|
| 99023 | 6 | 0.11 | 72 | 0.5 | 0 | 144 | 58 | 108 | 27 |
| 99023 | 7 | 0.09 | 77 | 0.4 | 0 | 186 | 56 | 93 | 23 |
| 99023 | 8 | 0.1 | 78 | 0.5 | 0 | 173 | 58 | 142 | 22 |
| 99023 | 9 | 0.1 | 70 | 0.5 | 0 | 185 | 53 | 130 | 31 |
| 99023 | 10 | | 62 | 0.5 | | 176 | 57 | 96 | 24 |
| 99023 | 106 | 0.09 | 73 | 0.5 | 0 | 173 | 59 | 94 | 29 |
| 99023 | 107 | 0.05 | 60 | 0.5 | 0 | 184 | 56 | 158 | 40 |
| 99023 | 108 | 0.11 | 91 | 0.5 | 0 | 167 | 61 | 140 | 33 |
| 99023 | 109 | 0.1 | 72 | 0.4 | 0 | 138 | 58 | 109 | 28 |
| 99023 | 110 | 0.12 | 81 | 0.5 | 0 | 182 | 57 | 127 | 28 |
| 99023 | 206 | 1.26 | 60 | 0.4 | 2 | 100 | 51 | 38 | 45 |
| 99023 | 207 | 0.06 | 15 | 0.4 | 0 | 162 | 49 | 89 | 24 |
| 99023 | 208 | 0.11 | 61 | 0.5 | 0 | 168 | 56 | 148 | 29 |
| 99023 | 209 | 1.37 | 42 | 0.4 | 5 | 80 | 47 | 95 | 40 |
| 99023 | 210 | 0.12 | 46 | 0.4 | 1 | 130 | 48 | 38 | 25 |

TABLE 1.4

Plasma chemistry abbreviations and units

| Abbreviation | Parameter | Units |
|---|---|---|
| 5-NT | 5-nucleotidase | IU/L |
| A/G | albumin/globulin ratio | none |
| ALAT | alanine aminotransferase | IU/L |
| ALB | albumin | g/L |
| AP | alkaline phosphatase | IU/L |
| ASAT | aspartate aminotransferase | IU/L |
| TBA | total bile acids | µmol/L |
| BILI | bilirubin | mg/dL |
| CHOL | total cholesterol | mg/dL |
| CREA | creatinine | mg/dL |
| GGT | γ-glutamyl transferase | IU/L |
| GLUC | glucose | mg/dL |
| PROT | total protein | g/L |
| TRIG | triglycerides | mg/dL |
| UREA | urea | mg/dL |

TABLE 1.5

Summary of urinary changes observed by NMR in galactosamine HCl-dosed rats. These results refer to the late-euthanased group of rats (animals 1-5, 101-105 and 201-205).

Dose of galactosamine hydrochloride

| 200 mg/kg | 800 mg/kg |
|---|---|
| Very variable amounts of galactosamine were present in the day 1 urine samples. | Very variable amount of galactosamine were present in the day 1 urine samples. The samples from animals 201 and 202 contained much galactosamine whilst the samples from animals 203-205 contained very little. See Table 1.6 and FIG. 1.1.<br>N-acetyl at ca. 2.07 ppm: this new peak was only apparent in the day 2 samples from animals 201 and 202. This peak was provisionally identified by addition of authentic standard as originating from N-acetylgalactosamine. |
| Taurine: some instances of raised taurine but no clear and consistent pattern. | Taurine: Animals 203-205 showed no clear change whilst animals 201 & 202 showed highly elevated levels. |
| Creatine: no increase | Creatine: Only animals 201 and 202 showed a clear increase in creatine - which occurred on day 3.<br>Guanidinoacetic acid: Only animals 201 and 202 showed a clear change in the level of GAA; both those animals showed very much increased levels on day 3 and perhaps somewhat low levels on day 7. |

TABLE 1.5-continued

Summary of urinary changes observed by NMR in galactosamine HCl-dosed rats. These results refer to the late-euthanased group of rats (animals 1-5, 101-105 and 201-205).
Dose of galactosamine hydrochloride

| 200 mg/kg | 800 mg/kg |
|---|---|
| | 2-Oxoglutarate: Animals 203-205 showed no obvious change in the level of 2-oxoglutarate. Animals 201 & 202 showed reduced levels on days 2 and 3 but very high levels on day 7. |
| | Trimethylamine-N-oxide: Animals 203-205 showed no obvious change in TMAO levels. Despite normal pre-dose levels, TMAO had essentially disappeared from the day 3 urine samples obtained from animals 201 & 202. |
| | Bile acids: clearly increased (seen as C18 methyl) in the day 3 samples from animals 201 and 202. |
| | Betaine: appeared very clearly in the day 2 and day 3 samples from animals 201 & 202 and some betaine was still present in the day 7 samples from those two animals. No betaine was detected in any of the urine samples from animals 204-205. A tiny amount of betaine was possibly present in the day 3 sample from animal 203. |
| | Urocanic acid: appeared clearly in the day 2 and day 3 samples from animals 201 and 202 but was not present in any other samples. |
| | Histidine: appeared very clearly in the day 3 sample from animal 201 and less clearly in the day 3 sample from animal 202. Histidine was not present in any of the other urine samples examined from the high dose group. |
| | Threonine: was very clearly elevated in the day 3 samples from animals 201 and 202. Threonine levels appeared to be normal in all the other high dose samples. |
| | Alanine: was clearly elevated in the day 3 samples from animals 201 and 202 but was otherwise normal. |
| | Glucose: appeared to be elevated in the day 2 and day 3 urine samples from animals 201 and 202. Occasionally elevated glucose was shown by other high dose animals (animal 204 on day 3; animal 205 on day 7). |
| | A doublet at ca. δ 5.21, arising from an unidentified compound, was clearly present in the day 2 urine spectra from animals 201 & 202. This doublet was not clearly visible in the spectra of any urine samples from animals 201-205. |
| | Hippurate: was depleted in the day 3 samples from animals 201 and 202. |
| | Glutamate and glutamine were elevated in the day 3 urine spectrum from animal 201 and possibly also elevated in the day 3 urine spectrum from animal 202. |
| | Other unlisted changes occurred. |

FIG. 1.3 shows a portion of the noesypresat NMR spectra of the day −1 and day +3 urine samples from animal 202. The pre-dose sample (spectrum 'a') was collected from 24-17 hours before dosing. The post-dose sample (spectrum 'b') was collected from 48-55 hours post-dosing. The spectra are scaled to constant creatinine. In comparison to spectrum 'a', spectrum 'b' shows increases in creatine, betaine, guanidinoacetic acid (GAA) and taurine and decreases in trimethylamine-N-oxide (TMAO) and 2-oxoglutarate.

FIG. 1.4 shows a portion of the noesypresat NMR spectra of the day −1 and day +3 urine samples from animal 201. The pre-dose sample (spectrum 'a') was collected from 24-17 hours before dosing. The post-dose sample (spectrum 'b') was collected from 48-55 hours post-dosing. The spectra are scaled to constant allantoin. In comparison to spectrum 'a', spectrum 'b' shows increased excretion of histidine and decreased excretion of hippurate.

TABLE 1.6

The variability of response to galactosamine HCl (800 mg/kg) in relation to the amount of galactosamine excreted in the urine. This table shows, for each animal, the amount of galactosamine excreted in the urine collected from 0-24 hours post-dosing and lists whether or not a toxic response was observed.

| Animal Number | Total amount of galactosamine excreted in the urine from 0-24 hours post-dosing (mg) | Responder (R) or non-responder (NR) | Source of evidence regarding R/NR classification |
|---|---|---|---|
| 201 | 40.0 | R | Urine NMR, Histopathology |
| 202 | 26.2 | R | Urine NMR, Histopathology |
| 203 | 0.4 | NR | Urine NMR, Histopathology |
| 204 | 0.1 | NR | Urine NMR, Histopathology |

TABLE 1.6-continued

The variability of response to galactosamine HCl (800 mg/kg) in relation to the amount of galactosamine excreted in the urine. This table shows, for each animal, the amount of galactosamine excreted in the urine collected from 0-24 hours post-dosing and lists whether or not a toxic response was observed.

| Animal Number | Total amount of galactosamine excreted in the urine from 0-24 hours post-dosing (mg) | Responder (R) or non-responder (NR) | Source of evidence regarding R/NR classification |
| --- | --- | --- | --- |
| 205 | 0.3 | NR | Urine NMR, Histopathology |
| 206 | 14.9 | R | Histopathology |
| 207 | 8.4 | NR (or weak R) | Histopathology |
| 208 | 2.3 | NR | Histopathology |
| 209 | 28.2 | R (severe) | Histopathology |
| 210 | 30.5 | R | Histopathology |

The measured amount of galactosamine excreted by animal 206 was somewhat lower than expected, given that it was a strong responder, and this may be because of urine retained in the bladder. Only 3.7 ml of urine was excreted by animal 206 over the period from 0-24 hours post-dosing and this was the lowest amount of urine produced by any animal during that period. Metabolite excretion is most likely to be underestimated when the measured urine volume is very low; this is because there may be a significant amount of highly concentrated urine in the bladder which is insufficient to cause urination.

FIG. 1.5 shows a PC scores plot obtained by PCA of the $^1$H NMR spectra of the nine available day −1 urine samples for the high dose (800 mg/kg) animals; insufficient day −1 urine was available to obtain an NMR spectrum for animal 206. The data points are coded using diamonds for non-responders (animal nos. 203, 204, 205, 207 and 208) and crosses for responders (animal nos. 201, 202, 209, 210), but it should be noted that animal 207 was on the borderline between responder and non-responder. This plot shows that there are features in the pre-dose urine spectra which can distinguish between those animals which will and will not be badly affected by galactosamine 800 mg/kg. The responders had higher pre-dose levels of urinary creatine than non-responders and all but one of the responders (animal 201) had a lower pre-dose ratio of urinary 2-oxoglutarate/creatinine than non-responders (see also FIG. 1.6).

Each of the plotted points of FIG. 1.6 is labelled according to the centre of the 0.04 ppm-wide spectral segment that it represents. Thus, for instance, the point labelled 3.02 represents the spectral segment (or variable) from δ 3.04 to δ 3.00 ppm. The points of interest are those that make substantial, non-zero, contributions to PCs 1 and 5. Comparison of FIGS. 1.5 and 1.6 indicates that, in comparison to the responders, the non-responders have a relatively high value for the integral of the spectral segment centred at δ 3.02. This difference appears to be attributable to a higher level of 2-oxoglutarate in the non-responders and 2-oxoglutarate also contributes to the segment centred at δ 2.46. Trimethylamine-N-oxide makes a major contribution to the segment centred at δ 3.26 and non-responders could therefore have high urinary levels of TMAO. One possible explanation for this is that the non-responders were slow acetylators.

Example 2

Variable Urinary Isoniazid Metabolite Patterns and their Relationship to The Toxicity of Isoniazid in Rats An example of the major significance of inter-individual differences in metabolic capacities.

Thirty young adult age-matched male Sprague-Dawley rats were obtained from Charles River, France. After observation to ensure that they each appeared healthy they were placed in individual metabolism cages with free access to water and a standardised diet (diet. AO4C from Usine d'Alimentation Rationnelle, Villemoisson-sur-Orge, France). The laboratory temperature was maintained at 20±2 degrees C. and the relative humidity at 60±20%. The laboratory air was filtered and changed 14 times per hour. A fixed '12 hours light-12 hours dark' cycle was imposed. The study commenced after a short period of cage 'acclimatisation' when the rats were about 6 weeks old and about 200 g in mass.

Dosing was on the day designated as 'day 1' when the growing rats were each approximately 250 g in mass. Isoniazid (from Sigma, France) was dissolved in physiological saline and dosed by intraperitoneal injection at either 200 mg/kg or at 400 mg/kg; ten animals (nos. 101-110) received the low dose and ten animals (nos. 201-210) received the high dose. Ten control animals (nos. 1-10) received an intraperitoneal injection of saline.

Pre- and post-dose seven hour urine samples were collected daily into ice-cooled vessels containing sodium azide (0.1 ml of a 10% (w/v) solution of sodium azide in water) as an antibacterial preservative. There was an additional overnight urine collection from 7-24 hours post-dosing. The urine collection apparatus was cleaned prior to each collection to minimise bacterial, food and faecal contamination. The final volume of each urine sample was determined without making any correction for the azide solution. The urine samples were stored frozen pending analysis.

It was intended that post-dose blood samples would be taken immediately before euthanasia with euthanasia being immediately followed by sampling for histopathology. As in Example 1, the intention was that five of each group of ten rats would be euthanased by means of $CO_2$ at one day after dosing thereby providing early blood and histopathology samples; the remainder were to be euthanased by the same technique at seven days after dosing thereby providing late blood and histopathology samples. It was planned that the early-euthanased rats would be numbers 6-10, 106-110 and 206-210 whilst the late-euthanased rats would be numbers 1-5, 101-105 and 201-205. However, some animals (nos. 204, 205, 207 and 209) from the group which received the high dose of isoniazid, suffered unexpected convulsions and either died or had to be euthanased early to prevent suffering. Remarkably, by comparison, the other animals (nos. 201-203, 206, 208 and 210) from the high dose group showed no obvious clinical signs of ill effects. The urine samples were deep-frozen pending NMR analysis.

Urine samples were prepared for NMR analysis by mixing 4001 μl of urine with 200 μl of phosphate buffer (an 81:19 (v/v) mixture of 0.2 M $Na_2HPO_4$ and 0.2 M $NaH_2PO_4$); if insufficient urine was available the shortfall was made up with purified water with a minimum of 200 μl of urine being used. The urine-buffer mixture was left to stand for 10 minutes at room temperature to enable buffering to take place and then centrifuged at 13,000 rpm for a further 10 minutes to remove suspended particulates, 500 µl of 'clear' buffered urine was transferred to an NMR tube and 50 µl of a TSP/D$_2$O solution added. TSP (sodium 3-trimethylsilyl-[2,2,3,3-$^2$H$_4$]-1-propionate) is a chemical shift reference compound (δ 0) used in the NMR experiment and the D$_2$O provided a field/frequency lock for the NMR spectrometer. The concentration of the TSP/D$_2$O solution was such as to give a final TSP concentration of 0.1 mM in the NMR tube. The NMR analyses were carried out at 303K on a Bruker AMX 600 MHz NMR spectrometer with the NOESYPRESAT pulse sequence (Claridge, 1999) used to reduce the size of the water signal. The principal acquisition parameters were:

| | |
|---|---|
| Spectrometer Frequency: | 600 MHz |
| Spectral Width: | ca. 7200 Hz (12 ppm) |
| Bruker Pulse Program: | noesyprld |
| Number of Data Points in Time Domain: | 65536 |
| Number of Scans: | 64 |
| Number of Dummy Scans: | 4 |
| Acquisition Time: | ca. 4.55 seconds |
| Presaturation Time: | 3 seconds |
| Mixing Time: | 0.1 second. |

After acquisition the NMR spectra were Fourier-transformed into 32768 data points following application of 0.3 Hz line-broadening by means of an exponential multiplication applied to the free induction decay signal. The spectra were phased to give an even baseline around the NMR signals and the chemical shift scale was set by assigning the value of δ 0 to the TSP peak. Spectra and selected expansions were plotted on paper. Where a set of spectra was to be examined by multivariate pattern recognition methods, the baseline of each spectrum was moved to zero intensity using a straight-line baseline correction algorithm. These spectral processing operations were carried out on a Silicon Graphics computer using the 'xwinnmr' software (Bruker GmBH).

Visual examination of the NMR spectra collected from 0-7 hours post-dosing revealed substantial variation in the patterns of certain metabolites which are believed to be derived from isoniazid. This variation was particularly obvious in three peaks in the region of 2 ppm which are thought to originate from three different N-acetylated species. These peaks at ca. 2.22, 2.20 and 2.15 ppm are henceforth designated as peaks 'a', 'b' and 'c' respectively and the compounds from which they arise are henceforth designated as compounds 'A', 'B' and 'C'. At each dose there appeared to be essentially two different types of pattern of these metabolites and examples of these different patterns, referred to as Type 1 and Type 2, are shown in FIG. 2.1.

PCA of the data-reduced NMR spectra of the urine samples collected from 0-7 hours after dosing isoniazid (200 mg/kg) also revealed the metabolic variation (see FIG. 2.2). To achieve this analysis the NMR spectra of the nine available samples were first 'data-reduced' in a fixed manner using the AMIX program (Bruker GmBH). All spectral regions except for the N-acetyls region from δ 2.23 to δ 2.13 were discarded. The remaining portion of each spectrum was divided into two consecutive 0.05 ppm-wide segments and an integral obtained for each segment. The data-reduced values were then normalised to give a total integration value of 1000 for each 'spectrum'. The resultant data set was loaded into a multivariate statistical analysis software package ('Pirouette' from Infometrix) and Principal Components Analysis (PCA) carried out using mean-centred scaling of each variable (spectral segment). With only two input variables this was a trivial example of PCA but it supported the presence of two different types of N-acetyls patterns as previously determined, the Type 1 animals being animals 101, 103 and 109 and the Type 2 animals being animals 102, 105, 106, 107, 108 and 110. In FIG. 2.2 the data points for the Type 1 animals are marked with crosses whilst the data points for the Type 2 animals are marked with diamonds.

Isoniazid is a classic example of a substance whose metabolism, in humans, is affected by N-acetylator phenotype and the different metabolite patterns that were observed in this example suggested the existence of slow and fast N-acetylators within the test group. The isoniazid metabolite patterns were somewhat dose-dependent but it was possible, regardless of dose level, to assign all the day 1 (0-7 hours) urine spectra as having either Type 1 or Type 2 patterns on the basis of fixed peak height ratio criteria (see Table 2.1). Remarkably it was observed, at the high dose level, that only those animals showing the Type 2 pattern of N-acetyls developed certain toxic responses which included loss of kidney function (revealed by increased urinary glucose and/or lactate), convulsions and death (see Table 2.1).

TABLE 2.1

Summary of the metabolic and other behaviour observed after dosing isoniazid to male Spague-Dawley rats at 200 and 400 mg/kg.

Table 2.1, part 1.

| Animal No. | Dose (mg/kg) | a = 2.22 ppm pk. ht. | b = 2.20 ppm pk. ht. | c = 2.15 ppm pk. ht. |
|---|---|---|---|---|
| 101 | 200 | 5 | 30 | 66.5 |
| 102 | 200 | 14 | 62.5 | 75 |
| 103 | 200 | 3 | 22 | 49 |
| 104 | 200 | no spectrum | no spectrum | no spectrum |
| 105 | 200 | 14.5 | 101 | 82.5 |
| 106 | 200 | 18.5 | 79 | 110 |
| 107 | 200 | 12 | 42 | 44.5 |
| 108 | 200 | 41 | 140 | 101 |
| 109 | 200 | 6 | 29 | 89 |
| 110 | 200 | 17 | 70 | 47.5 |
| 201 | 400 | 9 | 44 | 65.5 |
| 202 | 400 | 10 | 48 | 76.5 |
| 203 | 400 | 9.5 | 49 | 72 |
| 204 | 400 | 21.5 | 99.5 | 28.5 |
| 205 | 400 | 12.5 | 68 | 14 |
| 206 | 400 | 45 | 157 | 69.5 |
| 207 | 400 | 34 | 113 | 25 |
| 208 | 400 | 14 | 81 | 114.5 |
| 209 | 400 | 34 | 128 | 31.5 |
| 210 | 400 | 6.5 | 41 | 77 |

The peak heights (abbreviated pk.ht.) were measured in millimetres from the plotted spectra after subtraction of a local baseline.

Table 2.1, part 2.

| Animal No. | Dose (mg/kg) | c/b pk. ht. ratio | c/a pk. ht. ratio | Acetyls type |
|---|---|---|---|---|
| 101 | 200 | 2.2 | 13.3 | 1 |
| 102 | 200 | 1.2 | 5.4 | 2 |
| 103 | 200 | 2.2 | 16.3 | 1 |
| 104 | 200 | no spectrum | no spectrum | no spectrum |
| 105 | 200 | 0.8 | 5.7 | 2 |
| 106 | 200 | 1.4 | 5.9 | 2 |
| 107 | 200 | 1.1 | 3.7 | 2 |
| 108 | 200 | 0.7 | 2.5 | 2 |
| 109 | 200 | 3.1 | 14.8 | 1 |
| 110 | 200 | 0.7 | 2.8 | 2 |
| 201 | 400 | 1.5 | 7.3 | 1 |
| 202 | 400 | 1.6 | 7.7 | 1 |
| 203 | 400 | 1.5 | 7.6 | 1 |
| 204 | 400 | 0.3 | 1.3 | 2 |
| 205 | 400 | 0.2 | 1.1 | 2 |

TABLE 2.1-continued

| | | | | |
|---|---|---|---|---|
| 206 | 400 | 0.4 | 1.5 | 2 |
| 207 | 400 | 0.2 | 0.7 | 2 |
| 208 | 400 | 1.4 | 8.2 | 1 |
| 209 | 400 | 0.2 | 0.9 | 2 |
| 210 | 400 | 1.9 | 11.8 | 1 |

Criteria for determination of N-acetyls pattern type:
Low dose: Type 1: c/b ≥ 2.2; c/a ≥ 13.3    Type 2: c/b ≤ 1.4; c/a ≤ 5.9
High dose: Type 1: c/b ≥ 1.4; c/a ≥ 7.3    Type 2: c/b ≤ 0.4; c/a ≤ 1.5
Either    Type 1: c/a ≥ 7.3                Type 2: c/a ≤ 5.9
dose:     Type 1: c/b ≥ 1.4                Type 2: c/b ≤ 1.4

Table 2.1, part 3. No loss of kidney function was detected at the 200 mg/kg dose but some animals showed impaired kidney function at the 400 mg/kg dose. Furthermore, there is a correlation, at the 400 mg/kg dose, between the type of acetyls pattern observed and whether or not there was any loss of kidney function. Only the Type 2 animals showed a loss of kidney function as evidenced by increased urinary levels of glucose and lactate. As an animal producing the Type 2 acetyls pattern, animal 206 showed somewhat anomalous behaviour in regard to urinary lactate. However, it is noteworthy that this animal was at the extreme edge of Type 2 region as defined by the acetyls peak height ratios.
Table 2.1 part 3

| Animal No. | Dose (mg/kg) | Acetyls type | Increased lactate? | Increased glucose? |
|---|---|---|---|---|
| 101 | 200 | 1 | No | No |
| 102 | 200 | 2 | No | No |
| 103 | 200 | 1 | No | No |
| 104 | 200 | no spectrum | no spectrum | no spectrum |
| 105 | 200 | 2 | No | No |
| 106 | 200 | 2 | No | No |
| 107 | 200 | 2 | No | No |
| 108 | 200 | 2 | No | No |
| 109 | 200 | 1 | No | No |
| 110 | 200 | 2 | No | No |
| 201 | 400 | 1 | No | No |
| 202 | 400 | 1 | No | No |
| 203 | 400 | 1 | No | No |
| 204 | 400 | 2 | Yes | Yes |
| 205 | 400 | 2 | Yes | Yes |
| 206 | 400 | 2 | No | Yes |
| 207 | 400 | 2 | Yes | Yes |
| 208 | 400 | 1 | No | No |
| 209 | 400 | 2 | Yes | Yes |
| 210 | 400 | 1 | No | No |

Table 2.1, part 4. There is a further association, at the 400 mg/kg dose, between the type of acetyls pattern observed and whether or not convulsions and premature death occurred. Only Type 2 animals suffered convulsions and premature death. Again animal 206 was anomalous in that it was Type 2 but did not die prematurely.

| Animal No. | Dose (mg/kg) | Acetyls type | Impaired kidney function? | Premature Death? |
|---|---|---|---|---|
| 101 | 200 | 1 | No | No |
| 102 | 200 | 2 | No | No |
| 103 | 200 | 1 | No | No |
| 104 | 200 | no spectrum | no spectrum | No |
| 105 | 200 | 2 | No | No |
| 106 | 200 | 2 | No | No |
| 107 | 200 | 2 | No | No |
| 108 | 200 | 2 | No | No |
| 109 | 200 | 1 | No | No |
| 110 | 200 | 2 | No | No |
| 201 | 400 | 1 | No | No |
| 202 | 400 | 1 | No | No |
| 203 | 400 | 1 | No | No |
| 204 | 400 | 2 | Yes | Yes |
| 205 | 400 | 2 | Yes | Yes |
| 206 | 400 | 2 | Yes (mild) | No |
| 207 | 400 | 2 | Yes | Yes |
| 208 | 400 | 1 | No | No |
| 209 | 400 | 2 | Yes | Yes |
| 210 | 400 | 1 | No | No |

Table 2.1 suggests that some metabolic difference, reflected in the N-acetyls patterns, has a critical effect on isoniazid toxicity. The critical metabolic step is suspected to be the initial transformation of isoniazid which may proceed either 1) to N-acetylisoniazid, by N-acetylation, or 2) to hydrazine and isonicotinic acid, by hydrolysis of the amide group of isoniazid (see FIG. 2.3).

We suspect that hydrazine was responsible for the observed convulsions and we postulate that the animals showing the toxic responses in this study had a particular N-acetylator phenotype i.e. that they were relatively slow N-acetylators and that they therefore produced more toxic hydrazine from the 400 mg/kg dose of isoniazid than did the other high dose animals which were presumably relatively fast N-acetylators. To confirm the nature of the factor(s) underlying the variable effects of isoniazid (400 mg/kg) that were observed in this study, compounds 'A' and 'B' giving rise to peaks 'a', 'b' must be identified. Compound 'C' has already been identified as N-acetylisoniazid.

This example demonstrates, as is well known, that the metabolite patterns of a dosed substance can be used to distinguish different metabolic phenotypes. This example also shows that these metabolite patterns may be interrogated by the use of PR methodology. This example also demonstrates the crucial importance of metabolic phenotype in determining an individual's response to being dosed with a particular substance. In the next example it is demonstrated that the present invention allows variation in post-dose metabolic behaviour to be correlated with pre-dose variation in biological samples so as to provide a predictive model.

Example 3

Pre-Dose Prediction of Urinary Isoniazid Metabolite Quantities in Male Sprague-Dawley Rats Subsequently Dosed with Isoniazid (200 mg/kg)

An example showing that numerical pre-dose to post-dose predictions can be achieved.

75 young adult age-matched male Sprague-Dawley rats were obtained from Charles River, France. After screening to ensure that they appeared healthy they were assigned numbers 101-175 and placed in individual metabolism cages with free access to water and a standardised diet (diet AO4C from Usine d'Alimentation Rationnelle, Villemoisson-sur-Orge, France). The laboratory temperature was maintained at 20±2 degrees C. and the relative humidity at 60±20%. The laboratory air was filtered and changed 14 times per hour. A fixed '12 hours light-12 hours dark' cycle was imposed. The study commenced after a short period of cage 'acclimatisation' when the rats were about 6 weeks old and about 200 g in mass. Dosing was carried out when the growing rats were each approximately 250 g in mass. Isoniazid (from Sigma, France) was dissolved in physiological saline and dosed to each rat by intraperitoneal injection at 200 mg/kg.

Individual pre-dose (48-41 hours before dosing) and post-dose (0-7 hours after dosing) urine samples were collected into ice-cooled vessels containing sodium azide (0.1 ml of a 10% (w/v) solution of sodium azide in water) as an antibacterial preservative. The urine collection apparatus was cleaned prior to each collection to minimise bacterial, food and faecal contamination. The final volume of each urine sample was determined without making any correction for the azide solution.

The urine samples were prepared for NMR analysis by mixing 400 μl of urine with 200 μl of phosphate buffer (an 81:19 (v/v) mixture of 0.2 M $Na_2HPO_4$ and 0.2 M $NaH_2PO_4$;

pH 7.4); if insufficient urine was available the shortfall was made up with purified water with a minimum of 200 µl of urine being used. The urine-buffer mixture was left to stand for 10 minutes at room temperature to enable buffering to take place and then centrifuged at 13,000 rpm for a further 10 minutes to remove suspended particulates. 500 µl of 'clear' buffered urine was transferred to an NMR tube and 50 µl of a TSP/D$_2$O solution added. TSP (sodium 3-trimethylsilyl-[2,2,3,3-$^2$H$_4$]-1-propionate) is a chemical shift reference compound ($\delta$ 0) used in the NMR experiment and the D$_2$O provided a field/frequency lock for the NMR spectrometer. The concentration of the TSP/D$_2$O solution was such as to give a final TSP concentration of 0.1 mM in the NMR tube.

The NMR analyses of the prepared urine samples were carried out at thirty degrees C. on Bruker 600 MHz NMR spectrometers with the NOESYPRESAT pulse sequence (Claridge, 1999) used to reduce the size of the water signal. A Bruker DRX spectrometer was used to acquire the post-dose NMR data whilst a Bruker AMX spectrometer was used to acquire the pre-dose NMR data. The principal acquisition parameters were:

| | |
|---|---|
| Spectrometer Frequency: | 600 MHz |
| Spectral Width: | ca. 7200 Hz (12 ppm) |
| Bruker Pulse Program: | noesyprld |
| Number of Data Points in Time Domain: | 65536 |
| Number of Scans: | 32 (post-dose spectra); 64 (pre-dose spectra) |
| Number of Dummy Scans: | 4 |
| Acquisition Time: | ca. 4.55 seconds |
| Presaturation Time: | 3 seconds |
| Mixing Time: | 0.1 second. |

After acquisition the NMR spectra were Fourier-transformed into 32768 data points following application of 0.3 Hz line-broadening by means of an exponential multiplication applied to the free induction decay signal. The spectra were phased to give an even baseline around the NMR signals and the chemical shift scale was set by assigning the value of $\delta$ 0 to the TSP peak. Each of the post-dose NMR spectra was plotted on paper and peak height measurements were made manually on selected peaks after localised baseline correction. The peaks whose heights were measured were the allantoin peak at $\delta$ 5.4, the three peaks at ca. $\delta$ 2.22, $\delta$ 120 and $\delta$ 2.15, known as peaks 'a', 'b' and 'c' respectively as in Example 2, and the TSP peak at $\delta$ 0. Prior to data reduction leading to multivariate statistical analysis, the baseline of each digital spectrum was moved to zero intensity using a straight-line baseline correction algorithm. The spectral processing and plotting operations described above were carried out on a Silicon Graphics computer using the 'xwinnmr' software (Bruker GmBH).

After data reduction, PCA of the 'N-acetyls' region ($\delta$ 2.3 to $\delta$ 2.1) of the post-dose NMR spectra was carried out using the 'Pirouette' software from Infometrix. However, in contrast to the results for Example 2, distinct groupings for Type 1 and Type 2 spectra were not observed despite the wide range of patterns present in the data set. As it was not possible to identify suitable natural boundaries within the distribution, the individual post-dose spectra were better described by numerical measures rather than by membership of a particular class. This in turn meant that the following pre-dose to post-dose correlation analysis would be better based on numerical prediction rather than on class prediction.

There are certain problems associated with achieving useful measurements of urinary metabolite excretion and, consequently, two different approaches were taken to quantifying the excretion of the different N-acetylated species in the post-dose samples. The first approach was to quantify the excretion of metabolites A, B and C (designated as in Example 2) with respect to an endogenous urinary component, allantoin. Thus, the intensities of peaks a, b and c in each NMR spectrum were described as peak height ratios with respect to the allantoin peak at $\delta$ 5.4. The allantoin peak was a convenient internal reference point although the creatinine methylene signal at $\delta$ 4.05 could also have been used for that purpose. The second approach was to make some measure of the absolute excretion of components A, B and C by reference to the size of the TSP signal, which was added in known constant quantity to each NMR sample, and taking into account the volume of urine produced by each rat. Thus, for example, a relative measure of the absolute excretion of compound C by different animals was obtained using the formula (height of peak 'c'/ height of TSP peak)*(volume of urine collected). It is important to note here that this measurement is valid because all of the post-dose NMR samples were prepared in a constant fashion using 400 µl of urine except for animal 138 where no urine was available and no NMR sample was prepared. Peak heights were measured in millimeters and urinary volumes were measured in milliliters. The limitation of this second approach is that the urine collected from an animal over a set period may not be representative of what was passed to the bladder during that period and experience has shown that such excretion 'errors' are particularly likely when very little urine is collected. The limitation of the first approach to quantitation is that the excretion of the endogenous reference compound, allantoin in this case, may not be invariant although prior experience has indicated it to be a useful reference point.

Each pre-dose NMR spectrum was 'data-reduced' in a constant fashion using the AMIX program (Bruker GmBH). Certain spectral regions were discarded (e.g. the regions containing the TSP and residual water signals) before dividing the remainder of each spectrum into sequential 0.04 ppm-wide segments and obtaining an integral for each segment. The data-reduced spectra were then normalised to give the same total intensity for each 'spectrum'. PLS analyses were then carried out in an attempt to find pre-dose features that would enable prediction of the post-dose excretion of the various N-acetylated metabolites, 'A', 'B' and 'C'. These PLS analyses were carried out using the SIMCA software from Umetrics.

It was found that, for certain animals, the heights of peaks 'a' and 'b', relative to the height of the allantoin peak at $\delta$ 5.4, in the NMR spectra of the urine samples collected from 0-7 hours after dosing isoniazid (200 mg/kg), could be predicted surprisingly well from the pre-dose data (see FIGS. 3.1 and 3.2 which relate to peak 'a'). Considering the case of peak 'a', its peak height ratio with respect to allantoin provides a relative measure of the ratio of (amount of compound A/amount of allantoin) in the NMR sample. If allantoin excretion over the 7 hour urine collection period on day 1 is assumed to be constant for all the rats in this study, the ratio (height of peak 'a'/height of allantoin peak) provides a relative measure of the amounts of compound A excreted by the different rats during that period. Thus, these findings indicate that, with a suitable model, the amounts of compounds A and B excreted after dosing isoniazid (200 mg/kg) are predictable, for some rats, from the pre-dose data.

It was also found that, for the vast majority of animals that produced more than 3 ml of urine during the 0-7 hour collection period on day 1, the quantity (height of peak 'c'/height of TSP peak)*(volume of urine collected) could be predicted from the pre-dose data (see FIG. 3.3). Given that the NMR samples and associated spectra were all prepared and obtained in the exact same way, this quantity is a relative measure of the amount of compound C excreted by each rat. Thus, with a suitable model, it is possible to predict, from pre-dose data, the amount of compound C excreted after dosing isoniazid (200 mg/kg).

FIG. 3.1 shows the model building and validation data for a PLS model predicting, from pre-dose urinary NMR spectroscopic data, the values of (height of peak 'a'/height of allantoin peak) in the NMR spectra of urine samples collected from 0-7 hours after dosing isoniazid (200 mg/kg) to male Sprague-Dawley rats. The data points are marked and coded using unfilled triangles for model building data and filled triangles for validation data. The unfilled triangles show the observed and predicted results for the rats whose data was used to build the predictive PLS model. The filled triangles show the observed and predicted results for eleven rats (numbers 110, 111, 122, 125, 128, 135, 140, 144, 147, 167 and 172) whose data were excluded from the model-building process. Visual assessment of this figure indicates that a valid model has been obtained and that it is possible to predict the level of excretion of peak 'a' relative to the level of allantoin from an analysis of the pre-dose data.

The regression coefficients pertaining to the PLS analysis of FIG. 3.1 are shown in FIG. 3.2 for each of the variables used in the analysis. As previously described, these variables were derived from integrals of consecutive segments of the pre-dose spectra. The different variables used in the PLS analysis are identified, in FIG. 3.2, according to the chemical shift at the centre of the relevant 0.04 ppm-wide spectral segments. The greater the magnitude, either positive or negative, of the regression coefficient for a spectral segment, the greater the predictive contribution of that segment and, for example, the pre-dose spectral segment centred at $\delta$ 3.42 is negatively correlated with the concentration of A post-dose.

FIG. 3.3 shows the model building and validation data for a PLS model predicting, from pre-dose urinary NMR spectroscopic data, the post-isoniazid (200 mg/kg) excretion of compound C by Sprague-Dawley rats. The data points in FIG. 3.3 are marked and coded using unfilled triangles for model building data and tilled triangles for validation data. The unfilled triangles show the observed and predicted values for the various rats whose data was used in building the model. The filled triangles show the observed and predicted results for eight rats (numbers 105, 108, 115, 116, 121, 142, 157 and 163) whose data were excluded from the model-building process. The relative amount of metabolite C excreted by each animal was measured as (height of peak 'c'/height of TSP peak)*(volume of urine produced). Visual assessment of this figure indicates that a valid model has been obtained.

In a further analysis of the data, a different approach was taken to the quantitation of the compounds A, B and C that were excreted after dosing isoniazid. In this approach the region from $\delta$ 2.24-2.12, containing the three peaks 'a', 'b' and 'c', was first integrated as a whole. Then separate integrations for the regions $\delta$ 2.24-2.17 (containing peaks 'a' and 'b') and $\delta$ 2.17-2.12 (containing peak 'c') were obtained as fractions of the total $\delta$ 2.24-2.12 integration, giving 'Fraction A+B' and 'Fraction C'. The ratio [Fraction C/(Fraction A+B)] was then calculated from the latter two quantities. The rationale for this approach was that integrations should provide better estimates of relative amounts than are obtainable from peak height measurements, whilst recognising that the individual ratios (Amount C/Amount A) and (Amount C/Amount B), that provided phenotypic discrimination, might be usefully replaced by the single ratio [Fraction C/(Fraction A+B)]. Knowledge of either Fraction A+B or Fraction C means that the ratio [Amount C/(Amount A+Amount B)] can be calculated. Thus, using the SIMCA software from Umetrics, we attempted to build PLS models for predicting Fraction A+B, Fraction C and [Fraction C/(Fraction A+B)] from the pre-dose data. This gave three possible ways of arriving at a successful prediction of [Fraction C/(Fraction A+B)].

Using pre-dose NMR data normalised to constant total spectral area (after excluding certain spectral regions), we found that PLS models were obtained that were successful in individually predicting each of the three quantities, Fraction A+B, Fraction C and the ratio [Fraction C/(Fraction A+B)], from that pre-dose data.

FIG. 3.4 shows a plot of the observed versus pre-dose predicted values for [Fraction C/(Fraction A+B)] in the urine collected from 0-7 hours after dosing male Sprague-Dawley rats with isoniazid (200 mg/kg). The results shown are for modelling data only. This plot indicates that correlation between the pre- and post-dose data can be detected.

FIG. 3.5 shows the results of the internal model validation analysis proving that the observed correlation between the pre-dose data and the post-dose values of [Fraction C/(Fraction A+B)] was not random.

FIG. 3.6 shows the prediction of [Fraction C/(Fraction A+B)] for an externally generated test set. In this case a pre-to-post dose prediction model built using the present isoniazid study data was used in an attempted pre-to-post dose prediction of the results for 9 low dose animals from the isoniazid study described in Example 2. The prediction set (filled circles) was comprised of six Type 2 animals and three Type 1 animals and the results showed that [Fraction C/(Fraction A+B)] could be successfully predicted for the Type 2 test animals but was not well predicted for the Type 1 test animals (RMSEE=0.1524; RMSEP (Types 1 and 2)=0.4416; RMSEP (Type 2)=0.2325). However, examination of the modelling data (unfilled circles) indicated that it was almost entirely composed of Type 2 animals and this provides a likely explanation why Type 2 test data could be better predicted than Type 1. However, it is important to note that the model was sufficiently robust to provide some useful predictions for test data obtained in a separate study.

With further work it may prove possible to make pre-dose predictions of susceptibility or non-susceptibility to isoniazid (400 mg/kg)-induced toxicity as seen in Example 2. However, the crucial result obtained here is that certain metabolic phenotype-determined post-dose results can be predicted from pre-dose biofluid NMR spectra.

Example 4

Pre-Dose Prediction of Urinary Paracetamol Metabolite Quantities in Male Sprague-Dawley Rats Subsequently Dosed with Paracetamol (600 mg/kg)

An example showing that numerical pre-dose to post-dose predictions can be achieved.

75 male Sprague-Dawley rats were obtained which were matched for age and body mass. At 3 days before dosing the mean body mass of the rats was 260.2 g (standard deviation: 12.6 g) and at the time of dosing the rats were approximately 7 weeks old. They were kept in individual cages in a temperature-, humidity- and light/dark-controlled laboratory with free access to water and a standard rodent diet. The study commenced after a period of cage acclimatisation. 65 of the rats were dosed orally with paracetamol (600 mg/kg) in an aqueous solution containing methylcellulose (0.5% w/v) and Tween 80 (0.1% w/v). 10 of the rats were used as a control set and were orally dosed with the dosing vehicle only. Individual pre- and post-dose 24-hour urine samples were collected from each rat into ice-cooled vessels, which also contained a fixed volume of sodium azide solution as a preservative. The pre-dose urine samples were collected from 48-24 hours before dosing. The post-dose urine samples were collected from 0-24 hours after dosing. The final volume of each urine sample was determined without making any correction for the azide solution. The urine samples were all prepared for NMR analysis according to a standard procedure that involved the use of fixed volumes of urine, of a pH buffer solution and of a TSP/D.sub.20 solution. The $^1$H NMR spectra were acquired at 600 MHz on a Bruker NMR spectrometer equipped with a flow probe, using Bruker's 'xwinnmr' and 'iconnmr' software. Water suppression was achieved using the 'noesyprld' program. The post-dose spectra of the paracetamol-dosed rats showed extra N-acetyl signals which were found to be located at ca. 2.18, 2.165, 2.155 and 2.15 ppm after resolution enhancement. These signals were initially assigned to paracetamol sulphate (now designated 'S'), paracetamol glucuronide (now designated 'G'), the mercapturic acid derived from paracetamol (now designated 'MA'), and paracetamol itself (now designated 'P'), respectively. The mercapturic acid of paracetamol (MA) is also sometimes referred to as the N-acetylcysteine conjugate of paracetamol. Spiking with paracetamol glucuronide and paracetamol confirmed their peak assignments and the assignment of the MA acetyl was confirmed from the similarly sized peak at 1.86 ppm. Reference to the literature (Bales et al. (1984) Urinary excretion of acetaminophen and its metabolites as studied by proton NMR spectroscopy, Clin. Chem., 30, 10, 1631-1636) suggested that the N-acetyl peak of the cysteine conjugate of paracetamol would potentially overlap the N-acetyl peak of paracetamol but, in fact, it seems more likely that the N-acetyl peak of the cysteine conjugate would overlap the equivalent N-acetyl peak from the mercapturic acid. This leaves some uncertainty over the quantitation of both MA and P and, henceforth, when we refer to models and data for MA and P, it should be remembered that the measured quantities might contain some contribution from the cysteine conjugate. No significant interferences were present in the spectra of the post-dose control samples. Quantitation of the various paracetamol-related urinary metabolites, including paracetamol itself, was achieved by reference to the relevant acetyl signals in the chemical range 2.22-2.11 ppm although other signals could also potentially have been used. The complete cluster of N-acetyls signals from ca. 2.22 to ca. 2.11 ppm was first integrated relative to the TSP signal, in the post-dose spectra, giving a measure of the total amount of N-acetylated species in each NMR sample. A relative measure of the total excretion of N-acetylated species by each rat in the 0-24 hr post-dose period was then calculated as (total N-acetyls integration/ TSP integration)*volume of urine collected (in milliliters). Subsequently, each post-dose spectrum was resolution-enhanced using a gaussian multiplication (lb-1, gb 0.5) and the signals from the four components S, G, MA and P were integrated relative to one another. These values were summed and then the amount of each component was calculated as a fraction of the total. As other components of the N-acetyls cluster were relatively insignificant, combining these fractional values for S, G, MA and P with the value for the total acetyls excretion for each animal gave an estimate of the amount of each component excreted by that animal. The S/G ratio was calculated. The pre-dose spectra were normalised in two different ways. In the first approach, the total spectral integration between 9.5 and 0.5 ppm was adjusted to constant total area after excluding the region from 6.3-4.0 ppm, which contained the residual water signals and the signal from urea, which is affected by the water suppression procedure. In the second approach, the pre-dose spectra were normalised relative to TSP, which had been added in constant amount to each NMR sample. Subsequently, each of the TSP-normalised pre-dose spectra was multiplied by the relevant volume (in milliliters) of urine collected during the pre-dose collection. Thus, in this second approach, a relative measure was obtained of the 24-hour excretion of each of the pre-dose urinary metabolites. The TSP signal was excluded prior to carrying out the chemometrics analyses.

PLS models for pre-dose to past-dose prediction were constructed using the SIMCA software from Umetrics.

FIG. 4.1 shows a plot of the observed versus PLS-predicted values for the total 0-24 hour excretion of N-acetylated compounds by rats dosed with paracetamol (600 mg/kg). The results shown are for modelling data only and relate to the first model for this parameter. This plot indicates clear correlation between the pre-dose and post-dose data. The value of RMSEE for the model is 7.98.

FIG. 4.2 shows a plot of the observed versus PLS-predicted values for the 0-24 hour excretion of MA by rats dosed with paracetamol (600 mg/kg). The results shown are for modelling data only and relate to the first model for this parameter. This plot indicates clear correlation between the pre-dose and post-dose data. The value of RMSEE for the model is 1.28.

FIG. 4.3 shows a plot of the observed versus PLS-predicted values for the total 0-24 hour excretion of N-acetylated compounds by rats dosed with paracetamol (600 mg/kg). The results shown are for modelling data only and relate to the second model for this parameter. This plot indicates clear correlation between the pre-dose and post-dose data. The value of RMSEE for the model is 12.99.

FIG. 4.4 shows the successful internal validation of the model that generated the pre-dose predictions shown in FIG. 4.3. This plot proves that the correlation between the pre- and post-dose data, indicated by FIG. 4.3, is not random. External validation of the model was also successful and produced an RMSEP value of 12.89, which was comparable with the RMSEE value of 12.99 for the model.

FIG. 4.5 shows a plot of the observed versus PLS-predicted values for the 0-24 hour excretion of paracetamol glucuronide ('G') by rats dosed with paracetamol (600 mg/kg). The results shown are for modelling data only. This plot indicates clear correlation between the pre-dose and post-dose data. The value of RMSEE for the model is 6.99.

FIG. 4.6 shows the successful internal validation of the model that generated the pre-dose predictions shown in FIG. 4.5. This plot proves that the correlation between the pre- and post-dose data, indicated by FIG. 4.5, is not random. External validation of the model was also successful and produced an RMSEP value of 7.27, which is comparable with the RMSEE value of 6.99 for the model.

FIG. 4.7 shows a plot of the observed versus PLS-predicted values for the 0-24 hour excretion of 'MA' by rats dosed with paracetamol (600 mg/kg). The results shown are for modelling data only and relate to the second model for this parameter. This plot indicates clear correlation between the pre-dose and post-dose data. The value of RMSEE for the model is 1.90.

FIG. 4.8 shows the successful internal validation of the model that generated the pre-dose predictions shown in FIG. 4.7. This plot proves that the correlation between the pre- and post-dose data, indicated by FIG. 4.7, is not random. External validation of the model was also successful and produced an RMSEP value of 1.32, which is comparable with the RMSEE value of 1.90 for the model. The external validation is shown in FIG. 4.9 where the unfilled circles are the model-building data and the filled circles are test data that were not used in the model-building exercise.

FIG. 4.10 shows a plot of the observed versus PLS-predicted values for the excretion of 'P' by rats dosed with paracetamol (600 mg/kg). The results shown are for modelling data only. This plot indicates that there is correlation between the pre-dose and post-dose data. The value of RMSEE for the model is 3.51.

FIG. 4.11 shows the internal validation of the model that generated the pre-dose predictions shown in FIG. 4.10. This plot proves that the correlation between the pre- and post-dose data, indicated by FIG. 4.10, is not random. External validation of the model was also successful and produced an RMSEP value of 3.30, which is comparable with the RMSEE value of 3.51 for the model.

Direct pre-dose prediction of the amount of 'S' excreted post-dose was not achieved. However, by subtracting the predictions for the amounts of 'G', 'P' and 'MA' excreted from the prediction for the total excretion of N-acetylated species it was possible to generate a pre-dose prediction for the amount of 'S' excreted by each rat in the 24-hour post-dose period. By combining that prediction for 'S' with the appropriate prediction for 'G' it was possible to obtain a pre-dose prediction for the post-dose G/S ratio for each rat. FIG. 4.12 shows the observed versus predicted values for the amount of 'S' excreted. FIG. 4.13 shows the observed versus predicted values for the G/S ratio.

The results of this study demonstrate that the new methodology is not limited simply to predictions of responses determined by acetylator phenotype. The results presented here indicate that pre-dose predictions can be made regarding the amounts, and the relative extent, of glucuronidation and mercapturic acid formation and that occur on dosing paracetamol. Prediction of the amount of paracetamol sulphate excreted in the urine was not so readily achieved but the results obtained suggested that it might be predictable by difference'. MA, the mercapturic acid derived from paracetamol, has special toxicological significance as it thought to originate from the conjugation of a toxic, reactive intermediate with glutathione. Glucuronidation, sulphation and glutathione conjugation are three of the most important transformations of Phase 2 metabolism and each has a major defensive role in regard to a variety of exogenous substances. Thus, the present data indicate that subject-specific pre-dose predictions might be made with respect to the metabolism and toxicity of a large number of exogenous compounds. Given the examples shown, there is every reason to believe that pre-dose urinary discriminators exist for a wide variety of other aspects of metabolic phenotype i.e. that pre-dose prediction models could be built for a wide variety of aspects of metabolic phenotype and for dosing responses governed by one or more of those aspects.

Example 5

Pre-Dose Prediction of Urinary Paracetamol Metabolite Quantities in Human Males Subsequently Dosed with Paracetamol (1000 mg)

An example showing that numerical pre-dose to post-dose predictions can be achieved in humans.

99 adult human male subjects were recruited for an ethically-approved clinical trial. Certain dietary restrictions were stipulated such as not eating fish and not drinking alcohol for a certain period. To be eligible for the study, it was necessary that the subjects were not taking paracetamol or other drugs for a certain period prior to the study. The weight and height of each subject was recorded. On the day of the study, a 'snapshot' mid-stream pre-dose urine sample was first provided by each subject. Subsequently, each subject took 2×500 mg tablets of paracetamol BP with a fixed volume of water. After dosing, each subject was required to provide all of the urine that he produced over two consecutive time periods, namely 0-3 hours and 3-6 hours from dosing. At the end of each of those time periods, each subject was requested to empty his bladder as completely as possible and the mass of urine produced by each subject over each post-dose time period was recorded. The urine samples were all prepared for NMR analysis according to a standard procedure, which involved the use of 440 microliters of urine. The $^1$H NMR spectra were acquired at 600 MHz on a Bruker NMR spectrometer using Bruker's 'xwinnmr' and 'iconnmr' software. Water suppression was achieved using the 'noesyprld' program. In the post-dose spectra, the N-acetyls signals from 2.210 to 2.135 ppm were first integrated relative to TSP and a measure of the total excretion of N-acetylated species by each subject for each period was determined as (acetyls integration/TSP integration)*mass of urine collected (in g). This formula is based on the assumption that the density of the urine samples is nearly constant. As a check, the sample densities of a number of representative samples were measured and were found to lie in the range 1.00-1.04 g/ml i.e. the assumption of nearly constant density was reasonable. Subsequently, the post-dose spectra were resolution-enhanced using a gaussian multiplication of the FID (lb −1, gb 0.5). Where possible, the amounts of paracetamol sulphate (S), paracetamol glucuronide (G) and unchanged paracetamol (P) were then measured directly as fractions of the total integration from 2.210-2.135 ppm. It was not possible to obtain an accurate measure of the amounts of unchanged paracetamol (P) excreted during the 3-6 hour collection and this data was not used. The level of paracetamol mercapturic acid (MA) was not generally high enough to be measurable with accuracy. The amounts of the individual paracetamol metabolites (S, G and P) excreted by each subject during a particular collection period were calculated by multiplying the total excretion of N-acetylated species for that subject and period (previously calculated) by the relevant fractions of the 2.210-2.135 ppm integration. Where appropriate the data for the two collections was summed to give data for the whole 0-6 hour post-dose period. Because the effective dose of paracetamol received by any particular subject was dependent on his body mass, the excretion results for total N-acetyls, S, G and P were combined with the body mass data to give excretion per kg of body mass. It should be noted that, as with the paracetamol study in the rat, it is possible that the cysteine conjugate of paracetamol could have influenced the quantitation of unchanged paracetamol. The pre-dose spectra were normalised in two different ways (to total spectral area, after excluding certain regions, and to constant creatinine) and PLS models for pre-dose to post-dose prediction were constructed using the SIMCA software from Umetrics.

FIG. 5.1 shows the observed versus PLS-predicted values for the total excretion of N-acetylated compounds (0-3 hour collection) per kg of body mass for male volunteers who took paracetamol (1000 mg). The results shown are for modelling data only. This plot indicates that clear correlation was found between the pre-dose and post-dose data. The value of RMSEE for the model was 1.12.

FIG. 5.2 shows the observed versus PLS-predicted values for the total excretion of N-acetylated compounds (0-3 hour collection) per kg of body mass for an external test set that was analysed in relation to the model underlying FIG. 5.1.

The RMSEP value was 0.80, which compares favourably with the model's RMSEE value of 1.12.

FIG. 5.3 shows the observed versus PLS-predicted values for the excretion of paracetamol glucuronide ('G') (0-3 hour collection) per kg of body mass for male volunteers who took paracetamol (1000 mg). The results shown are for modelling data only. This plot indicates that correlation was found between the pre-dose and post-dose data. The value of RMSEE for the model was 0.84.

FIG. 5.4 shows the observed versus PLS-predicted values for the excretion of 'G' (0-3 hour collection) per kg of body mass for an external test set that was analysed in relation to the model underlying FIG. 5.3. The RMSEP value was 0.70, which compares favourably with the model's RMSEE value of 0.84.

FIG. 5.5 shows the observed versus PLS-predicted values for the excretion of 'P' (0-3 hour collection) per kg of body mass for male volunteers who took paracetamol (1000 mg). The results shown are for modelling data only. This plot indicates that correlation was found between the pre-dose and post-dose data. The value of RMSEE for the model was 0.185.

FIG. 5.6 shows the observed versus PLS-predicted values for the excretion of 'P' (0-3 hour collection) per kg of body mass for an external test set that was analysed in relation to model underlying FIG. 5.5. The RMSEP value was 0.170, which compares favourably with the model's RMSEE value of 0.185.

FIG. 5.7 shows the observed versus PLS-predicted values for the total excretion of N-acetylated compounds (0-6 hour period) per kg of body mass for male volunteers who took paracetamol (1000 mg). The results shown are for modelling data only. This plot indicates that clear correlation was found between the pre-dose and post-dose data. The value of RMSEE for the model was 1.47.

FIG. 5.8 shows the observed versus PLS-predicted values for the total excretion of N-acetylated compounds (0-6 hour period) per kg of body mass for an external test set that was analysed in relation to the model underlying FIG. 5.7. The RMSEP value was 1.13, which compares favourably with the model's RMSEE value of 1.47.

The results from this study confirm the principle that the methodology can be extended from rats to humans and it is assumed that the methodology could be applied successfully to all mammals. In particular, it is notable that the method worked in humans who were not subject to full dietary control and, with such control in place, improved results would be expected. The findings presented here represent a preliminary analysis of the samples and data and improved models may well be possible. It is possible that use of a standard analytical method, such as HPLC, with UV-Visible detection, in relation to the post-dose samples would provide improved quantitation of the paracetamol metabolites and would therefore facilitate the model building. In particular, the use of such a technique should permit improved quantitation of P and MA compared to the NMR method used here. Furthermore, it is believed that improved models might be obtained by taking ratios and other combinations of the pre-dose variables (which, in this case, are the 0.04 ppm wide segments of the pre-dose NMR spectra) before carrying out the PLS analysis.

Hypothetical Examples

A principal feature of the present invention is to be able to predict responses to dosing and thereby to select appropriate dosing substances and treatment regimes e.g. pharmaceutical treatments, anaesthetics etc. Such methods would enable, on the basis of pre-determined criteria, such as toxicity, efficacy and side-effects, the identification of appropriate dosing substances, the identification of maximum or minimum doses, the identification of appropriate doses, appropriate dosing frequencies, appropriate numbers of doses and the selection of appropriate controlled-release formulations. Typical construction of these methods is shown in the following hypothetical example, which involves identifying the minimum dose of an antibacterial substance for clearing an infection of a particular type within a set period of time. Thus, different model building populations suffering from the specified infection would be treated with different levels of the antibacterial. Data pertaining to dose levels which did not clear up the infection in any of the subjects within the set period would be deleted from the analysis. For each of the other data sets, a classification model would be built to identify the pre-dose characteristics of those subjects that met the clear-up criterion and the pre-dose characteristics of those subjects that did not. Test data of a subject would be analysed in relation to each of the models to find the minimum dose commensurate with clear-up of the infection in a subject of that phenotype. This dose would not necessarily be administered; such administration might depend, for instance, on whether unacceptable side effects would be expected in the subject at that dose level.

Another feature of the present invention is the ability to select a phenotypically homogenous set of subjects for whatever purpose. Typically, the requirement would be to select a group of subjects which were homogenous with respect to one element of metabolic phenotype e.g. N-acetylator phenotype. For this example a model would be built using a dosing substance that challenged N-acetylation. A classification model would then be built according to imposed homogeneity criteria. Test data relating to subjects of unknown N-acetylator phenotype would be examined in relation to the model and the subject classified accordingly. The subjects falling into one class would be considered as phenotypically homogenous with respect to N-acetylation of the dose substance.

Likewise the invention permits the rationalisation of variable data obtained in studies such as studies of toxicity or efficacy. For instance, a dosing regime which caused toxicity in one group but not in another group might be rationalised if it was found, by use of pre-dose phenotyping, that one group were fast O-methylators whilst the other group were slow O-methylators. Such an indication would lead to a consideration of the metabolism of the dosed substance and possibly to the identification of a critical O-methylation step which either produced or eliminated a toxic metabolite.

Another feature of the present invention is to facilitate the identification of pre-dose biomarkers or biomarker combinations, which by their presence or concentrations in a pre-dose sample would indicate a particular metabolic phenotype or a particular response to a potential dosing substance. For example, in a PCA, a scores plot which provides separation of the different classes of interest would be compared to the corresponding loadings plot. The pre-dose variables that provide the discrimination, and the positive or negative nature of their correlation to the class separation, can then be identified. Sometimes these variables may be directly attributable to particular compounds. In the case of NMR spectroscopic data, a particular variable or combination of variables would indicate the spectral regions containing the discriminating features. By examination of those regions of the model building spectra the discriminating compound(s) (or "biomarkers") could then, in principle, be identified.

Sometimes it would be necessary to take samples from a number of subjects to be representative of a wider group of subjects. For instance, one would normally only be able to sample a few plants from a field of such plants. From analysis of the characteristics of the selected plants one might then wish to select a particular dose of herbicide for the whole field.

What is claimed is:

1. A model system, wherein the model predicts, without dosing, the post-dose response of an individual where the response is dependent on the individual's metabolic phenotype, the model system comprising:
   a) pre-dose data of a plurality of subjects or samples thereof before dosing with a dosing substance;
   b) post-dose data of the plurality of subjects or samples thereof after dosing with the dosing substance; and
   c) a processor that identifies and correlates inter-subject variation in the pre-dose data with inter-subject variation in the post-dose data using a pattern recognition (PR) technique, wherein the inter-subject variation in the post-dose data corresponds to different responses of the subjects to the dosed substance, thereby producing a pre-to-post-dose predictive model,
   wherein the processor applies the pre-to-post-dose predictive model to the individual's pre-dose data and classifies the individual's post-dose response, without dosing of the individual;
   wherein the pre- and/or post-dose data comprise chemical composition data and/or physical parameter data of samples and/or subjects;
   wherein the pre-to-post-dose predictive model consists of one or more mathematical equations defining the relationship between pre-dose and post-dose data.

2. The model system according to claim 1, wherein the pre- and/or post-dose data are obtained from samples which are biofluids such as urine, blood, blood plasma, blood serum, saliva, sweat, tears, breath or breath condensate.

3. The model system according to claim 2, wherein the pre- and/or post-dose samples or subjects are treated prior to analysis so as to enhance data recovery or to improve sample stability.

4. The model system according to claim 1 wherein the pre- and/or post-dose data are derived from or are compositional data acquired using nuclear magnetic resonance (NMR) spectroscopy and/or any other chemical analysis techniques such as mass spectroscopy (MS), infrared (IR) spectroscopy, gas chromatography (GC) and high performance liquid chromatography (HPLC) or by using any integrated combination of such techniques.

5. The model system according to claim 4 wherein the pre- and/or post-dose data are physical data or data derived therefrom.

6. The model system according to claim 1 wherein, the model system comprises the post-dose data of a plurality of dosing substances.

7. The model system according to claim 6 wherein the pre-dose data set is extended, prior to pattern recognition, by taking ratios and/or other combinations of existing variables.

8. The model system according to claim 7 wherein, for a group of subjects dosed with any particular substance, the pattern recognition method is used to identify patterns in the variable metabolism of, or the variable reactions to, the dosing substance.

9. The model system according to claim 1 wherein, for a group of subjects dosed with any particular substance, a supervised pattern recognition method is used to identify variation in the pre-dose data that correlates with the variation of interest in the post-dose data.

10. The model system according to claim 1 wherein the model identifies biomarkers or combinations of biomarkers which are used to predict responses to dosing.

* * * * *